US008299285B2

(12) United States Patent
Dilworth et al.

(10) Patent No.: US 8,299,285 B2
(45) Date of Patent: Oct. 30, 2012

(54) COMPOUNDS FOR IMAGING AND THERAPY

(75) Inventors: Jonathan Robin Dilworth, Oxford (GB); Josephine Mary Peach, Oxford (GB); Julia May Heslop, Oxford (GB); Paul Stephen Donnelly, Melbourne (AU)

(73) Assignee: Isis Innovation Limited, Summertown, Oxford (GB)

( * ) Notice: Subject to any disclaimer, the term of this patent is extended or adjusted under 35 U.S.C. 154(b) by 1133 days.

(21) Appl. No.: 11/988,230

(22) PCT Filed: Jul. 5, 2006

(86) PCT No.: PCT/GB2006/002488
§ 371 (c)(1),
(2), (4) Date: Apr. 28, 2008

(87) PCT Pub. No.: WO2007/003944
PCT Pub. Date: Jan. 11, 2007

(65) Prior Publication Data
US 2011/0098353 A1 Apr. 28, 2011

(30) Foreign Application Priority Data
Jul. 5, 2005 (GB) .................................. 0513812.8

(51) Int. Cl.
C07F 1/08 (2006.01)
A61B 5/055 (2006.01)
A61K 31/00 (2006.01)
(52) U.S. Cl. .......... 556/34; 514/494; 514/499; 514/501; 546/12; 548/106; 549/210; 556/35; 558/35; 564/243; 424/9.36; 424/9.361
(58) Field of Classification Search .................... 558/35; 556/34, 35; 549/210; 548/106; 546/12; 564/243; 514/494, 499, 501; 424/9.36, 9.361
See application file for complete search history.

(56) References Cited

U.S. PATENT DOCUMENTS

| 3,483,207 | A | 12/1969 | Winkelmann et al. |
| 3,674,873 | A | 7/1972 | Barrett |
| 3,792,052 | A | 2/1974 | Sharp et al. |
| 5,843,400 | A | 12/1998 | Fujibayashi et al. |

FOREIGN PATENT DOCUMENTS

| EP | 0 306 168 | 3/1989 |
| EP | 0 606 683 | 7/1994 |
| EP | 0 726 077 | 8/1996 |
| FR | 1528968 | 6/1968 |
| GB | 793802 | 4/1958 |
| GB | 1143940 | 2/1969 |
| GB | 1 448 295 | 9/1976 |
| JP | 7-72571 | 3/1995 |
| WO | 92/07860 | 5/1992 |

OTHER PUBLICATIONS

Jones et al., Journal of Chemical Society [Section] A: Inorganic, Physical, Theoretical (1970), vol. 17, pp. 2829-2836.*
Kanaoka et al., Chem. Pharm. Bull., vol. 15, No. 11, pp. 1738-1743 (1967).*
J.P. Scovill, Phosphorus, Sulfur, Silicon and Related Elements, 1991, 60, 15.
K. Karidi et al., Dalton Trans., 2005, 1176.
Esiri, M.M., et al., The Neuropathology of Dementia: Second Edition, Cambirdge University Press, 2004.
LeVine, H., Protein Sciences, 1993, 2, p. 404-10.
Sun, A., et al., J. Histochem. Cytochem., 2002, 50, p. 463-72.
Gallyas, F., Acta Morphol. Acad. Sci. Hungry, 1971, 19, p. 1-8.
Mathis, C.A., et al., J. Med. Chem., 2003, 46, p. 2740-54.
Vassar, P.S. and Culling, C.F.A., Arch. Pathol., 1959, 68, p. 487-98.
Zhuang, Z.-P., et al., J. Med. Chem., 2003, 46, p. 231-43.
Krebs, M.P.H., et al., J. Struct. Biol., 2005, 149, p. 30-7.
Klunk, W.E., et al., J. Neurosci., 2003, 23, p. 2086-3000.
Zhuang, Z.-P., et al., Nucl. Med. Biol., 2005, 32, p. 171-84.
Styren, S.D., et al., J. Histochem. Cytochem., 2000, 48, p. 1223-32.
Salki, M., et al., J. Mol. Biol., 2005, p. 983-98.
Lockhart, A., et al., J. Bio. Chem., 2005, 280, p. 7677-84.
van Gurp, M. and LeVine, H., J. Chem. Phys., 1989, 90, p. 4095-102.
van Gurp, M., et al., J. Chem. Phys., 1989, 90, p. 4103-15.
Salemme, F.R., Prog. Biophys. Mol. Biol., 1983, 42, p. 95-133.
Voropai, E.S., et al., J. Appl. Spectrosc., 2003, 70, p. 868-74.
Kung, M.-P., et al., Brain Res., 2002, 956, p. 202-10.
Solbach, C., et al., App. Rad. Isotopes, 2005, 62, p. 591-5.
Blower, P.J., et al., Nucl. Med. Biol., 1996, 23, p. 957-80.
Lewis, J.S. and Welch, M.J., Technetium, Rhenium and Other Metals in Chemistry and Nuclear Medicine, 2002, 6, p. 23-33.
Fujibayashi, Y., et al., Biol. Pharm. Bull., 1993, 16, p. 146-9.
Dearling, J.L.J., et al., J. Biol. Inorg. Chem., 2001, 7, p. 249-59.
Cowley, A.R., et al., J. Am. Chem. Soc., 2002, 124, p. 5270-1.
McQuade, P., et al., Nucl. Med. Biol., 2005, 32, p. 147-56.
Beraldo, H. and Gambino, D., Mini Reviews in Medicinal Chemistry, 2004, 4, p. 31-9.
De Santis, G., et al., Inorg. Chem., 1995, 34, p. 3561-2.
Bernhardt, P.V., et al., J. Chem. Soc., Dalton Trans., 1999, p. 3579-84.
Mathis Chester,.A., et al., Bioorg. Med. Chem. Lett., 2002, 12, p. 295-8. Shi, D.-F., et al., J. Med. Chem., 1996, 39, p. 3375-84.
Hutchinson, I., et al., J. Med. Chem, 2001, 44, p. 1446-55.
Kashiyama, E., et al., J. Med. Chem., 1999, 42, p. 4172-84.
De Leon-Rodriguez, L.M., et al., Chem, Eur. J., 2004, 10, p. 1149-55.
Hutchinson, I., et al., J. Med. Chem, 2002, 45, p. 744-7.
Han, S.-Y. and Kim, Y.-A., Tetrahedron, 2004, 60, p. 2447-67.
Gomez, S., et al., Adv. Synth. Catal., 2002, 10, p. 1037-57.
Heinen, A.W., et al., Eur. J. Org. Chem, 2000, p. 2501-6.
Wayne, R.P., Principles and Applications of Photochemistry, 1986.
Dilworth, J.R. and Parrott, S.J., Chem. Soc. Rev., 1998, 21, p. 43-55.
Blower, P.J., et al., Dalton Trans., 2003, p. 4416-25.
Gummerus, G.R., Commentaliones Hysico Mathematicae, 1966, 32, p. 43.
John, E.K. and Green, M.A., J. Med. Chem., 1990, 33, p. 1734-70.
Murthy, N. and Dharmarajan, T.S., Asian J. Chem., 14, p. 1325-30.
Keda, K., et al., Acta Neuro., 1989, 78, p. 137-42.
West, D. X.; Padhye, S. B.; Sonawane, P. B. Struct. Bonding 1991, 76, 1.

(Continued)

Primary Examiner — Porfirio Nazario Gonzalez
(74) Attorney, Agent, or Firm — Nixon & Vanderhye P.C.

(57) ABSTRACT

A metal complex of formula (III) wherein: M is a transition metal and A1, A2, X, X', Y, L1', R1' and R2' are as defined herein, is useful in medical imaging and therapy.

23 Claims, 5 Drawing Sheets

OTHER PUBLICATIONS

Maurer, R. I.; Blower, P. J.; Dilworth, J. R.; Reynolds, C. A.; Zheng, Y.; Mullen, G. E. D. J. Med. Chem. 2002, 45, 1420.
French, F.; Freedlander, B. Cancer Res. 1958, 18, 1290.
John, E. K.; Green, M. A. J. Med. Chem. 1990, 33, 1764.
Petering, H. G.; Buskirk, H. H.; Crim, J. A.; Van Giesen, G. J. Pharmacologist 1963, 5, 271.
Cappuccino, J. G.; Banks, S.; Brown, G.; George, M.; Tarnowski, G. S. Cancer Res. 1967, 27, 968.
Minkel, D. T.; Chan-Stier, C.; Petering, D. H. Mol. Pharmacol. 1976, 12, 1036.
Mohan, M.; Sharma, P.; Kumar, M.; Jha, N. K. Inorg. Chim. Acta 1986, 125, 9.
Rodriguez-Arguelles, M. C.; Ferrari, M. B.; Fava, G. G.; Pelizzi, C.; Tarasconi, P.; Roberto, A.; Dall'Aglio, P. P.; Lunghi, P.; Pinelli, S. J. Inorg. Biochem. 1995, 58, 157.
Frausto da Silva, J. J. R.; Williams, R. J. P. The biological chemistry of the elements; Oxford University Press, 2001.
Ferrari, M. B.; Fava, G. G.; Pelizzi, C.; Tarasconi, P. J. Chem. Soc., Dalton Trans. 1992, 2153.
Hennig, C.; Hallmeier, K.-H.; Zahn, G.; Tschwatschal, F.; Hennig, H. Inorg. Chem. 1999, 38, 38.
Rodriguez-Arguelles, M. C.; Battaglia, L. P.; Ferrari, M. B.; Fava, G. G.; Pelizzi, C.; Pelosi, G. J.Chem. Soc., Dalton Trans. 1995, 2297.
López-Torres, E.; Mendiola, M. A.; Pastor, C. J.; Perez, B. S. Inorg. Chem. 2004, 43, 5222.
Fujibayashi, Y.; Taniuchi, H.; Yonekura, Y.; Ohtani, H.; Konishi, J.; Yokoyama, A. J. Nucl. Med. 1997, 38, 1155.
Carvalho, S.; Cruz, C.; Delgado, R.; Drew, M. G. B.; Felix, V. Dalton Trans. 2003, 4261.
Ghosh, U.; Kundu, N.; Malty, G; Choi, K.-Y.; Caneschi, A.; Endo, A.; Chaudhury, M. Inorg. Chem. 2004, 43, 6015.
Kaden, T. A.; Riesen, A.; Schneider, R. Helv. Chim. Acta 1985, 69, 53.
Ciampohni, M.; Fabbrizzi, L.; Perotti, A.; Poggi, A.; Seghi, B.; Zanobini, F. Inorg. Chem. 1987, 26, 3527.
Anderson, O. P.; la Cour, A.; Findeisen, M.; Hennig, L.; Simonsen, O.; Taylor, L. F.; Tottlund, H. Inorg. Chem. 1999, 38, 38.
Arano, Y.; Horiuchi, K.; Hosotani, T .; Saji, H.; Torizuka, K.; Yokoyama, A. Nuc. Med. Biol. 1988, 13, 603.
Petering, H. G.; Buskirk, H. H.; Underwood, G. E. Cancer Res. 1964, 24, 367.
Gummerus, G. R. Commentaliones Hysico Mathematicae 1966, 32, 43.
Gingras, B. A.; Suprunchuk, T.; Bayley, C. H. Can. J. Chem. 1962, 40, 1053.
Lieber, E.; Slutkin, R. J. Org. Chem. 1962, 27, 2214.
Dyson, G. M. J. Chem. Soc. 1924, 1702.
Klopping, H. L.; Van Der Kerk, G. J. M. Recl. Trav. Chim. 1951, 70, 949.
Garin, J.; Melendez, E.; Merchan, P.; Merino, P.; Tejero, T. Bull. Soc. Chim. Belg. 1989, 98, 289.
Cowley, A. R; Dilworth, J. R.; Donnelly, P. S.; Gee, A. D.; Heslop, J. M. Dalton Trans. 2004, 2404.
Duceppe, J. S.; Gauthier, J. J. Heterocyclic Chem. 1984, 21, 1685.
Lieber, E.; Pillei, C. N.; Hites, R. D. Can. J. Chem. 1957, 35, 832.
Novak-Hoter, I.; Schubiger, A. P. Eur. J. Nucl. Med. 2002, 29, 821.
Archer, C. M.; Dilworth, J. K.; Jobanputra, P.; Thompson, R. M.; McPartlin, M.; Hiller, W. J. Chem. Soc., Dalton Trans. 1993, 897.
Abrams, M. J.; Juweid, M.; tenKate, C. I.; Schwartz, D. A.; Hauser, M. M.; Gaul, F. E.; J., F. A.; Rubin, R. H.; Strauss, H. W.; Fischman, A. J. J. Nucl. Med. 1990, 31, 2022.
Greenland, W. E. P.; Howland, K.; Hardy, J.; Fogelman, I.; Blower, P. J. J. Med. Chem. 2003, 46, 1751-1757.
Banerjee, S. R.; Maresca, K. P.; Francesconi, L.; Valliant, J.; Babich, J. W.; Zubieta, J. Nucl. Med. Biol 2005, 32, 1.
Liu, S. Chem. Soc. Key. 2004, 33, 445.
Gabriel, M.; Decristotoro, C.; Donnemiller, E.; Ulmer, H.; Rychlinski, W.; Mather, S. J.; Moncayo, R. J. Nucl. Med. 2003, 44, 708.
Anderson, C. J.; Welch, M. J. Chem. Rev. 1999, 99, 2219.
Bass, L. A.; Wang, M.; Welch, M. J.; Anderson, C. J. Bioconj. Chem. 2000, 11, 527.
Boswell, C. A.; Sun, X.; Niu, W.; Weisman, G. R.; Wong, E. H.; Rheingold, A. L.; Anderson, C. J. J. Med. Chem. 2004, 47, 1465.
Lewis, E. A.; Boyle, R. W.; Archibald, S. J. Chem. Commun. 2004, 2212.

Obata, A.; Yoshimi, E.; Waki, A.; Lewis, J. S.; Oyama, N.; Welch, M. J.; Saji, H.; Yonekura, Y.; Fujibayashi, Y. Annals of Nuclear Medicine 2001, 15, 499.
Y. Arano, A. Yokoyama, Y. Magata, H. Saji, K. Horiuchi and K. Torizuka, Int. J. Nucl. Med. Biol., 1986, 12, 425.
T. Hosotani, A. Yokoyama, Y. Arano, K. Honuchi, H. Wasaki, H. Saji and K. Torizuka, Int. J. Nucl. Med. Biol., 1986, 12, 431.
D. W. McPherson, G. Umbricht and J. F. F. Knapp, J. Labelled Compd Radiopharm., 1990, 28, 877.
Y. Arano, A. Yokoyama, T. Furukawa, K. Horuichi, T. Yahata, H. Saji, H. Sakahara, T. Nakashima, M. Koizumi, K. Endo and K. Toruzulia, J. Nucl. Med., 1987, 28, 1027.
Dearling Jason L.J. et al., "REDOX-Active Metal Complexes for Imaging Hypoxic Tissues: Structure-Activity Relationships in Copper(II) Bis(Thiosemicarbazone) Complexes", Chemical Communications, vol. 4, No. 22, pp. 2531-2532, (Nov. 21, 1998) United Kingdom, XP-002405152.
Xue, Zhao-Ming et al., "One- and Two-Photon Excited Dual Fluorescence Properties of Zinc(II) and Cadmium(II) Complexes Containing 4-Dipropylamino-Benzaldehyde Thiosemicarbazone", Journal of the Royal Society of Chemistry, pp. 1373-1378, (2003), XP-002405153.
Mathis, Chester A., et al., "A Lipophilic Thioflavin-T Derivative for Positron Emission Tomography (PET) Imaging of Amyloid in Brain", Bioorganic & Medicinal Chemistry Letters, vol. 12, pp. 295-298, (2002), XP002285913.
Fujibayashi Y., et al., "New Nonnitroimidazole Hypoxia Imaging Agents, Cu-62-Dithiosemiccarbazone Complexes With Low REDOX Potential", No. 197, Journal of Nuclear Medicine, Society of Nuclear Medicine, vol. 36, No. 5, pp. 49P, (May 1995), XP002027512.
Baker, Erica et al., "Evaluation of the Iron Chelation Potential of Hydrazones of Pyridoxal, Salicylaldehyde and 2-Hydroxy-1-Naphthylaldehyde Using the Hepatocyte in Culture", vol. 15, No. 3, pp. 492-501, (1992), XP000654330.
Toropave et al., Citation No. 4040599, Beilstein Crossfire Institut Zur Foerderung Der Chemischen Wissenschaften, DE, BRN 4061248 4062522 4057408 (1973), XP002405160.
Beilstein Registry No. 8810575, Beilstein Crossfire Institut ZuR Foerderung DER Chemischen Wissenschaften, DE; (2000), XP002405161.
Beilstein Registry No. 4011628, Beilstein Crossfire Institut ZuR Foerderung DER Chemischen Wissenschaften, DE; (1978), XP002405162.
Dilanyan, E.R. et al., "Comparative Polarographic Study of Copper Chelates of Substituted Bis(Thiosemicarbazones)", 1 page, (1985), Chemical Abstracts Service, Columbus, Ohio, US, XP002405163.
Ovsepyan, T.R. et al., "Novel Bisthiosemicarbazones of Glyoxal, Benzil, and Their Chelates With Copper (2+): Synthesis and Biological Activity", 1 page, (1990), Chemical Abstracts Service, Columbus, Ohio, US, XP002405164.
Dilanyan, E.R. et al., "Synthesis and Antitumor Activity of New Methylglyoxal and Blucosone Bisthiosemicarbazones and Their Copper Complexes", 1 page, (2001), Chemical Abstracts Service, Columbus, Ohio, US, XP002405165.
International Search Report mailed Mar. 15, 2007.
Written Opinion of the International Searching Authority mailed Mar. 15, 2007.
Cowley et al, J. Chem. Soc., Chem. Commun., 2005, 7, 845-847.
Ciampolini, M. et al., J. Chem. Soc., Chem. Commun., 1984, 998.
Soibinet, M. et al., Eur. J. Inorg. Chem., 2003, 1984.
D.X. West et al., Polyhedron, 1997, 16, 1895.
O. Rohde et al., J Am. Chem. Soc., 1974, 96, 5311.
Klunk, W.E. et al., Life Sciences, 2001, 69, p. 1471-84.
Ha, T., Single Molecule, 2001, 2, 283-4.
Jensen, K.A. et al., Z.Anorg. Allg. Chem., 1934, 219, 243.
Archiv der Pharmazie 2000, 333, pp. 217-225—Hall et al.
Nuclear Med. & Biol. 2000, 27, pp. 391-399—Horiuchi et al.
Polyhedron 1999, 18, pp. 2759-2767—Ackerman et al.
Nuclear Med. & Biol. 1999, 26, pp. 551-554—Ackerman et al.
Transition Metal Chem. 1998, 23, pp. 67-71—Beraldo et al.
Transition Metal Chem. 1997, 22,pp. 294-298—Beraldo et al.
Polyhedron 1997, 16, pp. 1895-1905—West et al.
J.Medicinal Chem. 1997, 40,pp. 132-136—Lim et al.

* cited by examiner

Fluorescence emission of Zn[ATS(R)/P-Carb] for excitation with DMSO at 300 nm.

Fluorescence of Zn PGTS(Et), Zn GTS(Et) and Zn GTS(Ph)

COMPOUNDS FOR IMAGING AND THERAPY

This application is the U.S. national phase of International Application No. PCT/GB2006/002488, filed 5 Jul. 2006, which designated the U.S. and claims priority to Great Britain 0513812.8, filed 5 Jul. 2005, the entire contents of each of which are hereby incorporated by reference.

FIELD OF THE INVENTION

The present invention relates to metal complexes of thiosemicarbazone derivatives that can be used in medical imaging and therapy. The present invention also relates to the unbound ligands from which the complexes are formed, to processes for producing the compounds and the complexes of the invention and to pharmaceutical compositions comprising them.

BACKGROUND TO THE INVENTION

Bis(thiosemicarbazone) complexes of transition metals have been known for nearly 50 years, and their biological activity was recognised early on. Despite demonstrations of for instance their cytotoxic, antibacterial, antimalarial, antiviral, antitumour and antifungal activity, the mechanism of their action at the cellular level remains completely unknown, although it is clear that complexes are more active than the free ligands.

There are several radionuclides of copper that have the potential to be used as radiotherapeutic or diagnostic imaging agents. For example, copper-64 ($^{64}$Cu) decays via electron capture, positron, beta and Auger emissions, which means that it can be used for both PET imaging and radiotherapeutic applications. In one embodiment the present invention relates to the development of copper radiopharmaceuticals in the form of suitable stable chelators that can be readily functionalized with appropriate biomolecules to provide stable copper bioconjugates.

The use of functionalised diazenide (NNAr, Ar=aryl or 2-pyridyl) ligands for the targeting of technetium radiopharmaceuticals particularly for the pyridyl (HYNIC) system is known. The HYNIC bifunctional chelate system is extremely versatile and has been used to conjugate technetium to chemotactic peptides, somatostatin analogues, liposomes and a folate receptor ligand. There are a number of technetium based systems in clinical trials for imaging, but the system is limited to technetium (and to a lesser extent rhenium) since these have high oxidation metal precursors which can form robust metal-nitrogen multiple bonds. The system is not suitable for use with, for example, copper radionuclides.

Most research into bifunctional chelates for targeted radiopharmaceuticals with copper isotopes has focused on the use of tetra-aza based macrocyclic ligands such as 1,4,8,11-tetraazacyclotetradecane-N,N',N'',N'''-tetraacetic acid (TETA). Despite this success and the high stability of copper-TETA complexes there is still significant loss of the radionuclide from the chelate due to transchelation with the protein superoxide dismutase.

In U.S. Pat. No. 5,843,400 Fujibayashi et al describe diagnostic agents for hypoxia or mitochondrial dysfunction, which comprise radioactive copper complexes, which agents have good transferability to the target tissue, reduction reaction affinity at a hypoxic site, high stability in a non-target site and rapidly disappear.

Z.-M. Xue, Y.-P. Tian, D. Wang and M. H. Jiang describe in *Dalton. Trans.*, 2003, 7, 1373 the fluorescence of a bis(thiosemicarbazone) complex of zinc. Cowley et al in *Chem. Commun.*, 2005, 845-847 describe the fluorescence of a bis(thiosemicarbazone) complex of zinc with a fifth apical chlorine ligand.

SUMMARY OF THE INVENTION

Figure 1:
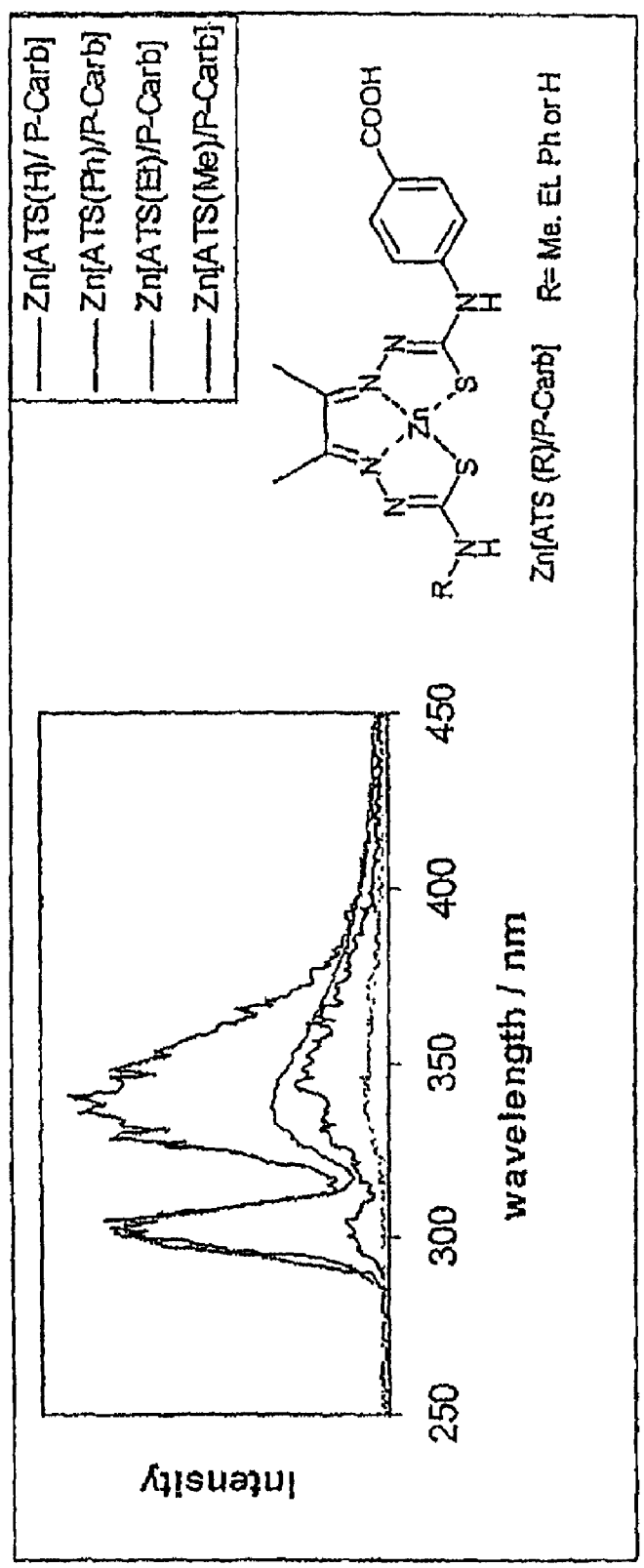
FIG. 1 shows the fluorescence emission and the compound of Example 21A.

The present invention provides a metal complex of formula (III):

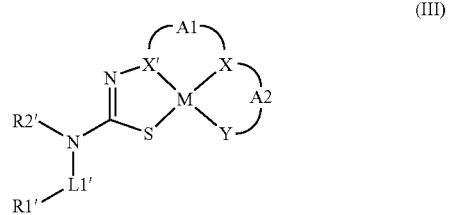

wherein:
 M is a transition metal;
 A1 is:

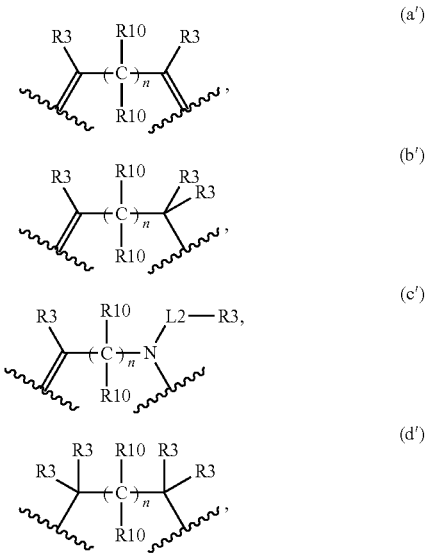

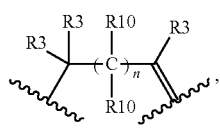
(e')

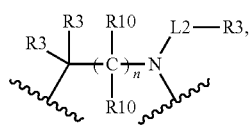
(f')

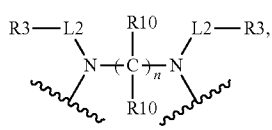
(g')

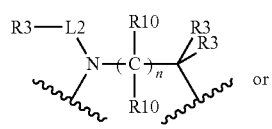
(h')

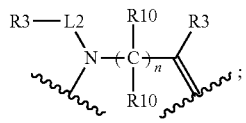
(i')

n is 0 or an integer of 1 to 5;

A2, X and Y are as defined in (i), (ii) and (iii) which follow:

(i) A2 is

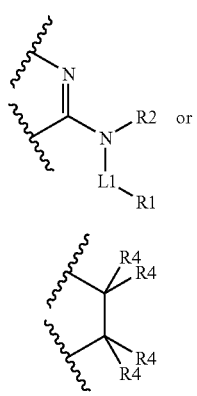

X is N or P and A1 is attached to X via a double bond, or X is O, S, N(R5) or P(R5) and A1 is attached to X via a single bond; and Y is N, O, P, S, N(R5), O(R5), P(R5) or S(R5); or (ii) X is N or P and A1 is attached to X via a double bond, or X is O, S, N(R5) or P(R5) and A1 is attached to X via a single bond; and Y and A2 together represent a moiety of formula (B):

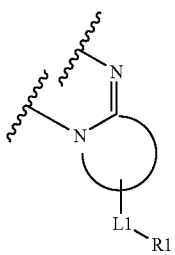

wherein the ring that is substituted by L1-R1 is a 5- to 11-membered heterocyclic group; or (iii) X, A2 and Y together represent

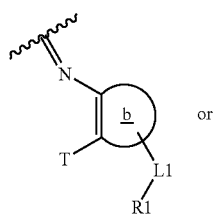

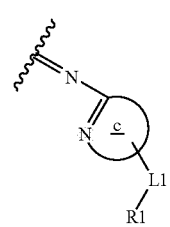

wherein T is OH, O—, COOH or C(O)O— and rings b and c are aromatic $C_{6-10}$ carbocyclic or 5 to 11 membered aromatic heterocyclic groups;

X' is N and A1 is attached to X' via a double bond, or X' is N(R5), O, S or P(R5) and A1 is attached to X' via a single bond;

L1 and L1', which are the same or different, are each independently selected from a covalent bond and a linker group selected from —C(O)—, -alk-C(O)—, —C(O)O—, -alk-C(O)O—, —OC(O)—, -alk-OC(O)—, —O—, -alk-O—, —N(R7)—, -alk-N(R7)—, —N(R7)C(O), -alk-N(R7)C(O)—, —C(O)N(R7), -alk-C(O)N(R7), —C(S)—, -alk-C(S)—, —S—, -alk-S—, —C(S)N(R7)—, -alk-C(S)N(R7)—, —N(R7)C(S)—, -alk-N(R7)C(S)—, —S(O)$_2$N(R7)—, -alk-S(O)$_2$N(R7)—, —N(R7)S(O)$_2$—, -alk-N(R7)S(O)$_2$—, —S(O)—, -alk-S(O)—, —N(R7)C(O)O—, -alk-N(R7)C(O)O—, —OC(O)N(R7)—, -alk-OC(O)N(R7)—, —N(R7)C(O)N(R7)—, -alk-N(R7)C(O)N(R7)—, —N(R7)C(S)N(R7)—, -alk-N(R7)C(S)N(R7)—, —N=C(R7)—, -alk-N=C(R7)—, —C(R7)=N— and -alk-C(R7)=N—;

R1 and R1', which are the same or different, are each independently selected from hydrogen, Z, L3-Z, L3-alk-Z, —V-L3-Z, —V-L3-alk-Z, alk-V-L3-Z, -alk-V-L3-alk-Z and a substituted or unsubstituted group selected from an alkyl, amino, carbocyclic, cycloalkyl, heterocyclic, -alk-carbocyclic, -alk-cycloalkyl and -alk-heterocyclic group, which group may be further substituted by L3-Z or L3-alk-Z, wherein L3 is as defined above for L1 and L1', —V— is a linking group of the following formula:

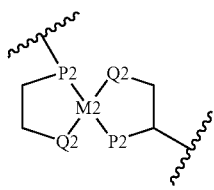

wherein P2 and Q2 are independently selected from N, O, P and S and M2 is a metal atom, and Z is a moiety selected from a biologically active molecule, a fluorophore, a cytotoxin, an amino acid, a peptide, an oligopeptide, a polypeptide, a sugar, a group containing a label, a leaving group which is replaceable by a group containing a label, and a complex of Cu, Zn or Ni with a bis(thiosemicarbazone) or a thiosemicarbazone;

-alk- is an alkylene, alkenylene or alkynylene group based on an alkyl, alkenyl or alkynyl group;

R2 and R2', which are the same or different, are each independently selected from H, $C_1$-$C_6$ alkyl and $C_1$-$C_6$ alkoxy;

each R3 is independently selected from H, $C_1$-$C_6$ alkyl, heterocyclic group and phenyl;

each R4 is independently selected from H, $C_1$-$C_6$ alkyl, heterocyclic group and phenyl;

each R5 is independently selected from H, $C_1$-$C_6$ alkyl and a group comprising an electron donor group, which donor group is separated by two carbon atoms from the O, N, S or P atom to which R5 is attached;

R7 is H, alkyl or cycloalkyl;

each R10 is independently selected from H, $C_1$-$C_6$ alkyl, heterocyclic group and phenyl; and L2 is —C(O)— or a covalent bond;

with the proviso that when X and X' are both N, Y is S, A1 is (a') and A2 is (d) then either the moiety represented by L1-R1 or the moiety represented by L1'-R1' is other than H, unsubstituted alkyl or unsubstituted alkoxy.

In formula (III) it is to be understood that, as depicted, the left-hand bond in each option for A1 is attached to X' and the right-hand bond in each option for A1 is attached to X. Likewise, as depicted in formula (III), the upper bond in each option for A2 is attached to X while the lower bond in each option for A2 is attached to Y.

Typically the overall charge on a metal complex of formula (III) as defined above is zero, in which case the complex is neutral and is not associated with a counter-ion. However, the metal complex of formula (III) may be cationic, and associated with one or more counter-anion(s). The complex may be a monocation or a dication, for example. The counter-anion(s) may be halide, hexafluorophosphate, chlorate or tetrafluoroborate anions, for example. Examples 1C, 1D, 1E, 1G and 1I hereinbelow concern the syntheses of various cationic complexes of formula (III).

In the definition of R5 above, an electron donor group is an atom or group which bears either a lone pair of electrons or an overall negative charge. It is, for instance, an O, S or N atom, or an anionic group. The electron donor group is separated by two carbon atoms from the atom to which R5 is attached; this is so that it can adopt the correct position for coordinating to the central metal atom of the complex. Typically the two carbon atoms are connected to each other by a single (saturated) bond, since this allows free rotation and thus further assists with the optimum positioning of the electron donor group. When present, the group R5 is effectively a fifth "pendant" ligand within the complex and its electron donor group becomes part of the metal co-ordination sphere. Example of suitable groups R5 include —$CH_2CO_2R_6$, —$CH_2CO_2^-$, —$CH_2CH_2N(R_6)_2$ and —$CH_2CH_2N$—(R6), wherein R6 is H or alkyl, typically H or methyl, typically H; and a group of formula (IV):

wherein ring a is a 5- or 6-membered N-containing heteroaromatic ring which is monocyclic or which is fused to a second aromatic heterocyclic ring or to a benzene ring. An example of a group of formula (IV) is a (pyrid-2-yl)methyl group. Alternatively, R5 may be H or $C_1$-$C_6$ alkyl. In particular R5 may be H, methyl or ethyl.

The present invention further provides:

a compound which is a metal-free polydentate ligand precursor to a complex of the invention as defined above;

a pharmaceutical composition comprising a complex of the invention as defined above and a pharmaceutically acceptable carrier;

a diagnostic agent or medical imaging agent which comprises a complex of the invention as defined above which is hypoxic selective;

a diagnostic agent or a medical imaging agent which comprises a complex of the invention as defined above which is not hypoxic selective and in which Z is a biologically active molecule which serves to target the complex to the desired site in vivo;

use of a complex of the invention as defined above in the manufacture of a medicament for use as a diagnostic agent, an imaging agent or a therapeutic agent; and a method of imaging a cell or in vitro biopsy sample, which method comprises: (a) contacting the cell or in vitro biopsy sample with a complex of the invention as defined above; and (b) imaging the cell or in vitro biopsy sample.

a method of imaging a patient in need thereof, which method comprises: (a) administering to the patient a complex of the invention as defined above; and (b) imaging the patient.

The invention also provides a compound which is a BTAP derivative of formula (II)

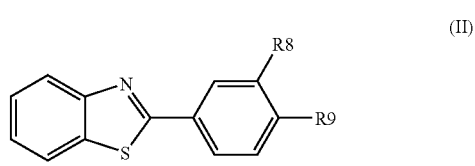

wherein

R8 is —H or —$NH_2$;

R9 is —$NH_2$, —$NHNH_2$, —N=CH-carbocyclic, —NHC(O)-carbocyclic, —NHC(O)-haloalkyl, —NHC(O)-alk-heterocyclic, —NHC(O)-aminoalkyl, —NHN=C(R6)C(O)R6 wherein R6 is H or alkyl; or R8 and R9, together with the phenyl group to which they are attached, form a benzimidazole group which is unsubstituted or substituted by a carbocyclic group.

The compounds of formula (II) are novel fluorophores which may be used as intermediates in the production of complexes of the invention as defined above wherein Z is or comprises a fluorophore.

DETAILED DESCRIPTION OF THE INVENTION

An alkyl group or moiety is a straight or branched group or moiety, which, unless otherwise specified, contains from 1 to 10 carbon atoms. A $C_{1-10}$ alkyl group or moiety is typically a $C_{1-6}$ alkyl group or moiety. A $C_{1-6}$ alkyl group or moiety is generally a $C_{1-4}$ alkyl group or moiety such as methyl, ethyl, n-propyl, i-propyl, n-butyl and t-butyl. A $C_{3-10}$ alkyl group or moiety is typically a $C_{3-6}$ alkyl group or moiety, for example propyl, butyl, pentyl or hexyl. A $C_{0-2}$ alkyl group or moiety may be a bond, a methyl group or an ethyl group. An alkyl group may be unsubstituted or substituted by one to four substituents, the substituents, unless otherwise specified, being selected from Ra. Where two or more substituents are present, these may be the same or different.

Ra is —OH, —ORe, —NO$_2$, halogen, —S(O)Re, —S(O)$_2$Re, —SRe, —S(O)$_2$ORe, —S(O)NReRe —S(O)$_2$NReRe, —NReRe, —O(CReRe)$_m$NReRe, —C(O)Re, —CO$_2$Re, —CO$_2$(CReRe)$_m$CONReRe, —OC(O)Re, —CN, —C(O)NReRe, —NReC(O)Re, —OC(O)NReRe, —NReC(O)ORe, —ReC(O)NReRe, —CRe(N—ORe), —CFH$_2$, —CF$_2$H, or —CF$_3$; wherein Re is H or $C_{1-4}$alkyl and if two or more Re groups are present these may be the same or different.

An alkenyl group or moiety is a straight or branched group or moiety, which, unless otherwise specified, contains from 2 to 10 carbon atoms. One or more double bonds may be present in the alkenyl group or moiety, typically one double bond. A $C_{2-10}$ alkenyl group or moiety is typically ethenyl or a $C_{3-10}$ alkenyl group or moiety. A $C_{3-10}$ alkenyl group or moiety is typically a $C_{3-6}$ alkenyl group or moiety, for example propenyl, butenyl, pentenyl or hexenyl. A $C_{2-4}$ alkenyl group or moiety is ethenyl, propenyl or butenyl. An alkenyl group may be unsubstituted or substituted by one to four substituents, the substituents, unless otherwise specified, being selected from Ra. Where two or more substituents are present, these may be the same or different.

An alkynyl group or moiety is a straight or branched group or moiety which, unless otherwise specified, contains from 2 to 10 carbon atoms. One or more triple bonds, and optionally one or more double bonds may be present in the alkynyl group or moiety, typically one triple bond. A $C_{2-10}$ alkynyl group or moiety is typically ethynyl or a $C_{3-10}$ alkynyl group or moiety. A $C_{3-10}$ alkynyl group or moiety is typically a $C_{3-6}$ alkynyl group or moiety, for example propynyl, butynyl, pentynyl or hexynyl. A $C_{2-4}$ alkynyl group or moiety is ethynyl, propynyl or butynyl. An alkynyl group may be unsubstituted or substituted by one to four substituents, the substituents, unless otherwise specified, being selected from Ra. Where two or more substituents are present, these may be the same or different.

A cycloalkyl group or moiety is typically a 3- to 10-membered group or moiety, typically a 3- to 6-membered group or moiety, which may be a monocyclic ring or which may consist of two or more fused rings. Examples of cycloalkyl groups or moieties include cyclopropyl, cyclopentyl and cyclohexyl.

A heterocyclic group or moiety is an aromatic or a non-aromatic, saturated or unsaturated, 5- to 14-membered group or moiety. Typically it is a 5- to 11-membered group or moiety. More typically it is a 5- or 6-membered group or moiety, containing one or more heteroatoms, for example 1, 2 or 3 heteroatoms, selected from N, O and S. Typically it is unsaturated. A heterocyclic group or moiety may be a monocyclic ring or may consist of two or more fused rings, at least one of which contains a heteroatom selected from N, O and S. Examples of heterocyclic groups and moieties include pyridine, pyrimidine, pyridazine, pyrazine, quinoline, isoquinoline, phthalazine, quinoxaline, benzimidazole, 1H-indazole, 3H-indole, benzthiazole, indole, isoindole, cinnoline, quinazoline, 1,8-naphthyridine, pteridine, piperidyl, piperazinyl, azetidinyl, aziridyl, morpholinyl, thiomorpholinyl, imidazolidinyl, quinuclidinyl, thioxanyl, thiazolidinyl, tetrahydrofuranyl, tetrahydrothiophenyl, 1,3-dioxanyl, 1,4-dioxanyl, furan, thiophene, pyrrole, pyrazole, imidazole, benzothiophene, benzothiazole, benzofuran, isoxazole, oxazole, oxadiazole, indazole, thiazole, isothiazole, thiadiazole, dihydroimidizole, thianopyrazine, pyran, phthalimide, purine, triazine, triazole, tetrazole, chromene-4-thione, 1,3,4,5-tetramethyl-1,5-dihydro-pyrrol-2-one or uracil. A heterocyclic group may be unsubstituted or substituted with one or two substituents. Preferred substituents for a heterocyclic group or moiety generally include nitro, halogen, hydroxy, carboxyl, $CO_2$Re (typically $CO_2$Me), methyl and methoxy groups.

A carbocyclic group or moiety typically contains from 6 to 14 carbon atoms. More typically it contains 6 to 10 carbon atoms. It is aromatic or non-aromatic and saturated or unsaturated. It may be a monocyclic ring, for example phenyl, or, unless otherwise specified, may consist of two or more fused rings, for example naphthyl. A carbocyclic group or moiety is typically unsubstituted or substituted with one or two substituents. Preferred substituents for a carbocyclic group or moiety generally include nitro, halogen, hydroxy, carboxyl, $CO_2$Re (typically $CO_2$Me), —NH$_2$, —CHO, alkyl (typically methyl) and alkoxy (typically methoxy) groups.

A halogen is typically fluorine, chlorine or bromine.

In the complexes of the invention, M is a transition metal. The term "transition metal" as used herein means any one of the three series of elements arising from the filling of the 3d, 4d and 5d shells, and situated in the periodic table following the alkaline earth metals. This definition is used in N. N. Greenwood and A. Earnshaw "Chemistry of the Elements", First Edition 1984, Pergamon Press Ltd., at page 1060, first paragraph, with respect to the term "transition element". The same definition is used herein for the term "transition metal". Thus, the term "transition metal", as used herein, includes for instance Sc, Y, La, Ti, Zr, Hf, V, Nb, Ta, Cr, Mo, W, Mn, Tc, Re, Fe, Ru, Os, Co, Rh, Ir, Ni, Pd, Pt, Cu, Ag, Au, Zn, Cd and Hg. Accordingly, in the complexes of the invention, M is typically selected from Sc, Y, La, Ti, Zr, Hf, V, Nb, Ta, Cr, Mo, W, Mn, Tc, Re, Fe, Ru, Os, Co, Rh, Ir, Ni, Pd, Pt, Cu, Ag, Au, Zn, Cd and Hg. More typically, M is a first row transition metal. Thus, more typically, M is selected from Sc, Ti, V, Cr, Mn, Fe, Co, Ni, Cu and Zn. Even more typically, M is Ni, Cu or Zn.

When M is zinc, X and Y are typically selected from N and S.

In one embodiment, the present invention provides complexes of the invention as defined above which are fluorescent. In this embodiment, M is typically a transition metal in an oxidation state that results in electronic properties that do not quench fluorescence, such as $d^6$ or $d^{10}$. Examples include Zn(II), Cd(II), Re(I), Tc(I) and Ru(II). Theoretical investigations suggest that the fluorescence originates from transitions within the manifold orbitals solely involving the ligand. Thus, a range of bidentate ligands, and indeed thiosemicarbazone ligands with other denticities may be exhibit fluorescent activity. Typically in this embodiment, M is Zn or Cd. More typically, M is Zn.

The fluorescence of such complexes can be used to track their uptake in living cells and shows where the complexes are being localised. This may serve as a useful indication of the uptake mechanism that would be expected of the corresponding Cu complexes. However, this would not indicate the distribution in cells that would be expected of corresponding Cu complexes, as, unlike the zinc complexes, the latter are redox active (the tendency of a complex to dissociate is increased by oxidation or reduction of the metal atom). A significant feature of the fluorescent zinc complexes of the present invention is that they are fluorescent only when intact—dissociation causes loss of fluorescence as the free ligand does not fluoresce. It is also of note that the presence of the paramagnetic copper rules out the possibility of characterisation by nmr. Thus, it when intending to produce a copper complex, it can be helpful to first produce the corresponding metal complex with a non-paramagnetic species, before transmetallating in due course to replace the metal with copper.

In one embodiment the present invention provides fluorescent complexes that are taken up by a human cancer cell line. In this embodiment the fluorescence of the complexes allows the distribution of the complexes within the cells to be monitored.

The person of skill in the art will appreciate that depending on the metal present in the centre of a complex of the invention as defined above, it may be appropriate to have one or more further ligands bound to the central metal. For example, in one embodiment the present invention provides complexes as defined above wherein there is a fifth donor group that features in the group R5. In another embodiment, where necessary, the complex may also feature one or more further ligands. Additional ligands can be neutral or anionic and can be any suitable small molecule. Typical examples include halogen and water. For example, when M represents Zn(II), then typically a fifth apical ligand, such as chloride, methanol, water or (O-bound) DMSO, is present. The $d^{10}$ configuration of zinc does not confer stabilisation energy to any particular geometry, and instead the conformation adopted by zinc in its complexes is a function of the steric and conformational demands of the ligands. Considering, on the other hand, copper and nickel, both of these show a preference for tetradentate planar complexes.

The present inventors have also discovered that the Zn complexes can be modified to make them 2 photon fluorophores. This means that excitation can be carried out at around 800 nm rather than at around 400 nm. This has the advantage that tissue is more transparent to radiation at the former wavelength. Thus, in one embodiment the present invention provides Zn complexes which are 2 photon fluorophores. Longer wavelength, lower energy fluorescence is desirable because it decreases scattering (and therefore increased resolution) and minimises damage to biological tissue. Further, the use of a metastable metal radionuclide has the potential to allow both SPECT and PET imaging (Section 1.3), which if combined with fluorescence imaging could provide an extremely powerful tool in the clinical diagnosis and treatment of disease.

On the other hand, some complexes of the present invention show fluorescence in the range 500-600 nm (depending on the ligand and solvent, as described by Cowley et al in *Chem. Commun.* 2005, 7, 845). This fluorescence profile can also be advantageous, particularly for in vitro studies, as allows for a relatively low energy excitation that reduces potential interference from other fluorescent molecules in the cell, such as DNA. Fluorescence measurements of the uptake and distribution of zinc bis(thiosemicarbazones) in cancer cells show that the integrity of the complexes is maintained; control experiments involving the addition of a zinc salt or bis(thiosemicarbazone) ligand alone show no fluorescence above the low intensity background. The uptake and distribution is a function of both the nature of the R2 and L1R1 (and R2' and L1'R1') substituents on the bis(thiosemicarbazone) ligand and the cell type.

In one embodiment the present invention provides complexes which are water soluble. In another embodiment, the present invention provides complexes which are more soluble in non-polar organic solvents. Control of this aspect of the complex can be achieved by manipulation of the —N(R2)-L1-R1 and —N(R2')-L1'-R1' groups. For example, where a water soluble complex is desired, these groups can be chosen such that the complex has one or more sugar moieties attached. On the other hand, high solubility in non-polar organic solvents can be conferred by selecting these groups to include one or more long chain aliphatic groups, such as a $C_6$-$C_{20}$ alkyl group.

In the complexes of the invention as defined above, it is to be understood that each R3 is independently selected from H, $C_1$-$C_6$ alkyl, heterocyclic group and phenyl, so that each R3 may be the same as or different from the other R3 groups in a given complex. Similarly, it is to be understood that each R4 is independently selected from H, $C_1$-$C_6$ alkyl, heterocyclic group and phenyl, so that each R4 may be the same as or different from the other R4 groups in a given complex. Similarly, it is to be understood that each R10 is independently selected from H, $C_1$-$C_6$ alkyl, heterocyclic group and phenyl, so that each R10 may be the same as or different from the other R10 groups in a given complex. The same applies to R5 when more than one R5 is present in a given complex.

In the complexes of the invention as defined above, it is to be understood that each of the linker groups, L1, L1' and L3 can be arranged either way around, i.e. head-to-tail or tail-to-head, when linking two groups together. Thus, for example, the linking group -alk-S(O)$_2$NR$_7$— may link the R1 and N groups together in either of the following arrangements: N-alk-S(O)$_2$NR$_7$—R1 and N—NR$_7$S(O)$_2$-alk-R1.

In the complexes of the invention as defined above, typically, each R3 is independently selected from H, $C_1$-$C_6$ alkyl and phenyl. More typically, each R3 is independently selected from H and $C_1$-$C_4$ alkyl. More typically still, each R3 is independently selected from H and methyl. In one embodiment, A1 is option (a) and each R3 is methyl. Typically, each R3 group is the same.

Typically, each R4 is independently selected from H, $C_1$-$C_6$ alkyl and phenyl. More typically, each R4 is independently selected from H and $C_1$-$C_4$ alkyl. More typically still, each R3 is independently selected from H and methyl.

Typically, M2 in the group V is a group I or group II metal or a transition metal. More typically, it is a transition metal. P2 and Q2 in the group V are typically selected from N, O and S. More typically, they are selected from N and S. Appropriate selection of M2 (bearing in mind P2 and Q2) allows the stereochemistry of the —V— link to be adjusted and controlled. In one embodiment, M2 is coordinated by the P2 and Q2 groups in a square planar arrangement. In another embodiment, M2 is coordinated by the P2 and Q2 groups in a tetrahedral arrangement. Typically, when R1 (or R1') includes the group —V—, the group Z is a metal complex of a bis(thiosemicarbazone) or of a thiosemicarbazone, thereby creating a dimer wherein two bis(thiosemicarbazone) or thiosemicarbazone complexes are linked by -L1-R1-L1—, -L1-alk-R1-L1—, -L1-R1-alk-L1- or -L1-alk-R1-alk-L1- wherein L1 and R1 are as defined above. In this embodiment, appropriate selection of M2, P2 and Q2 in the group —V— also allows adjustment and control of the electronic connection between the metal centres. The resulting arrays may provide an opportunity to modulate the photophysical, magnetic and spectroscopic properties of the resulting dimers. When M2 is zinc, P2 and Q2 are typically selected from N and S.

Typically each R10 is independently selected from H, $C_1$-$C_6$ alkyl and phenyl. More typically, each R10 is independently selected from H and $C_1$-$C_4$ alkyl. More typically still, each R10 is independently selected from H and methyl. Most typically, each R10 is hydrogen.

Typically, when X and X' are both N, Y is S, A1 is (a') and A2 is (d) then either R1 or R1' is Z, L3-Z, L3-alk-Z, —V-L3-Z, —V-L3-alk-Z, -alk-V-L3-Z, -alk-V-L3-alk-Z or a group selected from an alkyl, amino, carbocyclic, cycloalkyl, heterocyclic, -alk-carbocyclic, -alk-cycloalkyl and -alk-heterocyclic group, which group is further substituted by L3-Z or L3-alk-Z.

In the complexes of the invention as defined above, it is preferred that either:
A2, X and Y are as defined in (ii) or (iii);
A2, X any Y are as defined in (i) wherein A2 is (e); or
either R1 or R1' is Z, L3-Z, L3-alk-Z, —V-L3-Z, —V-L3-alk-Z, -alk-V-L3-Z, -alk-V-L3-alk-Z or a group selected from an alkyl, amino, carbocyclic, cycloalkyl, heterocyclic, -alk-carbocyclic, -alk-cycloalkyl and -alk-heterocyclic group, which group is further substituted by L3-Z or L3-alk-Z.

Typically, in the complexes of the invention, either the moiety represented by L1-R1 or the moiety represented by L1'-R1' is other than H, unsubstituted alkyl or unsubstituted alkoxy.

Typically in the complexes of the present invention n is 0, so that A1, X, X' and M together form a five-membered metallocyclic ring. Alternatively, however, n may be an integer from 1 to 5 so that the A1 backbone is longer. Increasing the length of the A1 backbone in this way has been found to increase the ability of the complexes of the present invention to deviate from a geometry in which the X', X, S and Y donor atoms are in square-planar arrangement. For example, it has been found that when n is 2, a tetrahedral geometry is favoured by the X', X, S and Y donor atoms. Where n is an integer of 1 to 5 it is preferred that n is either 1, 2 or 3, and it is more preferred that n is 2. Typically A1 is either (a'), (b'), (d') or (e') and n is 1, 2, 3, 4 or 5. More typically, A1 is either (a'), (b'), (d') or (e') and n is 2. Even more typically, A1 is either (a') or (d') and n is 2.

In one embodiment of the complexes of the present invention, A1 is (d'). Preferably, in this embodiment n is 0. Preferably X and X' are each N(R5). Preferably R5 is H, methyl or ethyl. The use of a backbone in which A1 is linked to X by a single bond and A1 is linked to X' by a single bond has been found to increase the stability of the complex compared to complexes in which A1 is linked to both X and X' via double bonds.

Typically in the complexes of the invention X is N when A1 is attached to X via a double bond and X is N(R5) when A1 is attached to X via a single bond. Typically, X' is N when A1 is attached to X' via a double bond and X' is N(R5) when A1 is attached to X' via a single bond.

Typically in the complexes of the present invention A1 is either (a'), (b') or (c') and X' is N. Typically n is 0 or 2.

In one embodiment of the complexes of the present invention, when A1 is (a'), n is 0 or 1.

Typically, neither or only one of R1 and R1' features a Z group. In one embodiment, neither R1 nor R1' features a Z group. In another embodiment, one of R1 and R1' features a Z group.

When Z is a fluorophore, this group may be any group, part or all of which can be excited by radiation to fluorescence. In one embodiment, the fluorophore is a zinc bis(thiosemicarbazone) complex. In another embodiment, the fluorophore is a 2-(4-aminophenyl)benzothiazole or derivative thereof. Examples of such suitable derivatives include those in the table below.

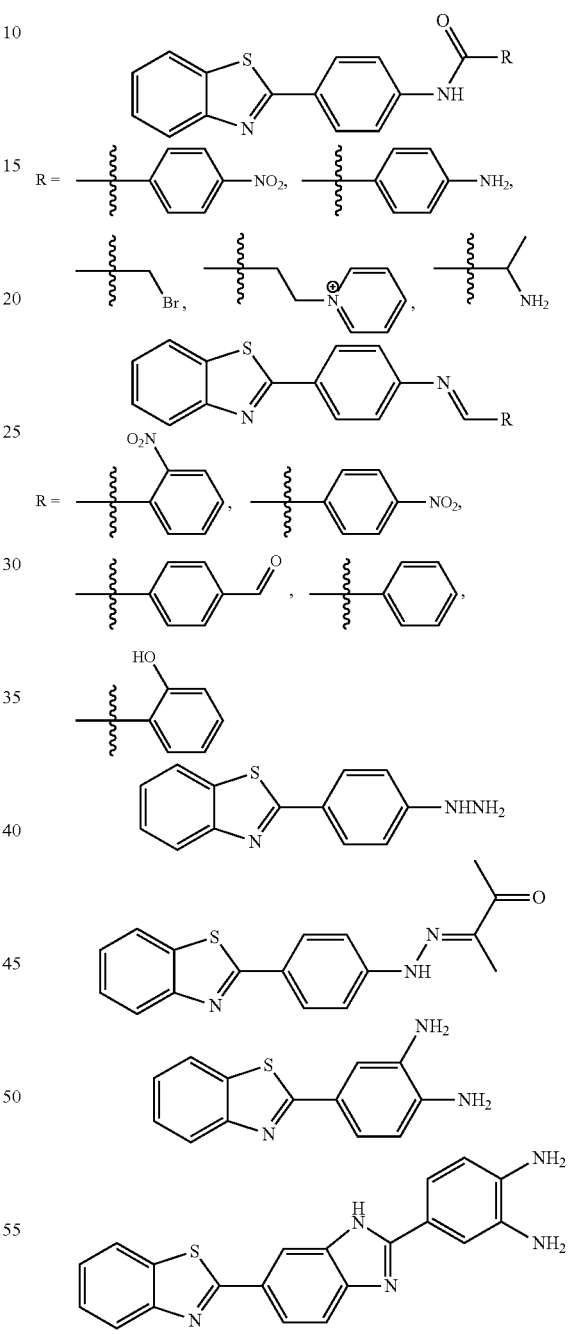

Complexes of formula (III) which incorporate a fluorophore Z may be synthesised by reaction of a fluorophore containing an aldehyde, ketone, carboxylic acid or acid halide fluorophore with a precursor complex containing an amino group. The precursor complex may be a complex of formula (III) in which R1 or R1' contains an amino group, such as M[ATSM/A] or M[ATSP/A]. The fluorophore for reaction with the amino group may be benzaldehyde, 2-furaldehyde, salicylaldehyde, hydroxynaphthaldehyde, 4-(di-n-propylamino) benzaldehyde, butane-2-3-dione, phenyl glyoxal, terephthalaldehyde, glyoxal, isophthaldehyde, pyruric acid, propionaldehyde, 4-fluorobenzaldehyde, 2-pyridinecarboxaldehyde, Zn[ATSM/A-terephthalaldehyde], Zn[ATSM/A-glyoxal], Zn[ATSM/A-terephthaloyl chloride] and Zn[ATSM/A-isophthalaldehyde]. Thus, fluorophore Z may be derived from any of the compounds in the preceding list.

When Z is a group containing a label, the label can be any moiety that permits the detection of the complex. The label may be a fluorophore, for instance as described above. Typically it is a radioisotope. Examples include $^{18}F$, $^{11}C$, $^{14}C$, $^{3}H$, $^{99m}Tc$, $^{111}In$, $^{123}I$ and $^{188}Re$. In another embodiment it may be a stable isotope. Examples include $^{13}C$, $^{2}H$ and $^{15}N$. In one preferred embodiment it is a label that decays via positron emission, beta emission, electron capture or Auger emissions. More typically, the label decays by positron emission. Most typically the label is $^{18}F$. When the label is $^{18}F$, because of the short half-life of $^{18}F$ (110 minutes), the fluorinated derivative must be prepared on the day of its clinical use and the reaction steps used to produce it should be optimised for speed, with yield as a secondary consideration. $^{18}F$ is typically prepared from a cyclotron in the form of $KH^{18}F_2$ and the $^{18}F$ in $KH^{18}F_2$ replaces a suitable leaving group in the complex with $^{18}F$. Examples of suitable leaving groups include imidazosulfonyl, triflate, mesylate and tosylate. Accordingly, in a preferred embodiment of the present invention, the group Z in the complex of the invention as defined above may represent such a suitable leaving group. Images may be acquired from about 5 minutes after administration until about 8 hours after administration. The maximum period in which images may be acquired is determined by 3 factors: the physical half-life of $^{18}F$ (110 minutes); the sensitivity of the detectors and the size of the dose administered. Those of skill in the art can adjust these factors to permit the acquisition of images at an appropriate time. Details of imaging procedures are well known.

Radionuclides which emit gamma radiation can be used for SPECT imaging. SPECT scanners are gamma cameras which detect the photons produced from this decay. Facilities for SPECT imaging are widely available in hospitals. Radionuclides suitable for PET imaging must undergo $\beta^+$ decay, in which the nucleus emits a positron and neutrino. When the positron encounters an electron the two annihilate and two gamma rays are emitted. These travel in opposite directions (in reality at an angle of 179.5° due to the residual momentum of the positron.) The encircling PET scanner simultaneously detects these photons. This technique has significantly reduced noise, higher sensitivity and has a superior resolution to SPECT, however PET scanners are less widely available than those used for SPECT. In one embodiment the present invention provide diagnostic agents comprising a complex of the invention as defined above, for use in SPECT imaging.

When Z is a cytotoxin it is, for instance, an agent which is cytotoxic to cancer cells. Examples of such cytotoxins include taxanes such as taxol and taxotere; Vinca alkaloids such as vincristine and vinblastine; anthracycline antibiotics such as daunorubicin, epirubicin and doxorubicin; epipodophyllotoxins such as etoposide and plicamycin; mitoxantrone; and actinomycin D.

When Z is an amino acid, a peptide, an oligopeptide or a polypeptide, any amino acid or combination of amino acids may be used. Z may be any amino acid, derivative thereof or combinations (in the form of a straight or branched chain) thereof. Examples include —Lys(Boc)-OH, -Orn(Boc)-OH, -Lys-OH and -ocreotide. Z may be —ONSu, derived from N-hydroxysuccinimide.

When Z is a sugar moiety, it can be a monosaccharide, disaccharide or trisaccharide. It can, for example, be glucose, sucrose or lactose.

When Z is a bis(thiosemicarbazone) or thiosemicarbazone Cu or Zn complex, typically it is a bis(thiosemicarbazone) Cu or Zn complex. More typically it is a Zn complex.

Typically in this embodiment the group Z is only present in one of R1 and R1', resulting in a compound with two bis(thiosemicarbazone) complexes joined by a linker group. In this embodiment, both of the metal atoms present are typically Zn, thus creating a bi-nuclear zinc complex. Linking two zinc centres in this way can have a significant effect on the fluorescence properties as compared to the properties of a mono-nuclear zinc complex. This is discussed further below.

The linking of two zinc centres may also lead to complexes with significantly different biological activities as compared to the mono-nuclear complexes. Interest in binuclear complexes is two fold. Fundamentally, the presence of two metal centres close to one another can induce interactions that can influence the complex's magnetic or redox properties, useful in the development of two centred metal catalytic reagents. The communication between the two metals may be electronic (direct interaction or delocalization through a bridging coordinating unit) and/or electrostatic, although the separation of the two contributions may not be straightforward (see Ciampolini, M.; Micheloni, M.; Nardi, N.; Vizza, F.; Buttafava, A.; Fabbrizzi, L.; Perotti, A. *J. Chem. Soc., Chem. Commun.* 1984, 998). Moreover, binuclear centres containing transition elements are ubiquitous in metalloproteins and enzymes. Superoxide dismutase contains an imidazolate-bridged Cu—Zn binuclear metal centre in its active site, the active site of alkaline phosphatase contains a zinc ion and a magnesium ion and the oxygen carrying protein haemerythrin has an Fe—O—Fe centre. Binuclear complexes of chelating and macrocyclic ligands may therefore serve as models for the charge transfer, electron transport, and allosteric behaviour found in many metal-containing biochemical systems (see Soibinet, M.; Dechampes-Olivier, I.; Guillon, E.; Barbier, J.-P.; Aplincourt, M.; Chuburu, F.; Le Baccon, M.; Handel, H. *Eur. J. Inorg. Chem.* 2003, 1984.). Efforts have been made to make complexes of macrocyclic and chelating ligands linked by rigid spacers, which can be used as models to investigate the reactivity changes caused by the proximity of the two metals and to understand the reactivity of metalloenzymes which require two metal centres located at specific distances to accomplish their biological function.

In one embodiment, the present invention provides complexes of formula (III) as defined above, wherein M is copper and Z represents a second bis(thiosemicarbazone) complex containing zinc, thus providing a radiopharmaceutical complex tethered to a fluorescent complex.

It is unlikely that it will be possible to decouple the interaction between the two metal centres in a binuclear complex. In order to maintain planarity in the structure as a whole, thus allowing comparatively easy diffusion in and out of cells, it will be necessary to link the bis(thiosemicarbazone) units through a rigid spacer. This offers the possibility of electronic interaction between the two metal centres via the $\pi$ system. Similarly, in systems linked by sufficiently long non-rigid spacers, conformational flexibility will allow the bis(thiosemicarbazone) units to adopt a face to face arrangement, which may facilitate cooperation between the two centres.

In one embodiment of the invention, the complex is of formula (III) as defined above wherein:

A1, X, X', Y and R2' are as defined above;
M is Cu, Zn or Ni;
L1' is a covalent bond;
R1' is H or a group selected from alkyl, alkoxy and phenyl; and A2 is of formula (d) as defined above, or A2 and Y together represent a group of formula (B) as defined above and wherein, in formulae (d) and (B), L1 is as defined above and R1 is Z, L3-Z, L3-alk-Z or a group substituted by L3-Z or L3-alk-Z, wherein said group, L3 and Z are as defined above.

In a further embodiment of the invention, the complex is of formula (III) as defined above wherein:

M is Cu;
X is N;
A1 is a group of formula (a') as defined above;
A2 and Y together represent a group of formula (C):

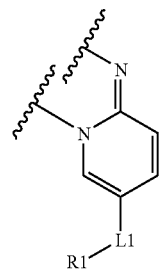

(C)

in which L1 and R1 are as defined above;
L1' is a covalent bond;
R1' is H or a group selected from alkyl, alkoxy and phenyl; and
R2' is as defined above.

In another embodiment of formula (I), Z is a Cu or Zn complex of a bis(thiosemicarbazone) or of a thiosemicarbazone, thereby creating a dimer wherein two bis(thiosemicarbazone) or thiosemicarbazone Cu or Zn complexes are linked by -L1-R1-L1—, -L1-alk-R1-L1—, -L1-R1-alk-L1- or -L1-alk-R1-alk-L1- wherein L1 and R1 are as defined above. Preferably X' is N. Preferably n is 0.

Typically, the complex of the invention is a metal complex of formula (III'):

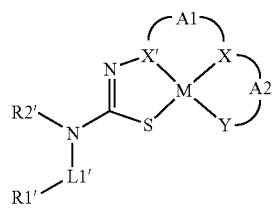

(III')

wherein:
M is a transition metal;
A1 is:

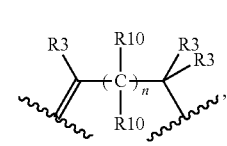

(b')

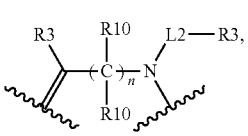

(c')

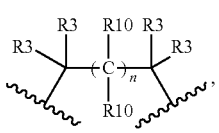

(d')

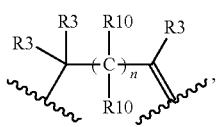

(e')

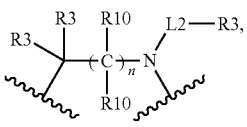

(f')

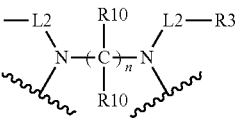

(g')

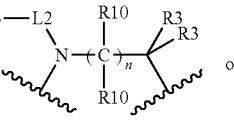

(h')

or

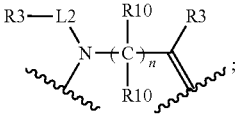

(i')

n is 0 or an integer of 1 to 5;
A2 is

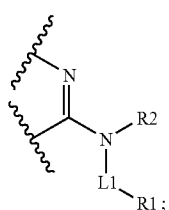

(d)

X is N or P and A1 is attached to X via a double bond, or X is O, S, N(R5) or P(R5) and A1 is attached to X via a single bond;
Y is N, O, P, S, N(R5), O(R5), P(R5) or S(R5);

X' is N and A1 is attached to X' via a double bond, or X' is N(R5), O, S or P(R5) and A1 is attached to X' via a single bond;

L1 and L1', which are the same or different, are each independently selected from a covalent bond and a linker group selected from —C(O)—, -alk-C(O)—, —C(O)O—, -alk-C(O)O—, —OC(O)—, -alk-OC(O)—, —O—, -alk-O—, —N(R7)—, -alk-N(R7)—, —N(R7)C(O), -alk-N(R7)C(O)—, —C(O)N(R7), -alk-C(O)N(R7), —C(S)—, -alk-C(S)—, —S—, -alk-S—, —C(S)N(R7)—, -alk-C(S)N(R7)—, —N(R7)C(S)—, -alk-N(R7)C(S)—, —S(O)$_2$N(R7)—, -alk-S(O)$_2$N(R7)—, —N(R7)S(O)$_2$—, -alk-N(R7)S(O)$_2$—, —S(O)—, -alk-S(O)—, —N(R7)C(O)O—, -alk-N(R7)C(O)O—, —OC(O)N(R7)—, -alk-OC(O)N(R7)—, —N(R7)C(O)N(R7)—, -alk-N(R7)C(O)N(R7)—, —N(R7)C(S)N(R7)—, -alk-N(R7)C(S)N(R7)—, —N=C(R7)—, -alk-N=C(R7)—, —C(R7)=N— and -alk-C(R7)=N—;

R1 and R1', which are the same or different, are each independently selected from hydrogen, Z, L3-Z, L3-alk-Z, —V-L3-Z, —V-L3-alk-Z, alk-V-L3-Z, -alk-V-L3-alk-Z and a substituted or unsubstituted group selected from an alkyl, amino, carbocyclic, cycloalkyl, heterocyclic, -alk-carbocyclic, -alk-cycloalkyl and -alk-heterocyclic group, which group may be further substituted by L3-Z or L3-alk-Z, wherein L3 is as defined above for L1 and L1', —V— is a linking group of the following formula:

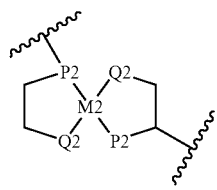

wherein P2 and Q2 are independently selected from N, O, P and S and M2 is a metal atom, and Z is a moiety selected from a biologically active molecule, a fluorophore, a cytotoxin, an amino acid, a peptide, an oligopeptide, a polypeptide, a sugar, a group containing a label, a leaving group which is replaceable by a group containing a label, and a complex of Cu, Zn or Ni with a bis(thiosemicarbazone) or a thiosemicarbazone;

-alk- is an alkylene, alkenylene or alkynylene group based on an alkyl, alkenyl or alkynyl group;

R2 and R2', which are the same or different, are each independently selected from H, C$_1$-C$_6$ alkyl and C$_1$-C$_6$ alkoxy;

each R3 is independently selected from H, C$_1$-C$_6$ alkyl, heterocyclic group and phenyl;

each R5 is independently selected from H, C$_1$-C$_6$ alkyl and a group comprising an electron donor group, which donor group is separated by two carbon atoms from the O, N, S or P atom to which R5 is attached;

R7 is H, alkyl or cycloalkyl;

each R10 is independently selected from H, C$_1$-C$_6$ alkyl, heterocyclic group and phenyl; and L2 is —C(O)— or a covalent bond.

Typically, in this embodiment, either the moiety represented by L1-R1 or the moiety represented by L1'—R1' is other than H, unsubstituted alkyl or unsubstituted alkoxy.

Alternatively, the complex of the invention is a metal complex of formula (III"):

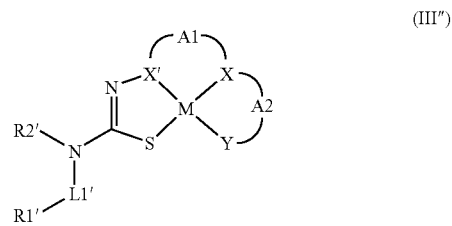

wherein:

M is a transition metal;

A1 is:

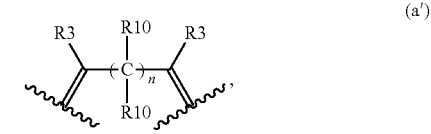

(a')

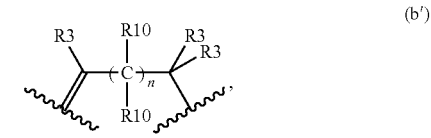

(b')

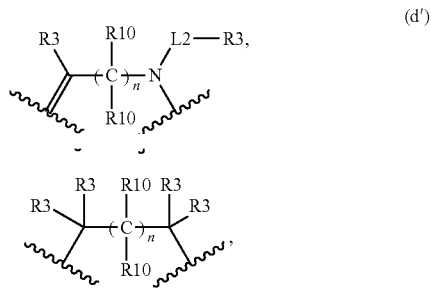

(d')

(e')

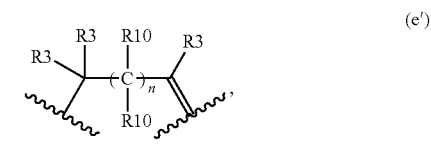

(f')

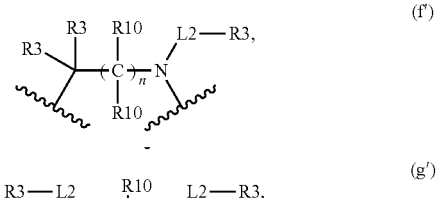

(g')

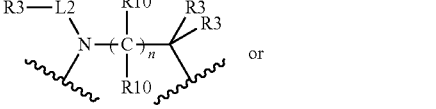

(h')

or

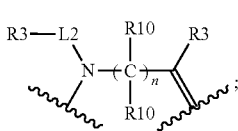

n is 0 or an integer of 1 to 5;
A2, X and Y are as defined in (i), (ii) and (iii) which follow:
(i) A2 is

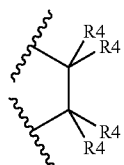

X is N or P and A1 is attached to X via a double bond, or X is O, S, N(R5) or P(R5) and A1 is attached to X via a single bond; and Y is N, O, P, S, N(R5), O(R5), P(R5) or S(R5); or
(ii) X is N or P and A1 is attached to X via a double bond, or X is O, S, N(R5) or P(R5) and A1 is attached to X via a single bond; and Y and A2 together represent a moiety of formula (B):

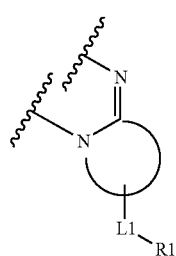

wherein the ring that is substituted by L1-R1 is a 5- to 11-membered heterocyclic group; or
(iii) X, A2 and Y together represent

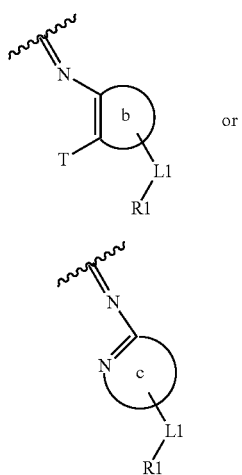

wherein T is OH, O—, COOH or C(O)O— and rings b and c are aromatic $C_{6-10}$ carbocyclic or 5 to 11 membered aromatic heterocyclic groups;

X' is N and A1 is attached to X' via a double bond, or X' is N(R5), O, S or P(R5) and A1 is attached to X' via a single bond;

L1 and L1', which are the same or different, are each independently selected from a covalent bond and a linker group selected from —C(O)—, -alk-C(O)—, —C(O)O—, -alk-C(O)O—, —OC(O)—, -alk-OC(O)—, —O—, -alk-O—, —N(R7)—, -alk-N(R7)—, —N(R7)C(O), -alk-N(R7)C(O)—, —C(O)N(R7), -alk-C(O)N(R7), —C(S)—, -alk-C(S)—, —S—, -alk-S—, —C(S)N(R7)—, -alk-C(S)N(R7)—, —N(R7)C(S)—, -alk-N(R7)C(S)—, —S(O)$_2$N(R7)—, -alk-S(O)$_2$N(R7)—, —N(R7)S(O)$_2$—, -alk-N(R7)S(O)$_2$—, —S(O)—, -alk-S(O)—, —N(R7)C(O)O—, -alk-N(R7)C(O)O—, —OC(O)N(R7)—, -alk-OC(O)N(R7)—, —N(R7)C(O)N(R7)—, -alk-N(R7)C(O)N(R7)—, —N(R7)C(S)N(R7)—, -alk-N(R7)C(S)N(R7)—, —N=C(R7)—, -alk-N=C(R7)—, —C(R7)=N— and -alk-C(R7)=N—;

R1 and R1', which are the same or different, are each independently selected from hydrogen, Z, L3-Z, L3-alk-Z, —V-L3-Z, —V-L3-alk-Z, alk-V-L3-Z, -alk-V-L3-alk-Z and a substituted or unsubstituted group selected from an alkyl, amino, carbocyclic, cycloalkyl, heterocyclic, -alk-carbocyclic, -alk-cycloalkyl and -alk-heterocyclic group, which group may be further substituted by L3-Z or L3-alk-Z, wherein L3 is as defined above for L1 and L1', —V— is a linking group of the following formula:

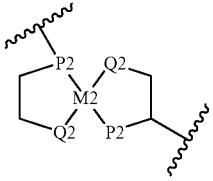

wherein P2 and Q2 are independently selected from N, O, P and S and M2 is a metal atom, and Z is a moiety selected from a biologically active molecule, a fluorophore, a cytotoxin, an amino acid, a peptide, an oligopeptide, a polypeptide, a sugar, a group containing a label, a leaving group which is replaceable by a group containing a label, and a complex of Cu, Zn or Ni with a bis(thiosemicarbazone) or a thiosemicarbazone;

-alk- is an alkylene, alkenylene or alkynylene group based on an alkyl, alkenyl or alkynyl group;

R2' is selected from H, $C_1$-$C_6$ alkyl and $C_1$-$C_6$ alkoxy;

each R3 is independently selected from H, $C_1$-$C_6$ alkyl, heterocyclic group and phenyl;

each R4 is independently selected from H, $C_1$-$C_6$ alkyl, heterocyclic group and phenyl;

each R5 is independently selected from H, $C_1$-$C_6$ alkyl and a group comprising an electron donor group, which donor group is separated by two carbon atoms from the O, N, S or P atom to which R5 is attached;

R7 is H, alkyl or cycloalkyl;

each R10 is independently selected from H, $C_1$-$C_6$ alkyl, heterocyclic group and phenyl; and L2 is —C(O)— or a covalent bond.

Typically, in this embodiment, either the moiety represented by L1-R1 or the moiety represented by L1'-R1' is other than H, unsubstituted alkyl or unsubstituted alkoxy.

The complex of the invention may be a metal complex of formula (IIIa):

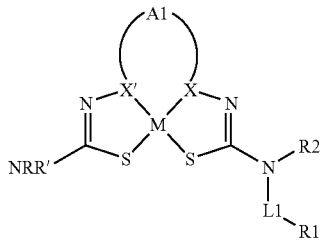

(IIIa)

wherein:
M is Cu, Zn or Ni;
A1 is:

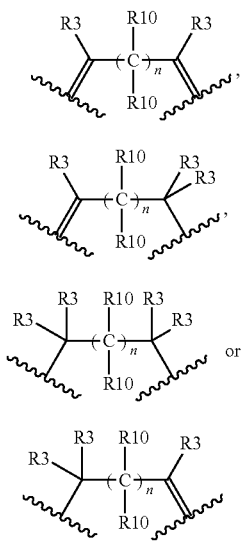

X is N and A1 is attached to X via a double bond, or X is N(R11) and A1 is attached to X via a single bond;

X' is N and A1 is attached to X' via a double bond, or X' is N(R11) and A1 is attached to X' via a single bond;

n is O or an integer of 1 to 5;

each R11 is independently selected from H and $C_1$-$C_6$ alkyl;

each R10 is independently selected from H, $C_1$-$C_6$ alkyl and phenyl;

R and R', which are the same or different, are each H or a group selected from $C_1$-$C_6$ alkyl, $C_1$-$C_6$ alkoxy and phenyl;

R2 is H or a group selected from $C_1$-$C_6$ alkyl and $C_1$-$C_6$ alkoxy;

each R3, which are the same or different, is H or a group selected from $C_1$-$C_6$ alkyl and phenyl;

L1 is a covalent bond or a linker group selected from —C(O)—, -alk-C(O)—, —C(O)O—, -alk-C(O)O—, —OC(O)—, -alk-OC(O)—, —O—, -alk-O—, —N(R7)—, -alk-N(R7)—, —N(R7)C(O), -alk-N(R7)C(O)—, —C(O)N(R7), -alk-C(O)N(R7), —C(S)—, -alk-C(S)—, —S—, -alk-S—, —C(S)N(R7)—, -alk-C(S)N(R7)—, —N(R7)C(S)—, -alk-N(R7)C(S)—, —S(O)$_2$N(R7)—, -alk-S(O)$_2$N(R7)—, —N(R7)S(O)$_2$—, -alk-N(R7)S(O)$_2$—, —S(O)—, -alk-S(O)—, —N(R7)C(O)O—, -alk-N(R7)C(O)O—, —OC(O)N(R7)—, -alk-OC(O)N(R7)—, —N(R7)C(O)N(R7)—, -alk-N(R7)C(O)N(R7)—, —N(R7)C(S)N(R7)—, -alk-N(R7)C(S)N(R7)—, —N=C(R7)—, -alk-N=C(R7)—, —C(R7)=N— and -alk-C(R7)=N—; R7 is H, alkyl or cycloalkyl; and R1 is Z, L3-Z, -alk-L3-Z or a group selected from an alkyl, carbocyclic, cycloalkyl, heterocyclic, -alk-carbocyclic, -alk-cycloalkyl and -alk-heterocyclic group, which group is further substituted by L3-Z or L3-alk-Z, wherein L3 is as defined above for L1 and Z is a moiety selected from a biologically active molecule, a fluorophore, a cytotoxin, an amino acid, a peptide, an oligopeptide, a polypeptide, a group containing a label, a leaving group which is replaceable by a group containing a label, and a Cu or Zn complex of a bis(thiosemicarbazone) or of a thiosemicarbazone.

Preferably, A1 is either (a') or (d') and n is either 0 or 2. More preferably, A1 is (a') and n is O. Even more preferably the complex of the invention is of formula (Ia):

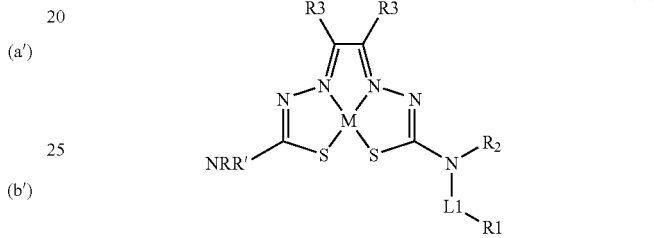

(Ia)

wherein:
M is Cu, Zn or Ni;
R and R', which are the same or different, are each H or a group selected from $C_1$-$C_6$ alkyl, $C_1$-$C_6$ alkoxy and phenyl;

R2 is H or a group selected from $C_1$-$C_6$ alkyl and $C_1$-$C_6$ alkoxy;

each R3, which are the same or different, is H or a group selected from $C_1$-$C_6$ alkyl and phenyl;

L1 is a covalent bond or a linker group selected from —C(O)—, -alk-C(O)—, —C(O)O—, -alk-C(O)O—, —OC(O)—, -alk-OC(O)—, —O—, -alk-O—, —N(R7)—, -alk-N(R7)—, —N(R7)C(O), -alk-N(R7)C(O)—, —C(O)N(R7), -alk-C(O)N(R7), —C(S)—, -alk-C(S)—, —S—, -alk-S—, —C(S)N(R7)—, -alk-C(S)N(R7)—, —N(R7)C(S)—, -alk-N(R7)C(S)—, —S(O)$_2$N(R7)—, -alk-S(O)$_2$N(R7)—, —N(R7)S(O)$_2$—, -alk-N(R7)S(O)$_2$—, —S(O)—, -alk-S(O)—, —N(R7)C(O)O—, -alk-N(R7)C(O)O—, —OC(O)N(R7)—, -alk-OC(O)N(R7)—, —N(R7)C(O)N(R7)—, -alk-N(R7)C(O)N(R7)—, —N(R7)C(S)N(R7)—, -alk-N(R7)C(S)N(R7)—, —N=C(R7)—, -alk-N=C(R7)—, —C(R7)=N— and -alk-C(R7)=N—; and R1 is Z or a group selected from an alkyl, carbocyclic, cycloalkyl, heterocyclic, -alk-carbocyclic, -alk-cycloalkyl and -alk-heterocyclic group, which group is further substituted by L3-Z or L3-alk-Z, wherein L3 is as defined above for L1 and Z is a moiety selected from a biologically active molecule, a fluorophore, a cytotoxin, an amino acid, a peptide, an oligopeptide, a polypeptide, a group containing a label, a leaving group which is replaceable by a group containing a label, and a Cu or Zn complex of a bis(thiosemicarbazone) or of a thiosemicarbazone.

In one embodiment of formula (IIIa) or (Ia):
R2 is H;
each R3 is methyl;
L1 is a covalent bond, —NR7—, —N=C(R7)—, —C(R7)=N(R7)—, —N(R7)C(O)— or —C(O)N(R7)- wherein R7 is as defined above for formula (IIIa) or (Ia); and R1, R' and R' are as defined above for formula (IIIa) or (Ia).

In a further embodiment the complex of the invention is of formula (IIIb):

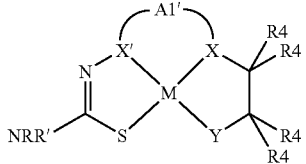
(IIIb)

wherein

M is Cu, Zn or Ni;

R and R', which are the same or different, are each H or a group selected from $C_1$-$C_6$ alkyl, $C_1$-$C_6$ alkoxy and phenyl;

A1' is a group of formula (a'), (b'), (c'), (d'), (e'), (f'), (g'), (h') or (i'):

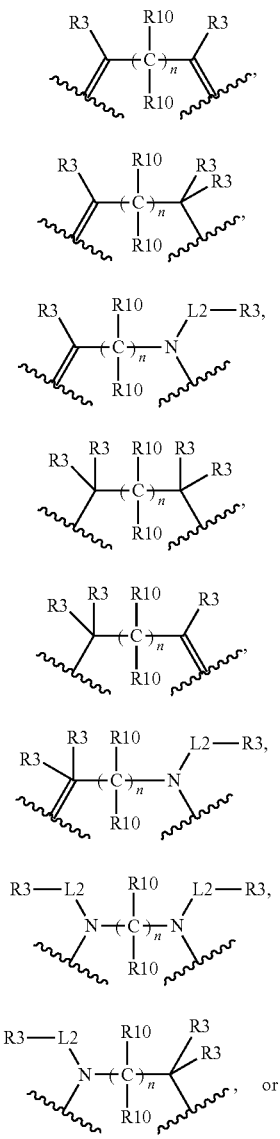

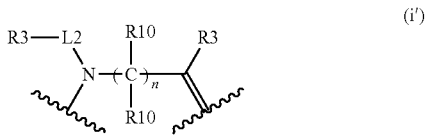

wherein each R3, which are the same or different, is H or a group selected from $C_1$-$C_6$ alkyl and phenyl; each L2 is independently selected from —C(O)— and a covalent bond; each R10 is independently selected from H, $C_1$-$C_6$ alkyl and phenyl; and n is 0 or an integer of 1 to 5;

each R4, which are the same or different, is independently selected from H, $C_1$-$C_6$ alkyl and phenyl;

X is N or P and A1' is attached to X via a double bond, or X is selected from O, S, N(R5) and P(R5) and A1' is attached to X via a single bond;

Y is selected from O, S, N(R5), P(R5), O(R5) and S(R5); and each R5 is independently selected from H, $C_1$-$C_6$ alkyl and a group comprising an electron donor group, which donor group is separated by two carbon atoms from the O, N, S or P atom to which R5 is attached.

Typically, A' is either (a') or (d') and n is either 0 or 2. Alternatively, A1' is either (a'), (b') or (c') and n is 0. Even more typically, the complex is of formula (Ib):

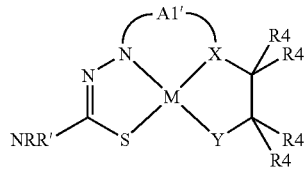
(Ib)

wherein

M is Cu, Ni or Zn;

R and R', which are the same or different, are each H or a group selected from $C_1$-$C_6$ alkyl, $C_1$-$C_6$ alkoxy and phenyl;

A1' is a group of formula (a), (b) or (c):

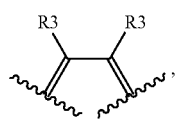
(a)

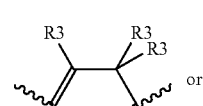
(b)

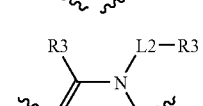
(c)

wherein each R3, which are the same or different, is independently selected from H, $C_1$-$C_6$ alkyl and phenyl;

X is N or P and A1' is attached to X via a double bond, or X is selected from O, S, N(R5) and P(R5) and A1' is attached to X via a single bond;

Y is selected from O, S, N(R5), P(R5), O(R5) and S(R5); and

R5 is a group comprising an electron donor group, which donor group is separated by two carbon atoms from the O, N, S or P atom to which R5 is attached.

Typically in formula (IIIb) or (Ib), at least one R4 on each carbon atom bearing two R4 groups is H.

In a further embodiment the present invention provides a bi-nuclear complex of formula (Ic)

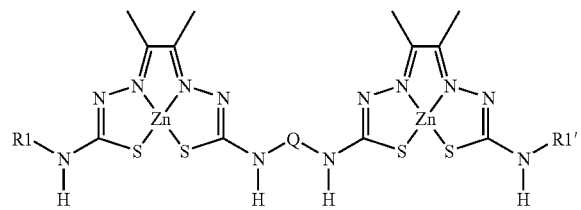

wherein R1 and R1' are as described for a complex of the invention as defined above, and Q represents -L1- or -L1-E—, wherein L1 is as described for a complex of the invention as defined above, and E represents —V-L3—, —V-L3-alk—, alk-V-L3—, -alk-V-L3-alk—, or a substituted or unsubstituted group selected from an alkyl, carbocyclic, cycloalkyl, heterocyclic, -alk-carbocyclic, -alk-cycloalkyl and -alk-heterocyclic group to which the complex on the right hand side of Q is either bonded directly, or to which the complex on the right hand side of Q is bonded via a linking L3- or L3-alk-group that is part of the group Q (to give -L3-[right hand complex] or -L3-alk-[right hand complex]), wherein L3 is as defined above for L1 and L1', —V— is a linking group of the following formula:

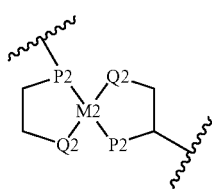

wherein P2 and Q2 are independently selected from N, O, P and S and M2 is a metal atom.

In one embodiment the present invention provides complexes as defined above wherein M is typically Cu. It may be a stable isotope or radioisotope of Cu. It may, for instance, be $^{60}$Cu, $^{61}$Cu, $^{62}$Cu, $^{64}$Cu or $^{67}$Cu. M is alternatively Ni or Zn. M may be a stable isotope or radioisotope of Zn. It may, for instance, be $^{60}$Zn, $^{61}$Zn, $^{62}$Zn, $^{63}$Zn, $^{65}$Zn, $^{69}$Zn, $^{71}$Zn or $^{72}$Zn.

In one embodiment the present invention provides a metal complex of formula (I):

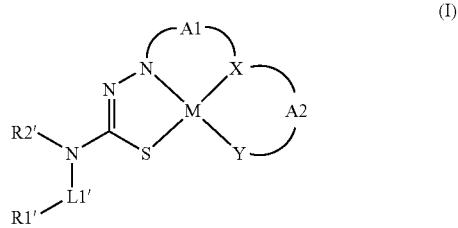

wherein:

M is a transition metal;

A1 is:

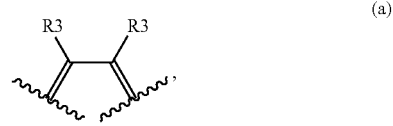

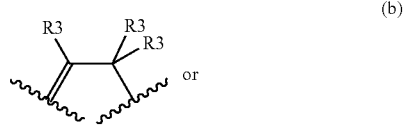

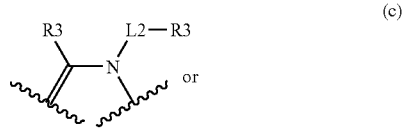

A2, X and Y are as defined in (i), (ii) and (iii) which follow:

(i) A2 is

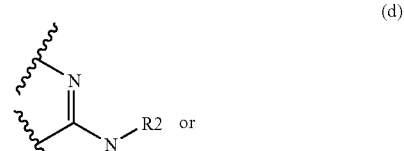

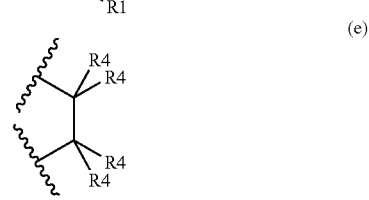

X is N or P and A1 is attached to X via a double bond, or X is O, S, N(R5) or P(R5) and A1 is attached to X via a single bond; and Y is N, O, P, S, N(R5), O(R5), P(R5) or S(R5); or (ii) X is N or P and A1 is attached to X via a double bond, or X is O, S, N(R5) or P(R5) and A1 is attached to X via a single bond; and Y and A2 together represent a moiety of formula (B):

(B)

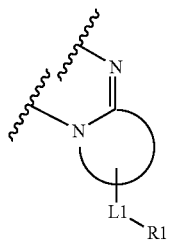

wherein the ring that is substituted by L1-R1 is a 5- to 11-membered heterocyclic group; or (iii) X, A2 and Y together represent

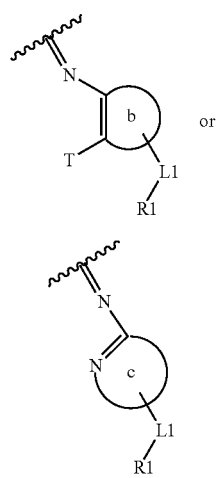

wherein T is OH, O—, COOH or C(O)O— and rings b and c are aromatic $C_{6-10}$ carbocyclic or 5 to 11 membered aromatic heterocyclic groups;

L1 and L1', which are the same or different, are each independently selected from a covalent bond and a linker group selected from —C(O)—, -alk-C(O)—, —C(O)O—, -alk-C(O)O—, —OC(O)—, -alk-OC(O)—, —O—, -alk-O—, —N(R7)—, -alk-N(R7)—, —N(R7)C(O), -alk-N(R7)C(O)—, —C(O)N(R7), -alk-C(O)N(R7), —C(S)—, -alk-C(S)—, —S—, -alk-S—, —C(S)N(R7)—, -alk-C(S)N(R7)—, —N(R7)C(S)—, -alk-N(R7)C(S)—, —S(O)$_2$N(R7)—, -alk-S(O)$_2$N(R7)—, —N(R7)S(O)$_2$—, -alk-N(R7)S(O)$_2$—, —S(O)—, -alk-S(O)—, —N(R7)C(O)O—, -alk-N(R7)C(O)O—, —OC(O)N(R7)—, -alk-OC(O)N(R7)—, —N(R7)C(O)N(R7)—, -alk-N(R7)C(O)N(R7)—, —N(R7)C(S)N(R7)—, -alk-N(R7)C(S)N(R7)—, —N=C(R7)—, -alk-N=C(R7)—, —C(R7)=N— and -alk-C(R7)=N—;

R' and R1', which are the same or different, are each independently selected from hydrogen, Z and a group selected from an alkyl, carbocyclic, cycloalkyl, heterocyclic, alk-carbocyclic, alk-heterocyclic and alk-cycloalkyl group, which group may be further substituted by L3-Z or L3-alk-Z, wherein L3 is as defined above for L1 and L1' and Z is a moiety selected from a biologically active molecule, a fluorophore, a cytotoxin, an amino acid, a peptide, an oligopeptide, a polypeptide, a group containing a label, a leaving group which is replaceable by a group containing a label, and a complex of Cu, Ni or Zn with a bis(thiosemicarbazone) or a thiosemicarbazone;

-alk- is an alkylene, alkenylene or alkynylene group based on an alkyl, alkenyl or alkynyl group;

R2 and R2', which are the same or different, are each independently selected from H, $C_1$-$C_6$ alkyl and $C_1$-$C_6$ alkoxy;

R3 and R4, which are the same or different, are each independently selected from H, $C_1$-$C_6$ alkyl, heterocyclic group and phenyl;

R5 is a group comprising an electron donor group, which donor group is separated by two carbon atoms from the O, N, S or P atom to which R5 is attached;

R7 is H, alkyl or cycloalkyl; and

L2 is —C(O)— or a covalent bond;

with the proviso that when X is N, Y is S, A1 is =C(R3)-C(R3)= and A2 is (d), then the moiety represented by -L1-R1 is other than H, unsubstituted alkyl or unsubstituted alkoxy.

In another embodiment, the present invention provides a metal complex of formula (I):

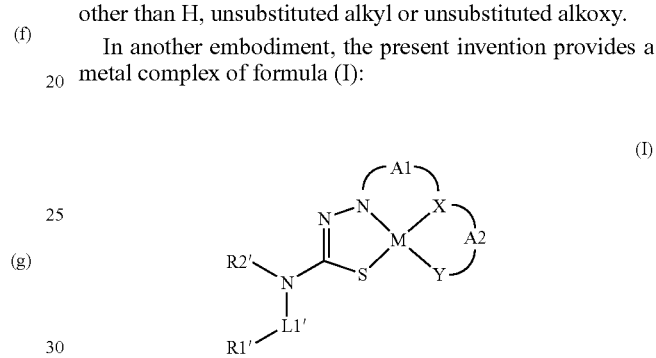

wherein:

M is Cu, Zn or Ni;

A1 is:

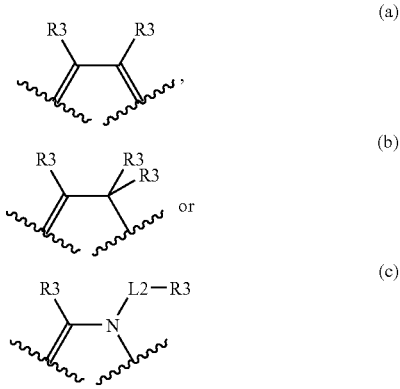

A2, X and Y are as defined in (i), (ii) and (iii) which follow:

(i) A2 is

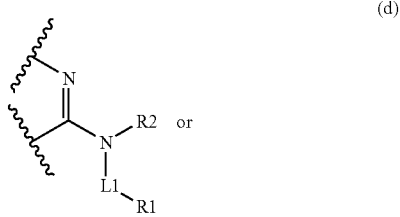

-continued

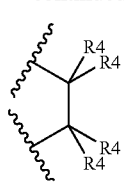
(e)

X is N or P and A1 is attached to X via a double bond, or X is O, S, N(R5) or P(R5) and A1 is attached to X via a single bond; and Y is N, O, P, S, N(R5), O(R5), P(R5) or S(R5); or
(ii) X is N or P and A1 is attached to X via a double bond, or X is O, S, N(R5) or P(R5) and A1 is attached to X via a single bond; and Y and A2 together represent a moiety of formula (B):

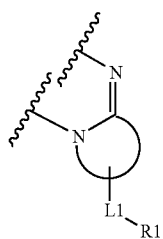
(B)

wherein the ring that is substituted by L1-R1 is a 5- to 11-membered heterocyclic group; or
(iii) X, A2 and Y together represent

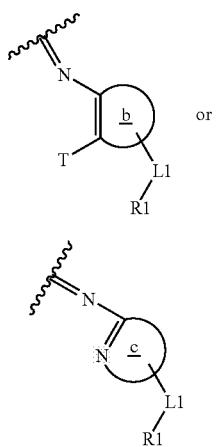
(f) or (g)

wherein T is OH, O—, COOH or C(O)O— and rings b and c are aromatic $C_{6-10}$ carbocyclic or 5 to 11 membered aromatic heterocyclic groups;

L1 and L1', which are the same or different, are each independently selected from a covalent bond and a linker group selected from —C(O)—, -alk-C(O)—, —C(O)O—, -alk-C(O)O—, —OC(O)—, -alk-OC(O)—, —O—, -alk-O—, —N(R7)—, -alk-N(R7)—, —N(R7)C(O), -alk-N(R7)C(O)—, —C(O)N(R7), -alk-C(O)N(R7), —C(S)—, -alk-C(S)—, —S—, -alk-S—, —C(S)N(R7)—, -alk-C(S)N(R7)—, —N(R7)C(S)—, -alk-N(R7)C(S)—, —S(O)$_2$N(R7)—, -alk-S(O)$_2$N(R7)—, —N(R7)S(O)$_2$—, -alk-N(R7)S(O)$_2$—, —S(O)—, -alk-S(O)—, —N(R7)C(O)O—, -alk-N(R7)C(O)O—, —OC(O)N(R7)—, -alk-OC(O)N(R7)—, —N(R7)C(O)N(R7)—, -alk-N(R7)C(O)N(R7)—, —N(R7)C(S)N(R7)—, -alk-N(R7)C(S)N(R7)—, —N═C(R7)—, -alk-N═C(R7)—, —C(R7)═N— and -alk-C(R7)═N—;

R1 and R1', which are the same or different, are each independently selected from hydrogen, Z and a group selected from an alkyl, carbocyclic, cycloalkyl, heterocyclic, -alk-carbocyclic, -alk-cycloalkyl and -alk-heterocyclic group, which group may be further substituted by L3-Z or L3-alk-Z, wherein L3 is as defined above for L1 and L1' and Z is a moiety selected from a biologically active molecule, a fluorophore, a cytotoxin, an amino acid, a peptide, an oligopeptide, a polypeptide, a group containing a label, a leaving group which is replaceable by a group containing a label, and a complex of Cu, Zn or Ni with a bis(thiosemicarbazone) or a thiosemicarbazone;

-alk- is an alkylene, alkenylene or alkynylene group based on an alkyl, alkenyl or alkynyl group;

R2 and R2', which are the same or different, are each independently selected from H, $C_1$-$C_6$ alkyl and $C_1$-$C_6$ alkoxy;

R3 and R4, which are the same or different, are each independently selected from H, $C_1$-$C_6$ alkyl, heterocyclic group and phenyl;

R5 is a group comprising an electron donor group, which donor group is separated by two carbon atoms from the O, N, S or P atom to which R5 is attached;

R7 is H, alkyl or cycloalkyl; and

L2 is —C(O)— or a covalent bond;

with the proviso that when X is N, Y is S, A1 is ═C(R3)-C(R3)═ and A2 is
—N(H)C(═)N(R1)-L1-R1, then the moiety represented by -L1-R1 is other than H, unsubstituted alkyl or unsubstituted alkoxy.

Where it is desired to obtain a particular enantiomer of a compound or complex of the present invention as defined above, this may be produced from the corresponding mixture of enantiomers using a suitable conventional procedure for resolving enantiomers. Thus for example, diastereomeric derivatives, e.g. salts, may be produced by reaction of a mixture of enantiomers of Formula I e.g. a racemate, and an appropriate chiral compound, e.g. a chiral base. The diastereomers may then be separated by any convenient means, for example by crystallisation and the desired enantiomer recovered, e.g. by treatment with an acid in the instance where the diastereomer is a salt. In another resolution process a racemate of Formula (I) may be separated using chiral High Performance Liquid Chromatography. Alternatively, if desired, a particular enantiomer may be obtained by using an appropriate chiral intermediate in one of the processes described above.

In formulae (III), (IIIa), (IIIb), (I) and (Ib), X is typically N, P, O or S. More typically it is N or P and A1 is attached to X via a double bond. Most typically, X is N.

In formulae (III), (IIIb), (I) and (Ib), typically Y is N, P, O, S, N(R5) or P(R5). More typically it is N, S, N(R5) or P(R5). More typically still, Y is S or N(R5). Typically, Y is S.

In formulae (III), (IIIa), (IIIb), (I), (Ia) and (Ib), typically R3 is H or $C_{1-6}$alkyl. More typically, it is H or $C_{1-3}$alkyl. Typically, it is H or methyl.

In formulae (III), (IIIb), (I), and (Ib), typically R4 is H or $C_{1-6}$alkyl. More typically, it is H or $C_{1-3}$alkyl. More typically still, it is H or methyl. Typically it is H.

In formulae (I) and (Ib), typically A1 and A1' are (a). In formulae (III), (IIIa) and (IIIb) typically A1 and A1' are (a') and n is O.

In one embodiment of the present invention, M in formulae (III), (IIIa), (IIIb), (I), (Ia) and (Ib) is Cu.

In another embodiment of the present invention, M in formulae (III), (IIIa), (IIIb), (I), (Ia) and (Ib) is Zn.

In another embodiment of the present invention, M in formulae (III), (IIIa), (IIIb), (I), (Ia) and (Ib) is Ni.

In formulae (III), (IIIa), (IIIb), (I), (Ia) and (Ib), typically L1 is a covalent bond, —NR7—, —N=C(R7)—, —C(R7)-N(R7)—, —N(R7)C(O)— or —C(O)N(R7)-.

In formulae (I) and (III), typically R2 and R2' are H or $C_{1-6}$alkyl. More typically they are H or $C_{1-3}$alkyl. Even more typically they are H or methyl.

In formula (II) typically R8 is H.

In the definition of R9 in formula (II) a carbocyclic group is typically phenyl, a heterocyclic group is typically pyridine and R6 is typically H or methyl, typically methyl.

Rings b and c in formula (I) and formula (II) are typically selected from benzene, naphthalene, pyridine, pyridazine, pyrimidine, pyrazine, triazine, quinoline, isoquinoline, quinazoline, quinoxaline, naphthyridine and pteridine, more typically benzene or pyridine.

The heterocyclic group in formula B is typically pyridine, pyridazine, pyrimidine, pyrazine, triazine, quinoline, isoquinoline, quinazoline, quinoxaline, naphthyridine or pteridine, more typically pyridine.

Preparation of Complexes of the Invention

Various methods may be suitable for producing the compounds and complexes of the invention, depending on the nature of the desired product. In one embodiment metallation is the final step in the production of the complex. However, this is not essential for all complexes of the invention. Accordingly, in the procedures described below metallation may take place at any stage provided that a suitable site is available. In one embodiment, metallation occurs before the group comprising Z is attached.

Complexes of formula (III) of the invention as defined above may be prepared from their metal-free ligand precursors by simple metallation reaction with a suitable salt of the metal M, in a suitable solvent. Examples of suitable salts include $M(OAc)_2 \cdot xH_2O$ and the chloride dihydrate of the metal M. Typically, $M(OAc)_2 \cdot xH_2O$ is used. Generally x is from 1 to 4. Typically, x is 1 for Cu, 1 or 2 for Zn and 4 for Ni.

Examples of suitable solvents include DMSO and lower alkyl alcohols. Typically, methanol or ethanol is used. Typically the reaction requires heating. Typically heating takes place under reflux. Heating may be required for up to 16 hours or more. Typically the reaction mixture is heated for 3 hours.

The reaction is typically carried out under an inert atmosphere such as nitrogen. After cooling the complex is typically recovered in the form of a powder after washing with suitable agents, such as methanol or diethyl ether, and drying in vacuo. Filtration may also be used to recover the product.

The above general method is represented in the following scheme:

gen atom alpha to Y. In another embodiment Y is a group comprising a substituent R5, which carries a hydrogen atom that can be lost during metallation; for example, the substituent could comprise a $CO_2H$ or NHR6 group.

Complexes of formula (III) of the invention as defined above wherein M is Cu(1) may be prepared from their metal-free ligand precursors by reaction with $[Cu\{CH_3CN\}_4]BF_4$. Typically this requires stirring and is conducted at room temperature. Typically the reaction takes one hour. The Cu complex may be recovered by precipitation after the addition of diethyl ether.

For mono- and bidentate ligands the thermodynamic stabilities of corresponding complexes of bivalent ions of the first transition series, irrespective of the particular ligand involved, usually vary in accordance with the Irving-Williams series: Mn(II)<Fe (II)<Co(II)<Ni(II)<Cu(II)>Zn(II). Chelating and macrocyclic ligands can form a cavity which can be used to select one ion over another based on size. In general, however, copper complexes are expected to be more stable than analogous zinc complexes. The reaction between a zinc bis(thiosemicarbazone) and copper acetate should result in the formation of a copper bis(thiosemicarbazone) and zinc acetate.

In one embodiment the present invention provides zinc and nickel complexes of formula (III) of the invention as defined above, from which the corresponding copper complex may be prepared by transmetallation. In this regard, it is of note that the carbon-carbon bond length of the diimine backbone increases upon alkylation, and consequently the ligand is better able to accommodate the copper ion with bond angles closer to the right angles preferred at square planar metal centres. In one embodiment the copper atom is a radionuclide. More typically, it is a positron emitter such as $^{64}Cu$. Transmetallation may be effected by reaction of a nickel or zinc complex of formula (III) of the invention as defined above with a suitable copper salt in a suitable solvent. An example of a suitable copper salt is $Cu(OAc)_2 \cdot H_2O$. Examples of suitable solvents include methanol, ethanol and DMSO. In one embodiment the zinc complex is initially dissolved in the minimum possible amount of DMSO and the copper salt is dissolved in methanol, before being mixed. In another embodiment, both the nickel or zinc complex and the copper salt are dissolved in ethanol, before being mixed. Typically, the mixture requires stirring during the reaction. Usually, no heating is required and the reaction is conducted at room temperature. Typically, the reaction takes one hour.

Metal-free ligands of the present invention as defined above may be prepared by the following reaction:

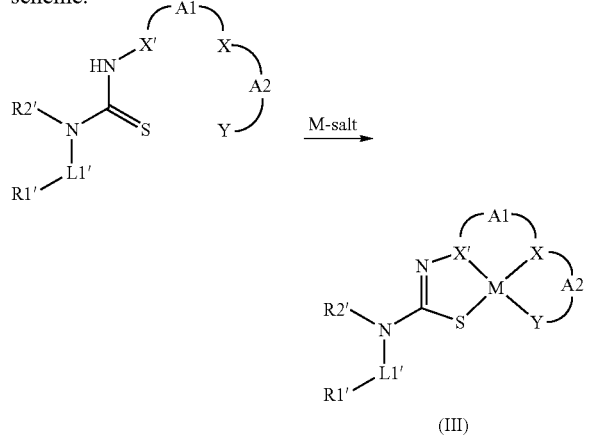

(III)

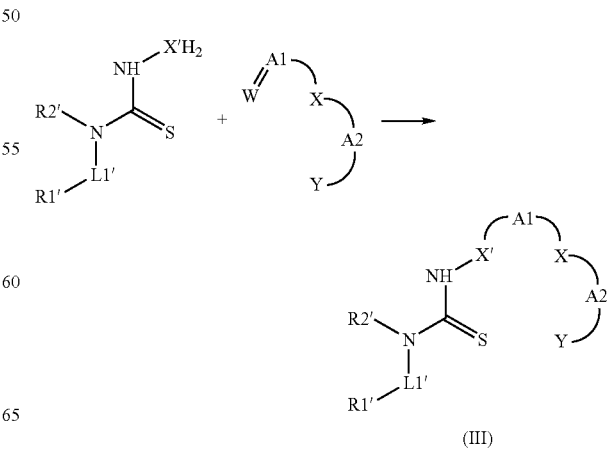

(III)

In a preferred embodiment of this scheme Y in the free ligand is linked to A2 by a double bond and there is a hydrowherein W is O or NOH and R1', L1', R2', A1, X, X', A2 and Y are as defined for formula (III) above.

Ligands wherein A1 is =C(R3)-C(R3)= and X is N or P may be prepared by the following scheme:

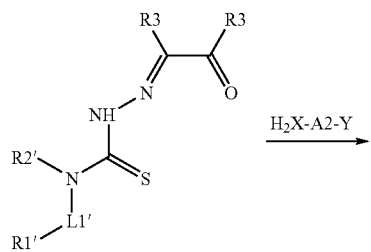

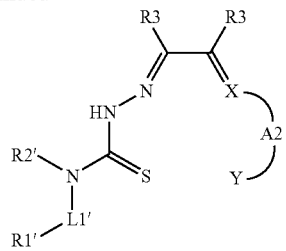

wherein typically X is N.

The keto-N4-(R2)(R1-L1)thiosemicarbazone may be prepared by a reaction of the corresponding (R2)(R1-L1)thiosemicarbazide with R3-C(O)—C(O)—R3.

Various methods may be used for the synthesis of symmetric and asymmetric thiosemicarbazone derivatives. The skilled person will appreciate that care must be taken to prevent side reactions, and that the most suitable approach will vary according to the desired product. The following approaches may be used to produce metal complexes and free ligand precursors of the invention wherein A1 is (a), X is N, A2 is (d) and Y is N. Typically, approach C is used.

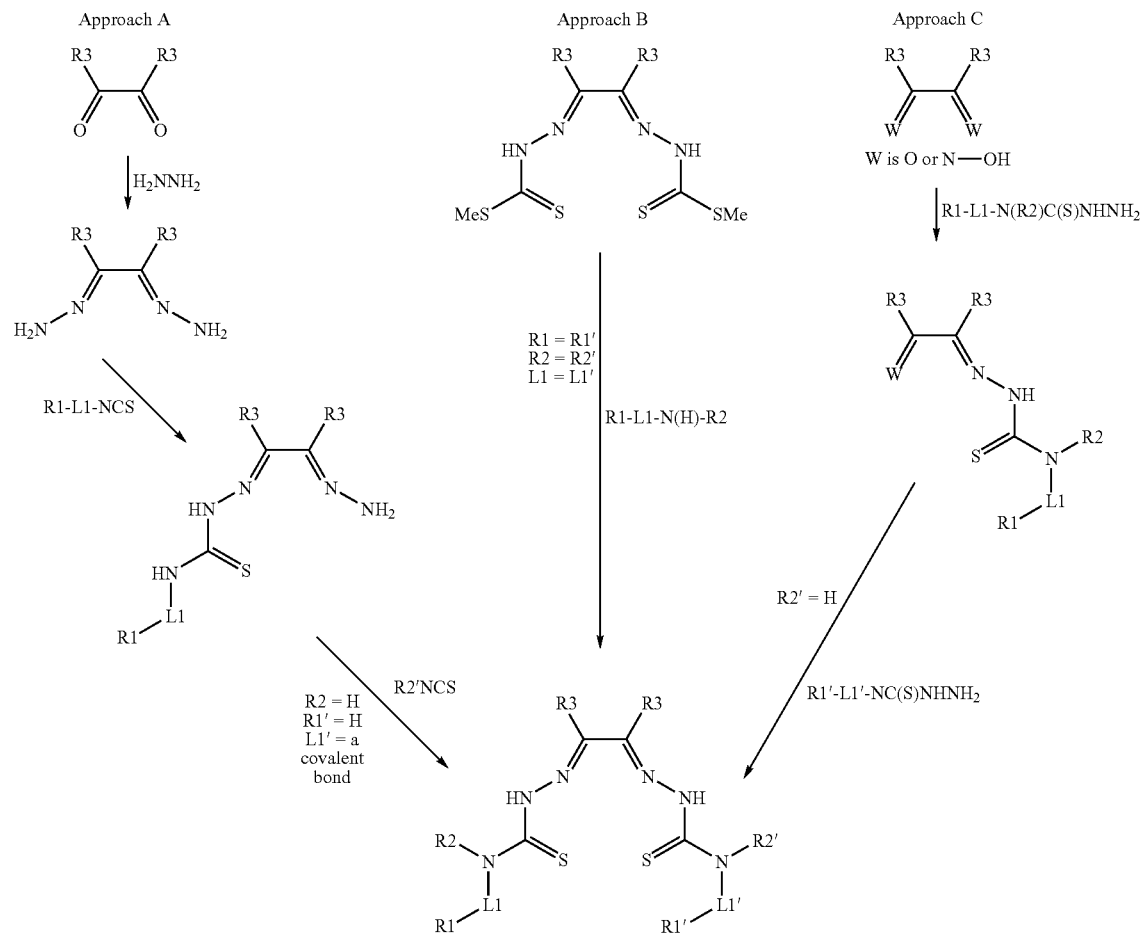

For example, such thiosemicarbazone derivatives which also have terminal N4-benzoic acids may be synthesised as follows, in accordance with approach C above:

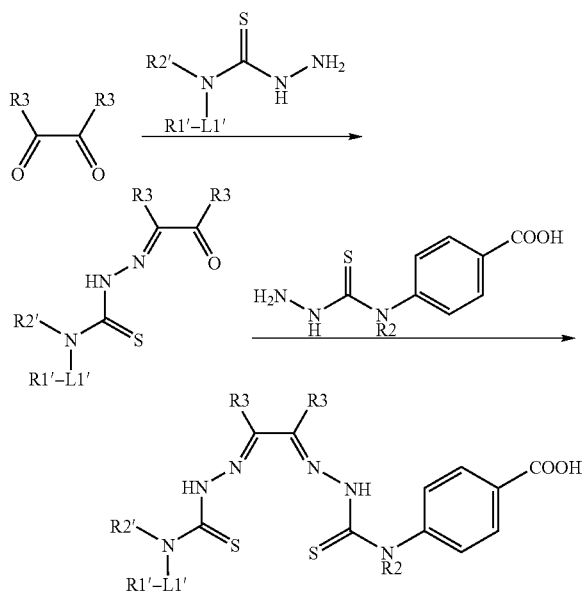

The use of DMF may be necessary in the second step to avoid esterification reactions that may occur in MeOH or EtOH; the reactants dissolve in DMF and their reaction produces minimal impurities. The temperature of the solution in step two is typically maintained below 50° C. to minimise cyclisation reactions and the decomposition of DMF. The products may be isolated by precipitation with water.

The terminal carboxylic acid group can then be used to couple the thiosemicarbazone derivative to a group Z. For example, the carboxylic acid group can be readily converted into an activated ester, which is susceptible to nucleophilic attack by amines and hydrazines.

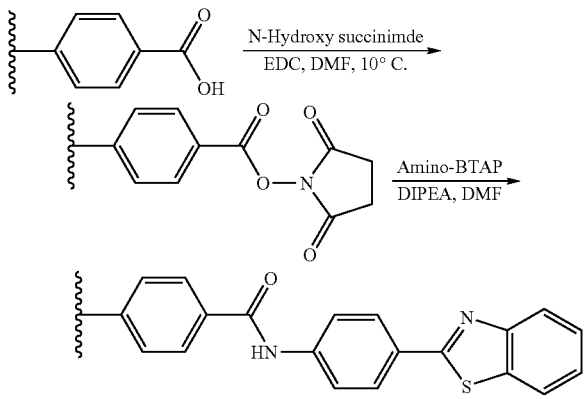

Generally, the group —Z, or the group -L3-Z— or the group -L3-alk-Z may be coupled to the metal complex or free ligand using conventional techniques known to the person of skill in the art. In one embodiment of the present invention, Z is coupled to the thiosemicarbazone derivative via one or more peptide bonds, typically one peptide bond. Typically, when Z is linked via a peptide bond, this link is formed in a reaction between a —COOR7 group and a —NHR7 group in the thiosemicarbazone derivative and the group containing Z, respectively, or vice versa.

In another embodiment of the present invention, Z is coupled to the thiosemicarbazone derivative via one or more imine links, typically one imine link. A example of this embodiment is shown in the following scheme:

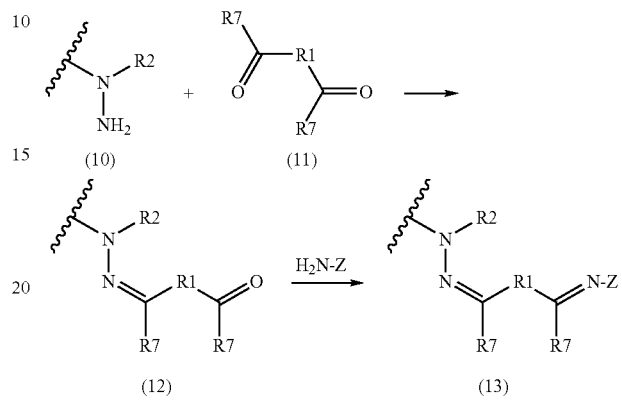

The dione is typically symmetrical and nucleophilic attack on the dione takes place at both carbonyl groups, giving rise to a thiosemicarbazone derivative (13) which is symmetrical about R1. If (10) is already complexed to a metal centre, the product (13) is a binuclear metal complex of the thiosemicarbazone derivative.

Accordingly, in one aspect the present invention provides a metal complex of formula (III) as defined above, or a free ligand precursor thereof, wherein Z is itself a thiosemicarbazone or bis(thiosemicarbazone), or a complex of Cu, Zn or Ni therewith. Such thiosemicarbazone and bis(thiosemicarbazone) derivatives may alternatively be prepared by reaction of the mono-keto-thiosemicarbazone with a dithiosemicarbazide according to the following scheme:

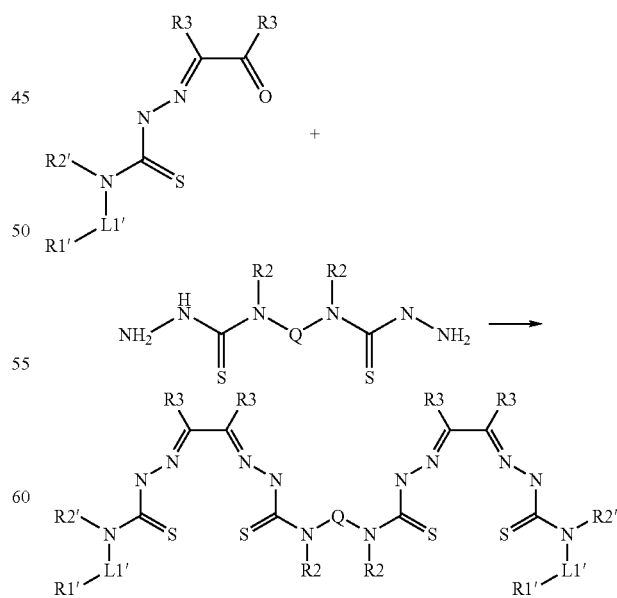

wherein Q is -L1- or -L1-R1-L3- and wherein L1, L3 and R1 are as defined above for formula (III).

Alternatively, such thiosemicarbazone derivatives may be prepared by reaction of a mono-hydrazone-(thiosemicarbazone) with a diisothiocyanate according to the following scheme:

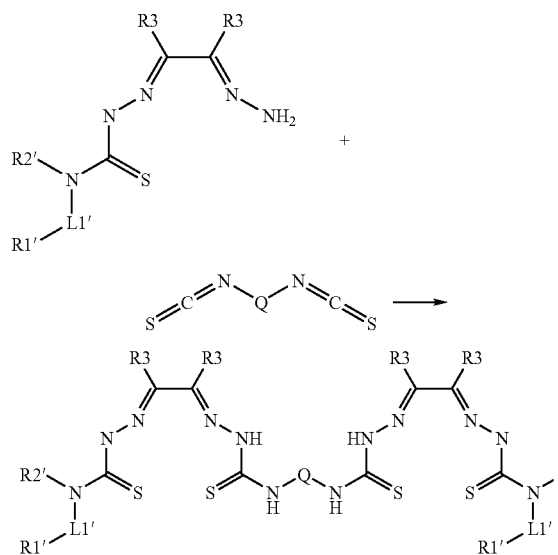

wherein Q is as defined above in connection with formula (Ic).

Alternatively again, such thiosemicarbazone derivatives may be prepared by reaction of a dithiosemicarbazone and a thiosemicarbazide according to the following scheme:

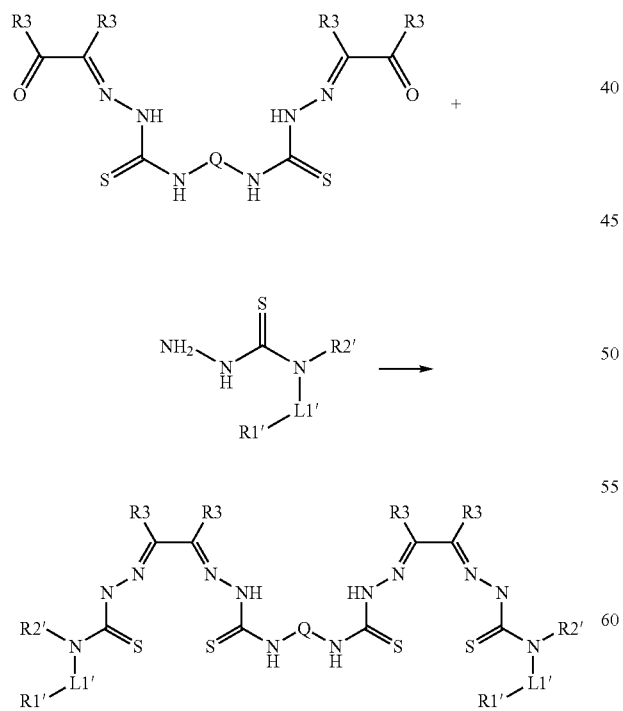

wherein Q is as defined above in connection with formula (Ic).

In another embodiment, thiosemicarbazone derivatives wherein L1 is —N(R7)- may be prepared according to the following scheme:

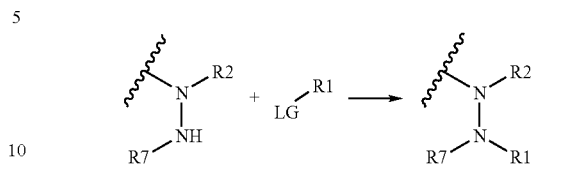

wherein LG is a suitable leaving group such as Br or Cl.

In a further embodiment thiosemicarbazones wherein L1 is —N=C(R7)- may be prepared according to the following scheme:

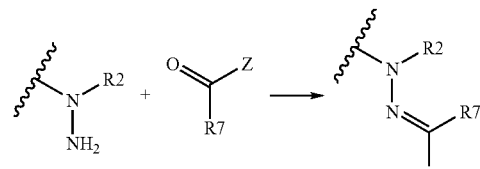

Typically, where it appears in the above schemes and in all thiosemicarbazone derivatives of the invention as defined above, R7 is H.

Some more specific examples of processes suitable for preparing the complexes of the present invention, in particular, to the mono and bi-nuclear zinc complexes of the present invention, are as follows. The starting point for the synthesis is commonly a diketone; the addition of two equivalents of a thiosemicarbazide to a diketone generates a symmetric bis(thiosemicarbazone), as described by D. X. West et al in *Polyhedron*, 1997, 16, 1895. Alternatively, reaction of the diketone with one equivalent of a thiosemicarbazide gives a mono(thiosemicarbazone), which can be isolated and condensed with a second thiosemicarbazide to give a dissymmetric bis(thiosemicarbazone). J. P. Scovill, *Phosphorus, Sulfur, Silicon and Related Elements*, 1991, 60, 15 describes a synthetic approach to the formation of linked thiosemicarbazides.

The bi-nuclear (bimetallic bis(thiosemicarbazone)) zinc complexes may be tethered with rigid links, such as a 1,4-disubstituted benzene group or a 2,4-disubstituted toluene group, or non-rigid links, such as alkylene groups. They are typically tethered with links derived from ethylene diamine, glyoxal, diaminobenzenes and aryl dialdehydes.

As regards tethering with a rigid spacer, J. P. Scovill (in *Phosphorus, Sulfur, Silicon and Related Elements*, 1991, 60, 15.) reported a transamidation procedure for making thiosemicarbazides from 4-methyl-4-phenylthiosemicarbazide 14. This procedure has been employed in the formation of 4-alkylthiosemicarbazides from alkylamines. Alternatively, such complexes of the invention may be prepared by the use of commercially available isothiocyanates 15 and 16 depicted below. See Examples 12A and B.

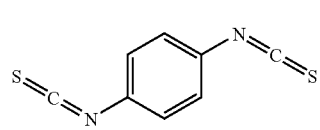

15

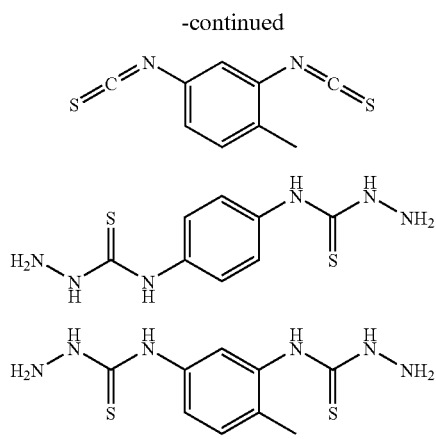

The preparation of the bimetallic zinc complexes are generally better prepared than the corresponding uncomplexed linked bis(thiosemicarbazones). The former can generally be prepared in higher yields and with a greater degree of purity, by template reactions of linked thiosemicarbazides 6 and mono(thiosemicarbazones) 4 with zinc acetate.

Alternatively, it is also possible to produce the bi-nuclear complexes by linking two preformed bis(thiosemicarbazones) or zinc complexes. The Examples in Section 16 describe suitable methods for this approach.

Uses of Complexes of the Invention

The present invention allows functional substituents, such as biologically active molecules and labelled groups, to be conjugated to metal complexes in such a way as to maximise the potential biomedical use of those complexes. U.S. Pat. No. 5,843,400 cited above discloses the use of hypoxic selective copper bis(thiosemicarbazones) in the PET imaging of hypoxia. In complexes of the present invention that application is extended, both by the manipulation of the redox properties of the central metal atom in the complex and by the formation of conjugates in which the complex, whether or not it is itself inherently hypoxic, is attached via suitable linker moieties to functional substituents such as biologically active molecules and groups which bear a label. Typically the complex is linked via an exocyclic nitrogen, which may have the advantage of causing minimum perturbation in any potential hypoxic selectivity of the molecules.

Hypoxic cells have a lower than normal oxygen concentration. Typically, the partial pressure of oxygen falls to $pO_2 < 3$ mmHg of the normal concentrations (20-80 mmHg), occurring usually as a result of insufficient blood supply to the affected tissue which in turn can lead to anaerobic respiration and the lowering of cellular pH from an accumulation of lactic acid. Hypoxia selective complexes have the potential to be used as imaging agents to visualize hypoxic tissue in a wide range of oncological, neurological and cardiological applications and can also be adapted for use in therapy, targeted specifically to these regions. This property is of particular importance since conventional methods of radiotherapy are poor at treating areas of hypoxia due to the absence of oxygen, a strong radiosensitizer.

Hypoxic selectivity of complexes of the invention is typically lost when any of the groups R3 in the backbone moiety A1 in formula (III) is other than H or methyl. Thus, in one aspect of the invention each R3 in formula (III) is H or CH$_3$ and the resulting complex is hypoxic selective.

Modification of the substituents present on the bis(thiosemicarbazone) ligand can be used to control, for example, the lipophilicity of the ligand and resulting complex. For example, lipophilicity can be increased with increasing alkyl substitution of the conjugated ligand backbone, particularly in the groups R2, R2', L1, L1', R1 and R1'. For example, for Cu[PTS], log P=0.76 (where P is the octanol/water partition coefficient) whereas for Cu[PTSM$_2$], log P=3.18.

Biologically active molecules in this context may be those mentioned above, for instance therapeutic agents and agents which target the conjugated complex to the desired site in vivo. They include cytotoxins, monoclonal antibodies and peptides. Groups which bear a label include those mentioned above, for instance groups which include a radionuclide or a fluorophore.

The uses of complexes of formula (III) as defined above, in which the complex itself is conjugated to a functional substituent (for instance, a complex of formula (III) in which A2 is option (d) in which R1 is either Z or a group substituted by Z, or a complex of formula (IIIa)) hinges on whether the conjugates are hypoxic selective or not:

If the conjugates are not hypoxic selective then attachment of an appropriate biologically active molecule as Z will permit the conjugates to be used as diagnostic imaging agents (for instance, when Z is a monoclonal antibody or a peptide). The long-lived Cu isotope is of interest in the context of PET (positron emission tomography) imaging of the biodistribution of drugs as part of the screening process. Cu bis(thiosemicarbazones) have proven biological stability for imaging applications and are moreover somewhat stabilised against the reductive elimination of copper, which is a problem with the current range of bifunctional chelators used for Cu such as TETA and related compounds. When metal M in complexes of formulae (III), (IIIa), (IIIb), (I), (Ia) and (Ib) is Zn, the intrinsic fluorescence of Zn can be exploited to examine biological systems at a cellular level.

If the metal complex is hypoxic selective to start with, for instance due to the redox behaviour of the metal centre, then suitable manipulation of the linker group and functional substituent on the side-chain in the final conjugate of formula (III) or (IIIa) allows that hypoxic selectivity to be retained. Cu is typically the metal M in complexes of the invention which are hypoxic selective. The complex can act as a hypoxic selective vector to deliver a range of functional molecules to the desired site in vivo, in particular to tumours, giving rise to a wide range of biomedical applications. Those applications include therapy, diagnosis and medical imaging, examples of which are as follows.

When Z in formula (III) or (IIIa) as defined above is a metal based or organic fluorophore and M is Cu, there is the possibility of optical imaging of hypoxia. In particular, if the fluorophore exhibits two photon fluorescence then the emission is at a sufficiently long wavelength to be detected externally to the body of the patient. If a radioisotope of copper is used there is the possibility of simultaneous optical and PET imaging with cold copper, non-radioactive optical imaging. The fluorophore should also permit the tracking of the complexes at the cellular level and provide an unprecedented insight into the mechanism of hypoxic selectivity in living tumour cells.

As noted above, in one embodiment the present invention provides complexes wherein M is zinc (Zn(II)) which are fluorescent, and in a further embodiment, on of R1 and R1' features a group Z that represents a second zinc bis(thiosemicarbazone) complex joined by a linker group, thus creating a bi-nuclear zinc complex. Manipulation of the substituents present may also enable enhancement of the quantum yield of the fluorescence. Obviously, this brings obvious advantages, such as the possibility to increase sensitivity in cellular measurements.

In this embodiment of the invention a wide range of variation of the linker moiety is possible. Such modification can provide bi-nuclear complexes are 3 to 10 times more fluorescent than the mono-nuclear complexes. Further, attachment of appropriate moieties capable of Fluorescence Resonance Energy Transfer (FRET) can enhance the fluorescence intensity substantially. This can, for example, be achieved by when —N(R2)-L1-R1 and/or —N(R2')-L1'-R1' represents an —NH-napthyl group. Thus, in one embodiment the present invention provides such bi-nuclear complexes wherein one of —N(R2)-L1-R1 and —N(R2')-L1'-R1' represents an —NH-carbocyclic or —NH-heterocyclic group which group is aromatic and capable of FRET. Further examples of carbocycles and heterocycles from which suitable moieties can be derived include naphthalene, azulene, fluorene, anthracene, acridine, carbazole, phenazine, phenothiazine, phenoxazine, pteridine, 1,8-naphthyridine, quinoxaline, quinazoline, phthalazine, cinnoline, isoquinoline, quinoline, purine, benzthiazole, benzimidazole, 1H-indazole, indolizine, indole, isoindole, benzo(b)furan and benzo(b)thiophene.

More typical examples include the carbocycles naphthalene, azulene, fluorene and anthracene. However, this embodiment of the complexes of the present invention is not restricted to zinc complexes. By considering the EPR (Electron Paramagnetic Resonance) properties of the equivalent bi-nuclear copper complexes it may be possible to demonstrate the rate of change of interaction between the paramagnetic copper with distance- a molecular ruler. The fixed distance between the two paramagnetic copper centres could be used to calibrate the determination of Cu—Cu distances by pulsed ESR techniques. The coupling between Cu(II) centres at known distances is measured, and the information used to obtain Cu—Cu distances in other compounds, for example, binuclear copper containing metalloproteins and enzymes, for which structure elucidation is not trivial. Ideally the two paramagnetic centres of a molecular ruler would only interact through space. This is in order that the interactions between the Cu centres measured by pulsed ESR are not complicated by direct electronic interaction causing antiferromagnetic exchange. It is important to have a wide range of distances so that the direct electronic contact terms can be separated from the through space and other terms. The advantage of linking two bis(thiosemicarbazone) units through the additional nitrogen at N(4) is that it greatly reduces the possibility of direct conjugation through the spacer group. The alternatives of amide and imine linkages both offer the possibility of delocalization from one bis(thiosemicarbazone) unit to another, provided the spacer is a conjugated system. For further information of this potential use is described by O. Rohde et al in *J. Am. Chem. Soc.*, 1974, 96, 5311.

The fluorescence of the zinc bis(thiosemicarbazone) complexes of the present invention is particularly interesting When Z in formula (III) or (IIIa) is or comprises another radionuclide and M is Cu, the complex can for instance be used in the SPECT imaging of tumours (using $^{99m}$Tc as the radionuclide) or in PET imaging (using $^{18}$F as the radionuclide). The latter option is particularly desirable since it combines the hypoxic selectivity of the Cu with the ready availability of $^{18}$F. This provides a convenient route to $^{18}$F-based PET imaging agents for hypoxia and for the subsequent monitoring of therapy. If the radionuclide used in Z is a beta emitting radionuclide such as $^{188}$Re, the complex can be used in targeted radiotherapy.

When Z in formula (III) or (IIIa) is a therapeutic agent such as a cytotoxin and M is Cu, the resulting complex can be targeted specifically to tumours, thereby helping to overcome the problem of the radiation therapy resistance of hypoxic zones in tumours. In one embodiment Z is or comprises a reductively activated cytotoxin, and the copper complex releases the active agent in vivo once it is trapped inside the cells.

As an alternative to incorporating a functional group as Z in compounds of formula (III) and (IIIa), the hypoxic selectivity of the complex may be manipulated by suitable selection of X and Y. By varying these atoms and groups it is possible to exert control over factors which may influence hypoxic selectivity such as $pK_a$, reduction potential and stability of a particular redox state of the central metal atom (for instance, the stability of the Cu(I) state when the metal is copper).

As is evident, the complexes of the present invention have a wide range of potential applications, which may be realised by attachment of the appropriate group Z to the complex. Thus, in one embodiment, the present invention provides complexes as defined above, wherein L1', —R1' and/or -L1 and —R1, and, if present, R2 and R2', are such that the complex has one or more terminal functional group that provides a means for simple reaction with another compound to which the skilled person wishes to attach it. Thus, in one embodiment the present invention provides complexes which may serve as a building block for producing a diagnostic agent, which can be added to another compound as and when is convenient depending on the application. For example, terminal groups that may be suitable for such building blocks include Narylcarboxylate, —COOH, —CHO, —NH$_2$, and —OH. For example, when the complex features a terminal —NNH$_2$ group, these can be readily reacted with another molecule with an activated ester or carboxyl chloride group to generate amide bonds, or with carbonyl groups to generate imides. By way of another example, when the complex features a Narylcarboxylate group, this can be readily reacted with another molecule with an —NH$_2$ group to generate an amide. These embodiments of the present invention are relevant for complexes that are hypoxic selective and non-hypoxic selective, complexes comprising a label and complexes which are fluorescent. Examples of complexes of the invention which may serve as building blocks include some of those in Example Section 15.

Complexes of the present invention as defined above may be used as a medicament for use as a diagnostic agent or an imaging agent.

Complexes of the present invention may be also used in a method of imaging a cell, in vitro biopsy sample or patient. Accordingly, the invention provides a method of imaging a cell or in vitro biopsy sample, which method comprises: (a) contacting the cell or in vitro biopsy sample with a complex of the invention as defined herein; and (b) imaging the cell or in vitro biopsy sample. When step (b) is imaging the cell, the imaging of the cell can be done using conventional techniques. When step (b) is imaging the in vitro biopsy sample, the imaging of the in vitro biopsy sample can be performed using conventional techniques. The invention further provides a method of imaging a patient in need thereof, which method comprises: (a) administering to the patient a complex of the invention as defined herein; and (b) imaging the patient. Step (b), of imaging the patient, can be done using conventional techniques.

Typically, in step (b), the imaging is fluorescence imaging. Thus, in one embodiment, the invention provides a method of imaging a cell or in vitro biopsy sample, which method comprises: (a) contacting the cell or in vitro biopsy sample with a complex of the invention as defined herein which complex is fluorescent; and (b) imaging the cell or in vitro biopsy sample using fluorescence imaging. The invention further provides a method of imaging a patient in need thereof, which method comprises: (a) administering to the patient a complex of the invention as defined herein which complex is fluorescent; and (b) imaging the patient using fluorescence imaging.

Alternatively, for imaging an in vitro biopsy sample or a patient, the imaging may be PET or SPECT. Thus, in one embodiment, the invention provides a method of imaging an in vitro biopsy sample, which method comprises: (a) contacting the in vitro biopsy sample with a complex of the invention as defined herein, which complex comprises a radionuclide suitable for PET imaging or SPECT imaging; and (b) imaging the in vitro biopsy sample using PET imaging or SPECT imaging. In another embodiment, the invention provides a method of imaging a patient in need thereof, which method comprises: (a) administering to the patient a complex of the invention as defined herein, which complex comprises a radionuclide suitable for PET imaging or SPECT imaging; and (b) imaging the patient using PET imaging or SPECT imaging. Radionuclides suitable for PET and SPECT imaging respectively are discussed herein.

Complexes of the present invention may be used in a method of imaging a cell, which method comprises administering to the cell a complex of the invention as defined above and then imaging the cell using fluorescence imaging. Alternatively, complexes of the present invention may be used in a method of imaging a patient or an in vitro biopsy sample, which method comprises administering to the patient or in vitro biopsy sample a complex of the invention as defined above and then imaging the patient or in vitro biopsy sample using fluorescence imaging.

The present invention provides a pharmaceutical composition comprising a complex of the invention as defined above and a pharmaceutically acceptable carrier or diluent. In one embodiment, the complex is hypoxic selective. A complex of the invention is formulated for use as a pharmaceutical composition also comprising a pharmaceutically acceptable carrier or diluent. The compositions are typically prepared following conventional methods and are administered in a pharmaceutically suitable form. The complex may be administered in any conventional form, for instance as follows:

A) Orally, for example, as tablets, coated tablets, dragees, troches, lozenges, aqueous or oily suspensions, liquid solutions, dispersible powders or granules, emulsions, hard or soft capsules, or syrups or elixirs. Compositions intended for oral use may be prepared according to any method known in the art for the manufacture of pharmaceutical compositions and such compositions may contain one or more agents selected from the group consisting of sweetening agents, flavouring agents, colouring agents and preserving agents in order to provide pharmaceutically elegant and palatable preparations.

Tablets contain the complex in admixture with non-toxic pharmaceutically acceptable excipients which are suitable for the manufacture of tablets. These excipients may be for example, inert diluents, such as calcium carbonate, sodium carbonate, lactose, dextrose, saccharose, cellulose, corn starch, potato starch, calcium phosphate or sodium phosphate; granulating and disintegrating agents, for example, maize starch, alginic acid, alginates or sodium starch glycolate; binding agents, for example starch, gelatin or acacia; lubricating agents, for example silica, magnesium or calcium stearate, stearic acid or talc; effervescing mixtures; dyestuffs, sweeteners, wetting agents such as lecithin, polysorbates or lauryl sulphate. The tablets may be uncoated or they may be coated by known techniques to delay disintegration and adsorption in the gastrointestinal tract and thereby provide a sustained action over a longer period. For example, a time delay material such as glyceryl monostearate or glyceryl distearate may be employed. Such preparations may be manufactured in a known manner, for example by means of mixing, granulating, tableting, sugar coating or film coating processes.

Formulations for oral use may also be presented as hard gelatin capsules wherein the complex is mixed with an inert solid diluent, for example, calcium carbonate, calcium phosphate or kaolin, or as soft gelatin capsules wherein the active ingredient is present as such, or mixed with water or an oil medium, for example, peanut oil, liquid paraffin, or olive oil.

Aqueous suspensions contain the complex in admixture with excipients suitable for the manufacture of aqueous suspensions. Such excipients are suspending agents, for example, sodium carboxymethylcellulose, methylcellulose, hydroxypropylmethyl-cellulose, sodium alginate, polyvinylpyrrolidone gum tragacanth and gum acacia; dispersing or wetting agents may be naturally-occurring phosphatides, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides for example polyoxyethylene sorbitan monooleate.

The said aqueous suspensions may also contain one or more preservatives, for example, ethyl or n-propyl p-hydroxybenzoate, one or more colouring agents, such as sucrose or saccharin.

Oily suspension may be formulated by suspending the complex in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol.

Sweetening agents, such as those set forth above, and flavouring agents may be added to provide a palatable oral preparation. These compositions may be preserved by this addition of an antioxidant such as ascorbic acid. Dispersible powders and granules suitable for preparation of an aqueous suspension by the addition of water provide the active ingredient in admixture with a dispersing or wetting agent, a suspending agent and one or more preservatives. Suitable dispersing or wetting agents and suspending agents are exemplified by those already mentioned above. Additional excipients, for example sweetening, flavouring and colouring agents, may also be present.

The pharmaceutical compositions of the invention may also be in the form of oil-in-water emulsions. The oily phase may be a vegetable oil, for example olive oil or arachis oils, or a mineral oil, for example liquid paraffin or mixtures of these. Suitable emulsifying agents may be naturally-occurring gums, for example gum acacia or gum tragacanth, naturally occurring phosphatides, for example soy bean lecithin, and esters or partial esters derived from fatty acids an hexitol anhydrides, for example sorbitan mono-oleate, and condensation products of the said partial esters with ethylene oxide, for example polyoxyethylene sorbitan monooleate. The emulsion may also contain sweetening and flavouring agents. Syrups and elixirs may be formulated with sweetening agents, for example glycerol, sorbitol or sucrose. In particular a syrup for diabetic patients can contain as carriers only products, for example sorbitol, which do not metabolize to glucose or which only metabolize a very small amount to glucose.

Such formulations may also contain a demulcent, a preservative and flavouring and coloring agents.

B) Parenterally, either subcutaneously, or intravenously, or intramuscularly, or intrasternally, or by infusion techniques, in the form of sterile injectable aqueous or oleaginous suspensions. This suspension may be formulated according to the known art using those suitable dispersing of wetting agents and suspending agents which have been mentioned above. The sterile injectable preparation may also be a sterile injectable solution or suspension in a non-toxic parenterally-acceptable diluent or solvent, for example as a solution in 1,3-butane diol.

Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition fatty acids such as oleic acid find use in the preparation of injectables;

C) By inhalation, in the form of aerosols or solutions for nebulizers;

D) Rectally, in the form of suppositories prepared by mixing the drug with a suitable non-irritating excipient which is solid at ordinary temperature but liquid at the rectal temperature and will therefore melt in the rectum to release the drug. Such materials are cocoa buffer and poly-ethylene glycols;

E) Topically, in the form of creams, ointments, jellies, collyriums, solutions or suspensions.

The invention will be further described in the Examples which follow:

The following acronyms and abbreviations are used in the Examples and throughout the specification:

| | |
|---|---|
| SPECT | Single photon emission computed tomography |
| ATSMPH$_2$ | Diacetyl bis(N4-phenylthiosemicarbazone) |
| DMSO | Dimethyl sulfoxide |
| DMF | Dimethylformamide |
| THYNICH$_2$ | This is depicted in Example section 1, labelled L$^2$H$_2$ |
| TETA | 1,4,8,11-tetraazacyclotetradecane-N,N',N'',N'''-tetraacetic acid |
| ATSM | Diacetyl bis(N4-methylthiosemicarbazone) or derivative thereof |
| ATSP | Diacetyl-N4-(phenyl)bis(thiosemicarbazone) or derivative thereof |
| BTAP | Thioflavin T derivative: 2-(4-aminophenyl)benzothiazole or derivative thereof |
| DIPEA | N,N-diisopropylethylamine |
| ONSu | N-(benzyloxycarbonyloxy)succinimide |
| DIC | 2-(Dimethylamino)isopropyl chloride hydrochloride |
| HOBt | 1-hydroxybenzotriazole |
| GTS | Glyoxal bis(thiosemicarbazone) or derivative thereof |
| PGTS | Phenyl glyoxal bis(thiosemicarbazone) or derivative thereof |

The abbreviation HYNIC, where used in the specification, represents the following compound:

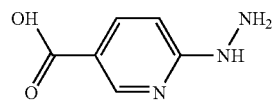

| | Q$^1$ | Q$^2$ | R$^1$, R$^3$ | R$^2$, R$^4$ |
|---|---|---|---|---|
| ATSH$_2$ | Me | Me | H | H |
| ATSMH$_2$ | Me | Me | Me | H |
| GTSH$_2$ | H | H | H | H |
| PTSH$_2$ | Me | H | H | H |
| KTSH$_2$ | CH(OEt)Me | H | H | H |
| KTSMH$_2$ | CH(OEt)Me | H | Me | H |

Where an abbreviation that represents a thiosemicarbazone species is followed by H$_2$, this denotes the metal-tree ligand precursor. The two hydrogen atoms present in that precursor are typically lost on complexation or derivatisation, in which case the H$_2$ label is dropped.

The following table and accompanying figure indicate the names and acronyms of some bis(thiosemicarbazones):

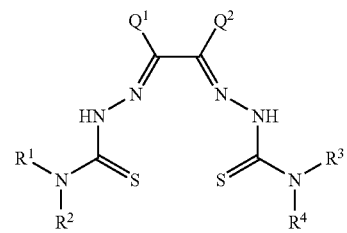

MPLE Section 1

L$^1$H$_2$ and L$^2$H$_2$ and Derivatives Thereof

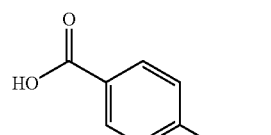
HYNIC

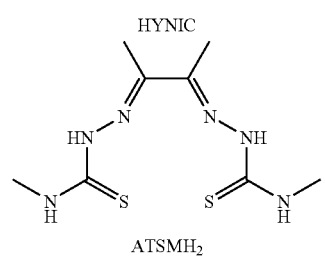
ATSMH$_2$

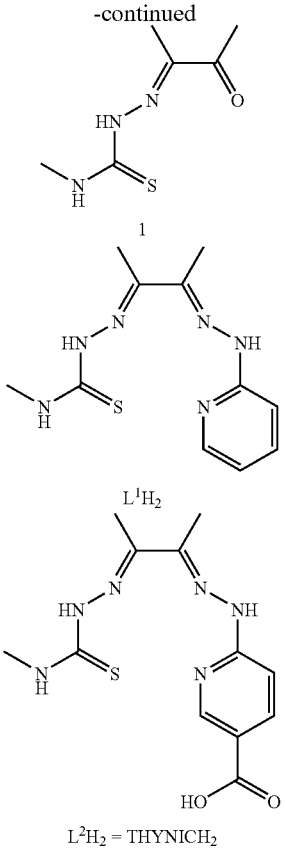

L²H₂ = THYNICH₂

Example 1A

L¹H₂

Acetyl-N4-methyl thiosemicarbazone (1.540 g, 8.90 mmol) was added to 2-hydrazinopyridine (1.261 g, 11.57 mmol) in ethanol (20 mL). The mixture was heated at reflux under an atmosphere of nitrogen for 3 hours. A beige solid precipitated which was collected by filtration, washed with ethanol and diethyl ether to give L¹H₂ (1.899 g, 7.18 mmol, 81%). (Found: C, 49.8; H, 6.22; N, 31.7. Calc'd for $C_{11}H_{16}N_6S$: C, 50.0; H, 6.1; N, 31.8). ¹H NMR (300 MHz): δ 2.21, 6H, s, 2×CH₃; 3.01, d, $^3J_{HH}$=6 Hz, NH—CH₃; 6.83, 1H, m, ArH; 7.23, 1H, d, $^3J_{HH}$=9 Hz, ArH; 7.69, 1H, m, ArH; 8.18, 1H, m, ArH; 8.33, br s, NH; 9.91, 1H, br s, NH; 10.18, 1H, br s, NH. MS: m/z, 265=[L¹+H⁺]⁺.

Example 1B

[Cu(L¹)]

L¹H₂ (0.490 g, 1.86 mmol) and copper acetate monohydrate (0.409 g, 2.05 mmol) were added to ethanol. The mixture was heated at reflux under an atmosphere of nitrogen for 3 hours. The purple mixture was allowed to cool to room temperature and a purple solid was collected by filtration and washed with ethanol and diethyl ether to give [Cu(L¹)].H₂O (0.589 g, 1.71 mmol, 92%). (Found: C, 38.8; H, 4.5; N, 23.8. Calc'd for [Cu(C₁₁H₁₄N₆S)].H₂O: C, 38.4; H, 4.7; N, 24.4). MS: m/z=326=[Cu(L¹)+H⁺].

Example 1C

[Cu(L¹H₂)](ClO₄)₂

[Cu(L¹)].H₂O (ca. 10 mg) was dissolved in methanol (0.5 mL) to give a purple solution. A few drops of concentrated perchloric acid were added (CAUTION! This was done behind a blast shield) causing the solution to immediately turn bright green. Evaporation of the solvent at ambient temperatures gave bright green crystals suitable for X-ray analysis which proved to be [Cu(L¹H₂)](ClO₄)₂.

Example 1D

[Cu(L¹H₂)]Cl₂

L¹H₂ (0.202 g, 0.76 mmol) and copper chloride dihydrate (0.130 g, 0.76 mmol) were added to methanol (15 mL). The mixture was heated at reflux under an atmosphere of nitrogen for 4 hours. The reaction mixture was allowed to cool to room temperature. A green solid precipitated from the dark brown mixture which was collected by filtration, washed with methanol and diethyl ether to give [Cu(L¹H₂)]Cl₂ as green powder (0.100 g, 0.23 mmol, 33%). (Found: C, 33.5; H, 4.1; N, 21.1; Cl, 14.9. Calc'd for [Cu(C₁₁H₁₆N₆S]Cl₂: C, 33.1; H, 4.0; N, 21.1; Cl, 17.8). MS: m/z 326.0388=[Cu(C₁₁H₁₅N₆S]⁺= 326.0375.

Example 1E

[Cu⁽ᴵ⁾₂(L¹H₂)₂](PF₆)₂.CH₃CN

L¹H₂ (0.028 g, 0.11 mmol) was dissolved in deoxygenated dichloromethane (ca. 10 mL). [Cu(CH₃CN)]PF₆ (0.039 g, 0.11 mmol) was added causing the immediate precipitation of an orange solid. The mixture was stirred at room temperature under an atmosphere of nitrogen for 1 hour. The solid was collected by filtration under nitrogen, washed with deoxygenated dichloromethane and dried in vacuo to give [Cu₂(L¹H₂)₂] (PF₆)₂.CH₃CN as an orange powder (0.044 g, 0.044 mmol, 84%). (Found: C, 29.8; H, 3.5; N, 18.7. Calc'd for [Cu₂C₂₂H₃₂N₁₂F₁₂P₂S₂].CH₃CN: C, 29.2; H, 3.6; N, 18.5). Crystals suitable for X-ray analysis were grown by dissolving [Cu₂(L¹H₂)₂](PF₆)₂.CH₃CN (ca. 10 mg) in deoxygenated DMF (ca. 3 mL) and layering deoxygenated diethyl ether onto the orange-red solution. Red-orange crystals suitable for X-ray analysis deposited after several days and proved to be the DMF solvate, [Cu₂(L¹H₂)₂](PF₆)₂.4DMF.

Example 1F

L²H₂

Acetyl-N4-methyl thiosemicarbazone (0.920 g, 5.31 mmol) and 2-hydrazinonicotinic acid (0.813 g, 5.31 mmol) were added to ethanol (100 mL). The mixture was heated at reflux under an atmosphere of nitrogen for 4 hours. The mixture was allowed to cool to room temperature. A lemon yellow solid was collected by filtration, washed with ethanol and diethyl ether. NMR analysis showed the product contained a small amount of unreacted 2-hydrazinonictonic acid. The crude solid was suspended in water (50 mL) and heated to 60° C. A lemon yellow solid was collected by hot filtration, washed with ethanol and diethyl ether to give L²H₂ (1.059 g, 65%).

Micro ¹H NMR (500 MHz): δ 2.21, 3H, s, CH₃; 2.24, 3H, s, CH₃; 3.02, 3H, d, $^3J_{HH}$=5 Hz, NH—CH₃; 7.29, 1H, d, $^3J_{HH}$=9 Hz, ArH; 8.10, 1H, m, ArH; 8.34, 1H, m, ArH; 8.69, 1H, m, NH; 10.19, 1H, br s, NH; 10.47, 1H, br s, NH.

MS: (ve ion)/307=[Cl$_2$H, s, N$_6$O$_2$S]$^-$; (+ve ion) m/, 309=[C$_{12}$H$_{16}$N$_6$O$_2$S]$^+$.

Example 1G

[Cu(L$^2$H]Cl

L2H$_2$ (0.090 g, 0.29 mmol) and copper chloride dihydrate (0.049 g, 0.29 mmol) were suspended in ethanol (20 mL). The mixture was heated at reflux under an atmosphere of nitrogen for 2 hours. A brown precipitate was collected by filtration and washed with ethanol and diethyl ether to give [Cu(L$^2$H)] Cl. MS: (+ve ion) m/Z 370.0278=[CuC$_{12}$H$_{15}$N$_6$O$_2$S]+ =370.0273; (ve ion) m/z 368=[CuC$_{12}$H$_{13}$N$_6$O$_2$S]$^-$.

Example 1H

[Cu(L$^2$)]1

L2H$_2$ (0.206 g, 0.67 mmol) and copper acetate monohydrate (0.147 g, 0.74 mmol) were added to ethanol (20 mL). The intense purple mixture was heated at reflux under an atmosphere of nitrogen for 4 hours. The mixture was allowed to cool to room temperature. A purple precipitate was collected by filtration, and washed with ethanol and diethyl ether to give [Cu(L$^2$)] as purple powder. MS: (+ve ion) m/, 370=[CuC$_{12}$H$_{15}$N$_6$O$_2$S]$^+$; (ve ion) m/, 368=[CuC$_{12}$H$_{13}$N$_6$O$_2$S]$^-$.

Example 1I

[Cu$^{(1)}$(L$^2$H$_2$)]BF$_4$

L$^2$H$_2$ (0.050 g, 0.162 mmol) was dissolved in DMF (3 mL). The mixture was deoxygenated and [Cu(CH$_3$CN)$_4$]BF$_4$ (0.051 g, 0.162 mmol) was added. The orange-red mixture was stirred at room temperature for 1 hour. Addition of deoxygenated diethyl ether resulted in the precipitation of a red/orange solid.

Example 1J

L$^2$H—Na(tert-butoxycarbonyl -L-lysine

L$^2$H$_2$ (0.100 g, 0.32 mmol) was dissolved in DMSO (3 mL). N-Hydroxysuccinimide (0.050 g, 0.42 mmol), 1-[dim-ethylamino)propyl)]-3-ethylcarbodiimide hydrochloride (0.081 g, 0.42 mmol) and diisopropylethylamine were added and the mixture was stirred at room temperature for 20 minutes. Nα(Tert-butoxycarbonyl)-L-lysine (0.104 g, 0.42 mmol) was added and the mixture was stirred at room temperature for 24 hours. The mixture was concentrated in vacuo and addition of water resulted in the precipitation of an off-white solid. The solid was collected by filtration and washed with water, ethanol and diethyl ether. The mass spectrum of the crude product showed a peak at m/z=537 which corresponds to the coupled product, [L$^2$H—Nα(tert-butoxycarbo-nyl)-L-Lysine+H+]+ and a peak at m/z=309 corresponding to L$^2$H$_2$.

A deprotonated hydrazone in which the amide nitrogen is not coordinated to a metal centre is rare, however, X-ray crystal structural study of [Cu(L$^1$)] provided indirect evidence of this possibility; the ligand was shown to be clearly doubly deprotonated, with no evidence of a proton on the amidic nitrogen of the pyridyl hydrazone fragment. Analysis showed that the copper is 4 coordinate with the expected 5-5-5 chelate ring system. There are relatively short contacts between the Cu atom and O atoms of ClO$_4$-ions above and below the plane of the tetradentate ligand (Cu(1) . . . O(1) 2.540(6) Å, Cu(1) . . . O(5) 2.799 (13) Å, Cu(1) . . . O(15) 2.668(9) Å). The disorder of the anions suggests that these interactions have little directional character, and may be largely columbic in nature. The geometry about the copper was distorted square planar. The N(5)-Cu—N(3) bond angle (81.4(3)) is significantly smaller than the N(2)-Cu—S(1) bond angle of 87.32(19). The protonation of the thiosemicar-bazone limb of the ligand was reflected in the C(1)-S(1) bond distance (1.709(8) Å) which is indicative of thione-like character rather than the thiol-like found in [Cu(ATSM)] (1.7580 (17)) and the C(1)-N(1) distance of 1.358(10) Å which suggest more single bond character than the analogous bond in [Cu(ATSM)] (1.324(2) Å). In the mono cationic tetrafluoroborate salt of [Cu(L$^2$H)]BF$_4$ the copper was distorted square planar although there is a weak axial interaction with a sulfur from an adjacent molecule forming a centrosymmetric dimer (Cu(1) . . . S(1) 2.841 (1) Å) and the copper is slightly displaced (0.165 Å) out of the plane. The N(5)-Cu—N(3) bond angle (80.07(8)°) is again smaller than the S(1)-Cu—N(2) angle (86.33(6)°).

Cyclic voltammetry measurements in DMF with a glassy carbon electrode showed that the neutral complex [Cu(L$^1$)] undergoes a quasi-reversible reduction at $E_{1/2}$=−0.68 V (vs SCE) with a peak separation of 82 mV which is attributed to a Cu(II) to Cu(I) reduction process. The electron withdrawing carboxylate group in the neutral complex [Cu(L$^2$H)] resulted in a shift to a higher reduction potential with a quasi-reversible process at −0.56 V with a peak separation of 78 mV. Under the same conditions the hypoxia selective radiopharmaceutical [Cu(ATSM)] undergoes a reversible reduction at $E_{1/2}$=−0.59 V.

The cationic (non-deprotonated) complexes [Cu(L$^1$H$_2$)]$^{2+}$ and [Cu(L$^2$H)]Cl both exhibited electrochemically irreversible reductions at more positive potentials than their neutral analogues.

The redox potential relates to the substitution present on the diimine backbone of the complexes. Typically, complexes with one alkyl substituent have an intermediate reduction potential and complexes with no alkyl substituents, such as glyoxal based bis(thiosemicarbazones), have more positive reduction potentials. The hypoxic cell selectivity, measured after one hour from intracellular-to-extracellular concentration ratios, strongly correlates with redox potential, and in general, the higher the redox potential, the more hypoxia-selective the complex.

Addition of sodium acetate to the analyte solution resulted in a cyclic voltammogram similar to that of the neutral analogues. In the copper(I) complex [Cu$_2$(L$_1$H$_2$)$_2$](PF$_6$)$_2$ each ligand acts as a bidentate N—S donor to one Cu(I) ion and a N—N$_{pyridine}$ donor to another Cu(I) ion to generate a helical structure. The complex has no crystallographic symmetry but closely approximates to local twofold rotational symmetry. The Cu—Cu distance of 3.3344(8) Å suggests little interaction between the copper ions. Each of the ligands is twisted substantially at the C—C bond (N(2)-C(2)-C(3)-N3=45.7° and N(8)-C(13)-C(14)-N(9)=47.6°). The geometry about each Cu(I) ion is distorted tetrahedral with the Cu—N$_{pyridine}$ bond length (Cu(1)-N(11)=2.105(4) Å; Cu(2)-N(5)=2.022(4) Å) shorter than the Cu—S bond (Cu(1)-S(1)=2.2466(15); Cu(2)-S(2)=2.2569(14)). The C—S bond lengths of C(1)-S (1)=1.691(5) and C(12)-S(2)=1.697(5) again showed the ligand is more thione-like in character than thiol-like. The structure is analogous to the Cu(I) derivative of the hypoxia selective radiopharmaceutical, [Cu(ATSM)].

$L^1H_2$ and $L^2H_2$ were found to be capable of forming copper (II) complexes that can be reduced at biologically accessible potentials and copper(I) complexes of both ligands have been isolated. The Lysine-$L^2H_2$ conjugate provides an amino acid with an appended copper chelator which could be incorporated into biological targeting molecules with total site specificity via solid phase peptide synthesis as has recently been demonstrated for HYNIC.

Example Section 2

BTAP and Derivatives Thereof

Example 2A

Para-Substituted Amino-BTAP

General Procedure (1)

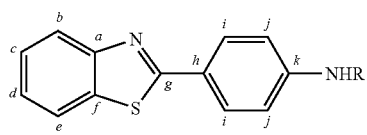

4-Aminobenzoic acid (1 eq) and polyphosphoric acid (0.5 g per mmol reactants) were placed in a twin necked round bottomed flask fitted with an overhead stirrer and the mixture heated to 180° C. 2-Aminothiophenol (1 eq) was added and the mixture was stirred under $N_2$ for 4 h. The mixture was cooled to 60-90° C. with stirring and 10% $NaCO_{3\ (aq)}$ was then added slowly until the mixture became alkaline. The resulting precipitate was collected by vacuum filtration and washed with copious amounts of $NaCO_{3(aq)}$, $H_2O$ and diethyl ether. The precipitate was purified using flash column chromatography (MeOH:$CHCl_3$, 3:97).

Example 2B

Amino-BTAP(R=H)

As per general procedure (1) using 4-aminobenzoic acid (2.74 g, 20 mmol), polyphosphoric acid (10 g) and 2-aminothiophenol (2.14 ml, 20 mmol). Amino-BTAP was isolated as a white solid (2.8 g, 61.7%). $R_f$=33.0 mins. NMR: $\delta_H$ (d$_6$-DMSO) 8.00 (1H, d, J=7.9, $C_eH$), 7.88 (2H, d, J=8.0, $C_iH$), 7.75 (2H, d, J=8.6, $C_bH$), 7.44 (1H, t, J=8.1, $C_dH$), 7.31 (1H, t, J=8.0, $C_cH$), 6.66 (2H, d, J=8.6, $C_jH$) and 6.12 (2H, S, $NH_2$). $\delta_C$(CDCl$_3$) 168.7 ($C_g$), 154.2 ($C_f$), 149.4 ($C_k$), 137.0 ($C_a$), 129.2 ($C_i$), 126.2 ($C_d$), 124.5 ($C_c$), 122.7 ($C_e$), 121.6 ($C_b$) and 114.9 ($C_j$). ES$^+$-MS: m/z=227.0636 (MH$^+$), $C_{13}H_{10}N_2S$ requires M, 226.0565. (Found: C, 69.18; H, 4.58; N, 12.34%. $C_{13}H_{10}N_2S$ requires C, 69.08; H, 4.46; N, 12.39%). The data is consistent with previously published work (Klunk, W. E., et al., *Life Sciences*, 2001, 69, p. 1471-84).

Example 2C

Me-Amino-BTAP(R=Me)

As per general procedure (1) using 4-methylaminobenzoic acid (2.83 g, 18.7 mmol), polyphosphoric acid (10 g) and 2-aminothiophenol (2.0 mL, 18.7 mmol). Me-Amino-BTAP was isolated as a pale yellow solid (2.2 g, 51.2%). NMR: $\delta_H$(CDCl$_3$) 7.95 (1H, d, J=8.0, $C_eH$), 8.75 (2H, d, J=8.7, $C_iH$), 7.77 (1H, d, J=8.4, $C_bH$), 7.36 (1H, t, J=8.1, $C_dH$), 7.23 (1H, t, J=8.1, $C_dH$), 6.57 (2H, d, J=8.8, $C_jH$) and 2.84 (3H, s, $CH_3$). ES$^+$-MS: m/z=241.0789 (MH$^+$), $C_{14}H_{12}N_2S$ requires M, 240.0721. The data is consistent with previously published work (Klunk, W. E., et al., *Life Sciences*, 2001, 69, p. 1471-84).

Example 2D

Benzylamino-BTAP

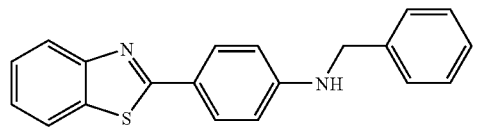

Amino-BTAP (0.3 g, 1.3 mmol) and benzyl bromide (0.17 g, 1.3 mmol) were dissolved in EtOH (10 mL), stirred and heated at reflux temperature for 3 h then stirred at room temperature for a further 21 h. $H_2O$ was added and the resultant precipitate collected by gravity filtration. The residue was recrystallised from hot EtOH (0.03 g, 6%) NMR: $\delta_H$(d$_6$-DMSO) 8.03 (1H, d, J=7.3, ArH), 7.96 (1H, d, J=7.4, ArH), 7.80-7.60 (7H, m, ArH), 7.34 (1H, t, J=8.0, $C_{c/d}H$), 7.27 (1H, t, J=8.2, ArH), 6.88 (2H, d, J=8.6, ArH) and 3.39 (2H, s, $CH_2$). ES$^+$-MS: m/z=315.0576 (MH$^+$), $C_{20}H_{16}N_2S$ requires M, 314.0687.

Example 2E

4-Nitrophenylamido-BTAP

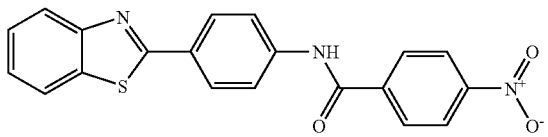

Amino-BTAP (0.37 g, 1.6 mmol), 4-nitrobenzoylchloride (0.30 g, (1.6 mmol) and DIPEA (0.211 g, 1.6 mmol) were dissolved in $CH_2Cl_2$ (15 mL). The solution was stirred overnight and the solvent was removed under vacuum (0.3 g, 50%). $R_f$=28.0 mins, ES$^+$-MS: m/z=376.0738 (MH$^+$), $C_{20}H_{13}N_3O_3S$ requires MH$^+$, 376.0756.

Example 2F

4-Aminophenylamido-BTAP 4-nitro-N-(4

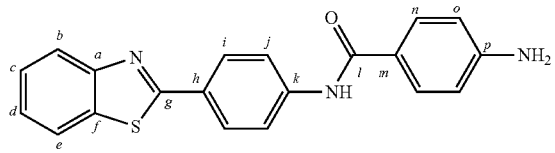

benzothiazol-2-yl)phenylbenzamide (0.2 g, 0.8 mmol) was dissolved in ethanol (30 mL), SnCl$_2$ (0.4 g, 1.8 mmol) was added and the solution was refluxed under N$_2$ for 4 h. The solvent was then removed under vacuum. The residue was dissolved in ethyl acetate (30 ml) and washed with 1M NaOH$_{(aq)}$ (3×30 ml) and H$_2$O (3×30 ml). The solvent was removed under vacuum to give the desired product. (0.19 g, 68.8%) R$_f$=38.5 mins NMR: $\delta_H$(d$_6$-DMSO) 10.07 (1H, s, NHC=O), 8.11 (1H, d, J=7.8, ArH), 8.04 (2H, d, J=8.9, ArH), 7.97 (2H, d, J=8.9, ArH), 7.85 (2H, d, J=7.7, ArH), 7.50 (1H, t, J=7.9, ArH), 7.42 (1H, t, J=7.9, ArH), 6.65 (1H, d, J=8.0, ArH), 6.59 (2H, d, J=8.6, ArH) and 5.83 (2H, s, NH$_2$). $\delta_C$ (DMSO) 167.9 (C$_g$), 161.2 (C$_m$), 155.7 (C$_f$), 153.4 (C$_1$), 143.8 (C$_h$), 134.4 (C$_a$), 130.8 (C$_n$), 129.0 (C$_j$), 128.2 (C$_o$), 126.7 (C$_k$), 126.4 (C$_d$), 125.0 (C$_c$), 122.9 (C$_b$), 22.5 (C$_e$), 120.6 (C$_i$) and 114.5 (C$_p$). $\lambda_{max}$(DMSO)=416 nm. ES$^+$-MS: m/z=346.1003 (MH$^+$), C$_{20}$H$_{15}$N$_3$OS requires MH$^+$, 346.1014. (Found: C, 69.50; H, 4.65; N, 12.29%. C$_{20}$H$_{15}$N$_3$OS requires C, 69.56; H, 4.34; N, 12.13%).

Example 2G

Bromoacetylamide-BTAP

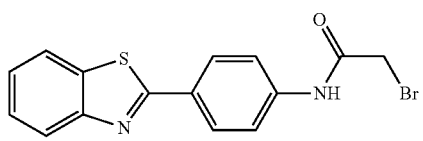

Amino-BTAP (0.27 g, 1.2 mmol) and DIPEA (0.20 ml, 1.2 mmol) were dissolved in CH$_2$Cl$_2$ (15 mL), the flask was degassed with N$_2$ and cooled to −97° C. 2-Bromoacetylbromide (0.10 ml, 1.2 mmol) was added, and the reaction mixture allowed to reach room temperature and was then stirred overnight. The mixture was washed with H$_2$O (2×100 ml), 0.1 M HCl$_{(aq)}$ (2×100 ml) and H$_2$O (1×100 ml). The organic layer was dried over K$_2$CO$_3$ and solvent then removed under reduced pressure. (0.24 g, 58%) R$_f$ 46 mins. NMR: $\delta_H$ (CDCl$_3$) 8.82 (1 H, s, NHC=O), 7.91 (1H, d, ArH), 7.81 (2H, d, ArH), 7.35 (1H, d, J=7.3, ArH), 7.25 (1H, t, ArH), 7.19 (1H, t, ArH), 6.66 (2H, d, ArH) and 4.11 (2H, s, CH$_2$). ES$^+$-MS: m/z=346.9870 (MH$^+$), C$_{20}$H$_{13}$N$_3$O$_2$S requires MH$^+$, 346.9854.

Example 2H

Pyridinoethylamide-BTAP

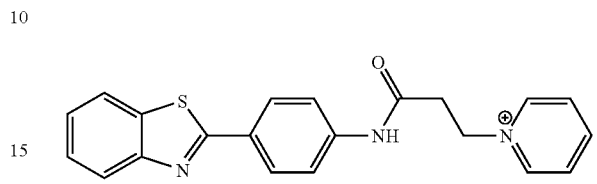

Amino-BTAP (0.14 g, 0.6 mmol) and 3-bromopropionyl chloride (0.11 g, 0.6 mmol) were dissolved pyridine (4 mL) and heated at reflux temperature for 2 h. Pyridine was removed under reduced pressure to afford a residue which was dissolved in chloroform and washed with 0.1 M HCl$_{(aq)}$ and H$_2$O (2×20 ml) (0.02 g, 10%). NMR: $\delta_H$ (DMSO) 8.96 (1H, s, NHC=O), 8.73 (2H, d, J=7.4, PyH), 8.51 (1H, t, J=7.45, PyH), 8.25-8.22 (3H, m, ArH+PyH), 8.05 (1H, d, J=ArH), 7.57 (2H, d, J=7.98, ArH), 7.53 (1H, t, J=8.06, ArH), 7.48 (1H, t, J=8.00, ArH), 7.27 (2H, d, J=7.90, ArH) and 2.61 (2H, s, CH$_2$). MS: m/z=360.0991 (MH$^+$), C$_{21}$H$_{18}$N$_3$ requires MH$^+$, 360.0912.

Example 2I

Ala-Amido-BTAP

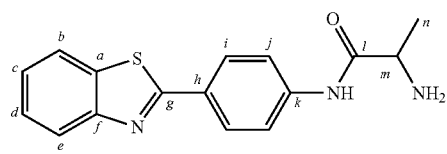

Amino-BTAP (0.2 g, 0.9 mmol) was dissolved in dichloromethane (20 mL) and stirred at room temperature. To this solution was added 1-ethyl-3-(3'-(dimethylamino)-propyl)carbodiimide-HCl (0.5 g, 0.3 mmol), 1-hydroxybenzotriazole (HOBt) (0.04 g, 0.3 mmol), and Boc protected alanine (0.03 g, 2.3 mmol). The mixture was stirred for 24 h, a further 0.3 mmol of each reactant was added, and stirring continued for a further 24 h. This step was repeated twice more and stirring continued for a further 3 days until a clear solution resulted. The solvent was removed under reduced pressure and the resultant oil purified by column chromatography (MeOH:CHCl$_3$, 1:99) was then dissolved in dichloromethane acidified with trifluoroacetic acid (0.1 ml) and stirred for 3 h. The resultant precipitate was collected by gravity filtration and washed with CH$_2$Cl$_2$ to give the desired product as the trifluoroacetic acid a cream crystalline solid. (0.17 g, 55%) R$_f$=129.0 mins NMR: $\delta_H$ (CDCl$_3$) 10.09 (1H, s, NHC=O), 8.55 (3H, s, NH$_3^+$), 8.29 (1H, d, J=8.8, ArH), 8.20-7.90 (3H, m, ArH), 7.36 (1H, t, J=7.5, ArH), 7.25 (2H, d, J=7.6, ArH), 3.74 (1H, q, ArH) and 1.13 (3H, s, CH$_3$). $\delta_C$ (CDCl$_3$) 171.4 (C$_l$), 167.6 (C$_g$), 153.976 (C$_f$), 140.4 (C$_k$), 129.138 (C$_a$), 128.2 (C$_h$), 126.1 (C$_i$), 124.8 (C$_j$), 124.4 (C$_c$), 122.8 (C$_d$), 121.4 ($C_b$), 119.6 ($C_e$), 28.3 ($C_n$) and 17.6 ($C_m$). MS: m/z=298.0929 (MH$^+$), $C_{16}H_{15}N_3OS$ requires MH$^+$, 298.0902.

Example 2J

Mono-Substituted Phenylimino-BTAP

General Procedure (2)

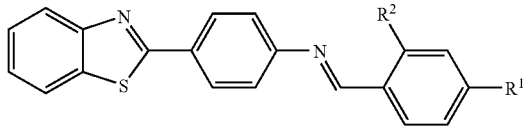

Amino-BTAP (1 eq) and $R^1,R^2$-benzaldehyde (1 eq) were dissolved in methanol and heated at reflux temperature for 5 hours. The resulting precipitate was isolated by gravity filtration and washed with ethanol, water and diethyl-ether.

Example 2K

2-Nitrophenylimino-BTAP $R^1$=H, $R^2$=NO$_2$

As per general procedure (2) using Amino-BTAP (0.19 g, 0.8 mmol), 2-nitrobenzaldehyde (0.13 g, 0.8 mmol) and methanol (15 ml). 2-Nitrophenylimino-BTAP was isolated as a dark yellow solid (0.24 g, 81.0%) NMR: $\delta_H$(d$_6$-DMSO) 8.95 (1H, s, CH=N), 8.40-8.20, (5H, m, ArH), 8.06 (1H, d, J=7.6, ArH), 7.90 (1H, t, J=7.3, ArH), 7.79 (1H, t, J=7.8, ArH), 7.54 (1H, t, J=7.9, ArH) and 7.45-7.30 (3H, m, ArH). ES$^+$-MS: m/z=360.0810 (MH$^+$), $C_{20}H_{14}N_3O_2S$ requires MH$^+$, 360.0807.

Example 2L

4-Nitrophenylimino-BTAP $R^1$=NO$_2$, $R^2$=H

As per general procedure (2) using Amino-BTAP (0.20 g, 0.9 mmol), 4-nitrobenzaldehyde (0.13 g, 0.9 mmol) and methanol (15 ml). 4-Nitrophenylimino-BTAP was isolated as a yellow solid. (0.27 g, 86.2%) NMR: $\delta_H$(d$_6$-DMSO) 8.90 (1H, s, CH=N), 8.34, (2 H, d, J=8.6, ArH), 8.27-8.15 (5H, m, ArH), 8.08-8.03 (1H, t, J=7.9, ArH) and 7.49-7.36 (4 H, m, ArH). ES$^+$-MS: m/z=360.0800 (MH$^+$), $C_{20}H_{14}N_3O_2S$ requires MH$^+$, 360.0807.

Example 2M

4-Aldehydophenylimino-BTAP $R^1$=O$_2$, $R^2$=H

As per general procedure (2) using Amino-BTAP (0.50 g, 2.2 mmol), terephthalaldehyde (1.45 g, 11.0 mmol) and methanol (20 ml). 4-aldehydophenylimino-BTAP was isolated as a cream solid (0.67 g, 88.7%) R$_f$=24 minutes. NMR: $\delta_H$(d$_6$-DMSO) 10.10 (1 H, s, CH=O), 8.58 (1H, s, CH=N), 8.15, (2H, d, J=8.4, ArH), 8.12-8.04 (4H, m, ArH), 8.00 (1H, d, J=8.1, ArH), 7.49 (1H, d, J=7.4, ArH) and 7.45-7.30 (4H, m, ArH). $\delta_C$ (CDCl$_3$) 191.96 ($C_q$), 167.12 ($C_g$), 159.37 ($C_l$), 154.162 ($C_f$), 153.52 ($C_k$), 140.95 ($C_m$), 138.92 ($C_p$), 135.02 ($C_a$), 131.89 ($C_h$), 130.06 ($C_n$), 129.45 ($C_o$), 128.63 ($C_i$), 126.42 ($C_c$), 125.24 ($C_d$), 123.16 ($C_e$), 121.63 ($C_j$) and 121.60 ($C_b$). ES$^+$-MS: m/z=343.0330 (MH$^+$), $C_{21}H_{14}N_2OS$ requires MH$^+$, 343.0390.

Example 2N

Phenylimino-BTAP $R^1$=H, $R^2$=H

As per general procedure (2) using Amino-BTAP (0.20 g, 0.9 mmol), benzaldehyde (0.9 ml, 0.9 mmol) and methanol (10 ml). Phenylimino-BTAP was isolated as a yellow solid. (0.014 g, 5.0%) NMR: $\delta_H$(d$_6$-DMSO) 8.53 (1H, s, CH=N), 8.10 (1H, d, J=7.9, ArH), 8.00 (1H, d, J=8.1, ArH), 7.88 (2H, d, J=8.1, ArH), 7.84 (2H, d, J=8.1, ArH), 7.78 (2H, t, J=8.2, ArH), 7.54 (1H, t, J=8.1, ArH), 7.51 (2H, m, J=8.0, ArH), and 7.45 (2H, d, J=8.2, ArH). ES$^+$-MS: m/z=314.0921 (MH$^+$), $C_{20}H_{14}NS$ requires MH$^+$, 314.1002.

Example 2O

2-Hydroxyphenylimino-BTAP $R^1$=H, $R^2$=OH

As per general procedure (2) using Amino-BTAP (0.20 g, 0.9 mmol), benzaldehyde (1.1 g, 0.9 mmol) and methanol (10 mL). 2-Hydroxyphenylimino-BTAP was isolated as a yellow solid (0.017 g, 20.0%). NMR: $\delta_H$ (d$_6$-DMSO) 9.75 (1H, s, OH), 8.23 (1H, d, J=7.33, ArH), 8.10 (2H, d, J=8.09, ArH), 7.85 (2H, d, J=7.9, ArH), 7.65 (2H, d, J=8.1, ArH), 7.78 (2H, d, J=8.2, ArH), 7.54 (1H, t, J=8.1, ArH), 7.51 (H, t, J=8.0, ArH) and 7.45 (2 H, d, J=8.2, ArH). ES$^+$-MS: m/z=330.0871 (MH$^+$), $C_{20}H_{14}NS$ requires MH$^+$, 330.1050.

Example 2P

Hydrazino-BTAP

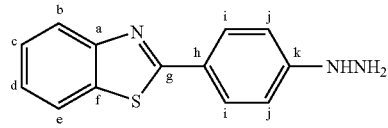

As per general procedure (1) using 4-hydrazinobenzoic acid (0.60 g, 4.0 mmol), polyphosphoric acid (3 g) and 2-aminothiophenol (0.40 ml, 4.0 mmol). Hydrazino-BTAP was isolated as a brown solid and immediately stored under N$_2$. (0.09 g, 10%). NMR: $\delta_H$ (d$_6$-DMSO) 7.99 (1H, d, J=7.7, $C_e$H), 7.89 (1H, d, J=7.8 $C_e$H), 7.80 (2H, d, J=8.7, $C_j$H), 7.51 (1H, s, NH), 7.43 (1H, t, J=7.2, $C_d$H), 7.33 (1H, t, J=7.1, $C_c$H), 6.87 (2H, d, J=8.7, $C_j$H) and 5.46 (2H, br s, NH$_2$). $\delta_C$ (DMSO) 169.7 ($C_g$), 153.8 ($C_f$), 149.7 ($C_k$), 136.5 ($C_a$), 127.2

($C_i$), 127.0 ($C_d$), 125.5 ($C_c$), 123.1 ($C_e$), 120.9 ($C_b$) and 113.3 ($C_j$). ES$^+$-MS: m/z=242.0764 (MH$^+$), $C_{13}H_{11}N_3S$ requires MH$^+$, 242.0752.

Example 2Q

Hydrazino-BTAP-butadione

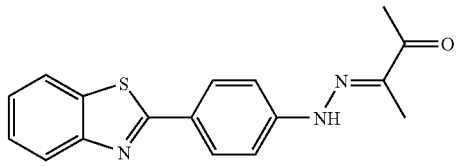

Hydrazino-BTAP (0.374 g, 1.6 mmol) was dissolved in H$_2$O (5 mL) and cooled to 10° C. Butadi-2,3-one was added and the solution was stirred to room temperature over 0.5 h. The desired product was isolated by gravity filtration and dried by at 40° C. under reduced pressure. (0.25 g, 51%). NMR: $\delta_H$(d$_6$-DMSO) 8.10-7.74 (5H, m, ArH+NH), 7.42 (1H, t, J=7.7, ArH), 7.2 (1H, t, J=8.0, ArH), 6.67 (1H, d, J=8.1, ArH), 2.88 (3H, s, Me) and 2.81 (3H, s, Me). MS: m/z=310.1004 (MH$^+$), $C_{17}H_{15}N_3OS$ requires MH$^+$, 310.1014.

Example 2R

Diamino-BTAP

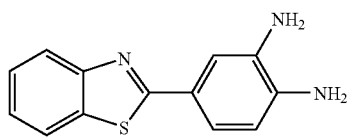

As per general procedure (1) using 3,4-diaminobenzoic acid (1.00 g, 6.5 mmol), polyphosphoric acid (4 g) and 2-aminothiophenol (0.70 ml, 6.5 mmol). Diamino-BTAP was isolated as a green solid (0.2 g, 16%). NMR: $\delta_H$ (CDCl$_3$) 7.92 (1H, d, J=8.1, ArH), 7.78 (1 H, d, J=7.9 ArH), 7.46 (1H, s, ArH), 7.37 (1H, d, J=8.0, ArH), 7.25 (1H, t, J=7.1, ArH), 7.08 (1H, d, J=7.5, ArH), 6.52 (1H, d, J=7.1, ArH), 5.20 (2H, br S, NH$_2$) and 4.83 (2H, br s, NH$_2$) $\delta_C$ (CDCl$_3$) 169.5, 155.2, 139.8, 135.0, 134.3, 127.1, 124.8, 123.1, 122.9, 122.7, 119.6, 114.2 and 113.5. MS: m/z=242.0761 (MH$^+$), $C_{13}H_{11}N_3S$ requires MH$^+$, 242.0752.

Example 2S

Diaminophenylimidazole-BTAP

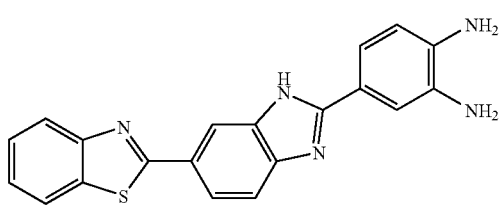

This is an insoluble by product of the reaction. (0.15 g, 6.4%) NMR: $\delta_H$(d$_6$-DMSO) 12.55 (1H, br s, NH), 7.95 (1H, d, J=7.6, ArH), 7.86 (4H, m, ArH), 7.44 (1H, d, J=7.5, ArH), 7.36 (1H, t, J=7.4, ArH), 7.30 (1H, s, ArH), 7.09 (1H, d, J=8.0, ArH), 6.45 (1H, d, J=8.0, ArH), 4.92 (2H, br s, NH$_2$) and 4.58 (2H, br s, NH$_2$). ES$^+$-MS: m/z=358.1170 (MH$^+$), $C_{20}H_{15}N_5S$ requires MH$^+$, 357.3735.

Example Section 3

2,3-butadione-N4-alkylthiosemicarbazones

Example 3A 2,3-butadione-N4-alkylthiosemicarbazones

General Procedure (3)

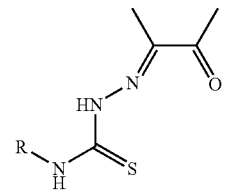

Alkylthiosemicarbazide (1 eq) was dissolved in water and the resulting solution was treated with 10% HCl (aq) (1 eq). The solution was cooled to 10° C. Butane-2,3-dione (1.1 eq) was added and the solution was left to stir in an ice bath for 10 minutes. A solid precipitated out of the solution, which was collected by gravity filtration, washed with copious amounts of ice cold water followed by a small amount of di-ethyl ether and dried overnight in vacuo at 55° C. to give 2,3-butadione-N4-alkylthiosemicarbazones.

Example 3B 2,3-butadione-N4-methylthiosemicarbazone (1)

As per general procedure (3) using methylthiosemicarbazide (1.09 g, 10.4 mmol), water (10 ml), HCl (1 ml) and butane-2,3-dione (1 ml, 11.4 mmol). (1) was isolated as a fluffy white solid (1.96 g, 71%). The full characterisation of the product by $^1$H and $^{13}$C NMR, ES$^+$-MS and elemental analysis was consistent with reported values. (Found: C, 40.93; H, 6.45; N, 24.37. $C_6H_{11}N_3OS$ requires C, 41.61; H, 6.35; N, 24.28%).

Example 3C 2,3-butadione-N4-ethylthiosemicarbazone (2)

As per general procedure (3) using ethylthiosemicarbazide (0.3 g, 2.5 mmol), water (1.5 ml), HCl (0.2 ml) and butane-2,3-dione (0.24 g, 2.8 mmol). (2) was isolated as a fluffy cream solid (0.28 g, 62%). The full characterisation of the product by $^1$H and $^{13}$C NMR, ES$^+$-MS and elemental analysis was consistent with reported values. (Found: C, 42.65; H, 6.44; N, 22.98%. $C_7H_{13}N_3OS$ requires C, 44.89; H, 6.99; N, 22.44%).

Example 3D

2,3-butadione-thiosemicarbazone (3)

As per general procedure (3) using thiosemicarbazide (1 g, 11.0 mmol), water (10 ml), HCl (1 ml) and butane-2,3-dione (1 ml, 12.1 mmol). (3) was isolated as a white solid (0.8 g, 45.7%). The full characterisation of the product by $^1$H and $^{13}$C NMR, ES$^+$-MS and elemental analysis was consistent with reported values. (Found: C, 36.45; H, 5.88; N, 25.86%. $C_5H_9N_3OS$ requires C, 37.78; H, 5.71; N, 26.42%).

Example 3E

2,3-butadione-N4-phenylthiosemicarbazone (4)

As per general procedure (3) using phenylthiosemicarbazide (1.90 g, 11.4 mmol), water (10 ml), HCl (1 ml) and butane-2,3-dione (1 ml, 12.1 mmol). The full characterisation of the product by $^1$H and $^{13}$C NMR, ES$^+$-MS and elemental analysis was consistant with reported values. (Found: C, 56.41; H, 5.42; N, 17.73%. $C_{11}H_{13}N_3OS$ requires C, 56.22; H, 5.54; N, 17.88%).

Example Section 4

ATS(R)/P-Carb and its Derivatives and Complexes

Example 4A

ATS(R)/P-Carb

General Procedure (4)

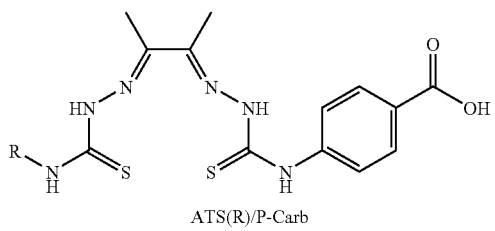

ATS(R)/P-Carb (4-carboxyphenyl)-3-thiosemicarbazide (1 eq) was dissolved in DMF and the resulting solution was treated with glacial acetic acid (1 eq). The solution was warmed to 45° C. under a $N_2$ atmosphere and 2,3-butadione-N4-alkylthiosemicarbazone was added. The solution was stirred at 45° C., under $N_2$ atmosphere for 4 h. Half the DMF was removed on the rotary evaporator. Water was added dropwise until no further solid precipitated. The solid was collected by filtration, washed with a small amount of diethyl-ether and dried overnight in vacuo at 55° C. to give 2,3-butadione-N4-(4-carboxyphenyl)-N4-(alkyl)bis(thiosemicarbazone).

Example 4B

ATS(Me)/P-Carb, R=Me

As per general procedure (4) using 4(4-carboxyphenyl)-3-thiosemicarbazide (0.61 g, 2.9 mmol), DMF (10 ml), acetic acid (0.15 ml, 2.9 mmol) and (1) (0.5 g, 2.9 mmol). ATS(e)/P-carb was isolated as a pale yellow solid (0.92 g, 87%). NMR: $\delta_H$(d$_6$-DMSO) 10.81 (1H, s, NH Ar ring side), 10.38 (1H, s, NH), 10.11 (1H, s, NHPh), 8.40 (1H, t, NHMe), 8.92 (4H, m, aromatic protons), 3.05 (3H, d, NHCH$_3$), 2.30 (3H, s, CH$_3$) and 2.22 (3H, s, CH$_3$). $\delta_C$ (d$_6$-DMSO) 179.7 and 179.0 (C=S), 167.8 (C=O), 150.6 and 148.2 (C=N), 144.0 (C$_d$), 130.3 (C$_c$), 124.5 (C$_a$), 122.8 (C$_b$), 32.0 (NHCH$_3$) and 13.1 and 13.6 (CH$_3$). ES$^+$-MS: m/z=367.1049 (MH$^+$), $C_{14}H_{18}N_6O_2S_2$ requires MH$^+$, 367.4682.

Example 4C

ATS(Et)/P-Carb, R=Et

As per general procedure (4) using 4(4-carboxyphenyl)-3-thiosemicarbazide (0.59 g, 2.8 mmol), DMF (10 ml), acetic acid (0.14 ml, 2.8 mmol) and (2) (0.5 g, 2.8 mmol). ATS(Et)/P-carb was isolated as a pale yellow solid (0.89 g, 88%). NMR: $\delta_H$(d$_6$-DMSO) 10.80 (1H, s, NH Ar ring side), 10.32 (1H, s, NH), 10.11 (1H, s, NHPh), 8.42 (1H, t, NHMe), 7.95 (2H, d, J=8.0, C$_b$H), 7.82 (2H, d, J=8.0, C$_c$H), 3.61 (2H, q, CH$_2$CH$_3$), 2.28 (3H, s, CH$_3$), 2.22 (3H, s, CH$_3$) and 1.11 (3H, t, CH$_2$CH$_3$) ES$^+$-MS: m/z=381.1097 (MH$^+$), $C_{15}H_{20}N_6O_2S_2$ requires MH$^+$, 381.1089. (Found: C, 43.3; H, 4.93; N, 19.7%. $C_{15}H_{20}N_6O_2S_2$ requires C, 47.4; H, 5.30; N, 22.1%).

Example 4D

ATS(H)/P-Carb, R=H

As per general procedure (4) using 4(4-carboxyphenyl)-3-thiosemicarbazide (0.49 g, 2.3 mmol), DMF (10 ml), acetic acid (0.10 ml, 2.3 mmol) and (3) (0.37 g, 2.3 mmol). ATS(H)/P-carb was isolated as a pale yellow solid (0.55 g, 70%). NMR: $^8$H (d$_6$-DMSO) 10.80 (1H, s, NH Ar ring side), 10.34 (1H, s, NH), 10.13 (1H, s, NHPh), 8.45 (1H, t, NH$_2$), 7.91 (2H, d, J=8.64 Hz, C$_b$H), 7.77 (2H, d, J=8.66 Hz, C$_c$H), 2.22 (3H, s, CH$_3$) and 2.23 (3H, s, CH$_3$). $\delta_C$ (d$_6$-DMSO) 179.4 and 176.8 (C=S), 167.4 (C=O), 150.4 and 148.5 (C=N), 143.5 (C$_d$), 129.9 (C$_c$), 127.4 (C$_a$), 124.7 (C$_b$), 12.5 and 12.3 (CH$_3$). ES$^+$-MS: m/z=353.0881 (MH$^+$), $C_{13}H_{16}N_6O_2S_2$ requires MH$^+$, 353.0776. (Found: C, 42.59; H, 4.00; N, 20.93%. $C_{13}H_{16}N_6O_2S_2$ requires C, 44.3; H, 4.5; N, 23.8%).

Example 4E

ATS(Ph)/P-Carb, R=Ph

As per general procedure (4) using 4(4-carboxyphenyl)-3-thiosemicarbazide (0.44 g, 2.1 mmol), DMF (10 ml), acetic acid (0.12 ml, 2.1 mmol) and (4) (0.5 g, 2.1 mmol). ATS(Ph)/P-carb was isolated as a pale yellow solid (0.60 g, 67%). NMR: $\delta_H$ (d$_6$-DMSO) 10.90 (1H, s, NH Ar ring side), 10.19 (1H, s, NH), 9.98 (1H, s, NHPh-carb), 9.43 (1H, t, NHPh), 8.92 (2H, d, J=Hz, C$_x$H), 8.81 (2H, d, J=Hz, C$_y$H), 7.66 (2H, d, J=Hz, C$_b$H), 7.38 (2H, t, J=Hz, C$_c$H), 7.20 (1H, t, J=Hz, C$_d$H), 2.30 (3H, s, CH$_3$) and 2.13 (3H, s, CH$_3$). ES$^+$-MS: m/z=429.0719 (MH$^+$), $C_{19}H_{20}N_6O_2S_2$ requires MH$^+$, 429.1089.

Example 4F

[Cu(ATS{Me}/P-p-carb)]

General Procedure (4a)

$H_2$ATS{Me}/P-p-carb (0.05 g, 0.14 mmol) and copper acetate (0.027 g, 0.014 mmol) were added to methanol (2 mL). The mixture was heated at reflux for 2 hours under an atmosphere of nitrogen and allowed to cool slowly to room temperature. A powder formed and was collected by filtration, washed with diethyl ether and dried in vacuo to [CU(ATS{Me}/P-p-carb)] as a red/brown powder (0.047 g, 81%). UV-VIS: λ/nm (ϵ/M-1 cm-1): 268 (6142), 313 (7833), 368 (5193), 484 (2696). MS: m/z 426={[Cu(ATS{Me}/P-p-carb)]—H$^+$}.

Example 4G

[Cu(ATS{Me}/P-p-carb) methyl ester]

[Cu(ATS{Me}/P-p-carb)] (0.037 g, 0.086 mmol) was added to dry methanol (5 mL) and trifluoromethanesulfonic acid (1 drop) was added. The mixture was heated at reflux under an atmosphere of nitrogen for 35 h and allowed to cool slowly to room temperature. A brown powder formed and was collected by filtration and washed with diethyl ether to give [Cu(ATS{Me}/P-p-carb) methyl ester] as a green/brown solid (0.28 g, 74%). MS: m/z 442 {[Cu(ATS{Me}/P-p-carb) methyl ester]+H$^+$}.

Example 4H

[Ni(ATS{Me}/P-p-carb)]

As per general procedure (4a) except with H$_2$ATS{Me}/P-p-carb (0.10 g, 0.27 mmol) and nickel acetate (0.068 g, 0.27 mmol) in methanol (3 mL). [Ni(ATS{Me}/P-p-carb)] was isolated as a dark green powder (0.087 g. 75%). $^1$H NMR (DMSO-d$^6$): δ 1.88 and 2.07, 3H, s, CH$_3$; 2.80, 3H, m, NHCH$_3$; 7.64, 2H, m, CH$_b$; 7.81, 2H, m, CH$_c$; 8.19, broad hump, assume NHCH$_3$; 10.10, H, s, NHPh. $^{13}$C NMR: δ 14.0 and 15.2, CH$_3$; 32.4, NHCH$_3$; 119.0, C$_b$; 124.5, C$_a$; 130.1, C$_c$; 144.1, C$_d$; 155.0 and 161.0, C=N, 167.0; C=O; 172.7 and 177.0, C=S. MS: m/z 423=[Ni(ATS{Me}/P-p-carb)+H$^+$]. Crystals suitable for single crystal X-ray crystallography were grown from a DMF/diethyl ether solution.

Example 4I

[Ni(ATS{Me}/P-p-carb) methyl ester]

As per the procedure described in Example 4G except with [Ni(ATS{Me}/P-p-carb)] (0.045 g, 0.11 mmol). [Ni(ATS{Me}/P-p-carb) methyl ester] was isolated as a light brown powder (0.036 g, 77%). MS: m/z 437=[Ni(ATS{Me}/P-p-carb) methyl ester)+H$^+$].

Example 4J

[Zn(ATS{Me}/P-p-carb)]

As per general procedure except with H$_2$ATS{Me}/P-p-carb (0.050 g, 0.14 mmol) and zinc acetate (0.030 g, 0.14 mmol) in methanol (2 mL). [Zn(ATS{Me}/P-p-carb)] was isolated as a bright yellow powder (0.047 g, 80%). $^1$H NMR (DMSO-d$^6$): δ 2.24 and 2.34, 3H, s, CH$_3$; 2.82, 3H, m, NHCH$_3$; 7.42, H, broad hump, assume NHCH$_3$; 7.81, 4H, m, Ar; 9.62, H, s, assume NHPh; 12.19, broad hump, OH. $^{13}$C NMR: δ 14.2 and 15.1, CH$_3$; 29.6, NHCH$_3$; 112.9, assume C$_a$ (based on H$_2$ ATS{Me}/P-p-carb); 119.5, C(H); 130.8, C(H); 131.8, assume C$_a$; 145.0 and 150.9, C=N, 168.6, broad hump, assume C=O; 173.0, assume C=S; 166.9, broad hump, assume C=S. MS: m/z 427=[Zn(ATS{Me}/P-p-carb)-H$^+$].

Example 4K

[Zn ATS{Me}/P-p-carb (methyl ester)]

As per the procedure described in Example 4G except with [Zn(ATS{Me}/P-p-carb)] (0.060 g, 0.14 mmol). [Zn(ATS{Me}/P-p-carb methyl ester)] was isolated as an orange solid. MS: m/z 443=[Zn(ATS{Me}/P-p-carb methyl ester)+H$^+$].

Example 4L

ATS{Me}/P-p-carb-ONSu

ATS{Me}/P-p-carb (0.120 g, 0.3 mmol) and N-hydroxysuccinimide (0.0345 g, 0.3 mmol) were dissolved in dry DMF (1 mL) and chilled in an ice-bath. DIC (0.055 mL, 0.35 mmol) was added and the reaction mixture stirred for 3 h, allowing it to warm slowly to room temperature over 0.5 h. The resultant orange solution was analysed by RP HPLC and ES LC/MS and shown to contain the desired component. The major peak was eluted at 37 min. MS: m/z 464=[ATS{Me}/P-p-carb-ONSu+H$^+$, 100%], 367=[H$_2$ ATS{Me}/P-p-carb+H$^+$, 30%]. The solution was used without further purification.

Example 4M

ATS{Me}/P-p-carb-Lys(Boc)-OH

H-Lys(Boc)-OH (0.074 g, 0.3 mmol) was dissolved in a mixture of DMF (1 mL) and water (0.5 mL) and basified by the addition of DIPEA (104 uL, 0.6 mmol). To this was added a solution of ATS{Me}/P-p-carb-ONSu (0.15 mmol) in DMF (0.5 mL) and the mixture agitated for 16 h with a gentle vortex action. The reaction mixture was evaporated to dryness, redissolved in acetic acid/acetonitrile/water (1/5/4), applied to a preparative HPLC column and eluted with the following gradient (minutes, % B): 0, 5:10, 5; 20, 20:80, 50; 90, 100. (A=0.1% TFA, B=90% acetonitrile/10% water/0.1% TFA, flow rate=10 mL min$^{-1}$, detection 214 nm). Two major peaks were eluted at 35 and 81 min, the latter fraction was freeze dried to give ATS{Me}/P-p-carb-Lys(Boc)-OH as a cream powder (0.0035 g, 2%). Analytical HPLC R$_f$=35 min. MS: m/z 95=ATS{Me}/P p-carb-Lys(Boc)-OH+H$^+$, 100%], [H-Lys(Boc)-OH+H$^+$, 15%]. Single mass analysis C$_{25}$H$_{39}$N$_8$O$_5$S$_2$ mass=595.2489, calc. mass=595.2485; C$_{25}$H$_{38}$N$_8$O$_5$NaS$_2$ mass=617.2310, calc. mass=617.2304.

Example 4N

ATS{Me}/P-p-carb-Orn(Boc)-OH

As per the procedure described in Example 4M except with Orn(Boc)-OH (0.0697 g, 0.3 mmol). The product was purified by preparative HPLC and two major peaks were eluted at 37 min and 78 min. The latter fraction was freeze dried to give the product as a cream powder (0.0052 g, 3%). Analytical HPLC R$_f$=35 min. MS: m/z 581=[ATS{Me}/P-p-carb-Orn(Boc)-OH+H$^+$, 100%], [H$_2$ATS{Me}/P-p-carb++, 100%]. Single mass analysis C$_{24}$H$_{36}$N$_8$O$_5$NaS$_2$ mass=603.2164, calc. mass=603.2148.

Example 4O

ATS{Me}/P-p-carb-Lys-OH

Solid phase synthesis was performed in a nitrogen bubbler apparatus on a Wang resin (Fmoc-Lys(Boc)-resin) using standard techniques. Thus, the Fmoc protecting group was removed by treatment with 20% piperidine in DMF (10 mL for 3 min., 15 mL for 20 min.) and then washed thoroughly with DMF (5×10 mL), DCM (3×10 mL) and DMF (3×10 mL). After draining, a solution of $H_2ATS\{Me\}$/P-p-carb (0.092 g, 0.25 mmol, 5 equivalents) and HOBt (0.038 g, 0.25 mmol) in dry DMF (1 mL) was added and the mixture agitated by nitrogen gas. DIC (50 uL, 0.32 mmol) was added and the mixture agitated for 16 h at room temperature. A resin sample after this period gave a negative Kaiser ninhydrin test indicating completion of the reaction. The resin was drained, washed with DMF, DCM and DMF as described above and after a final wash with diethyl ether, was dried under reduced pressure. The resin was then treated with an ice-cold solution of 95% TFA (5% water, 10 mL) and agitated gently for 0.5 h at ice-temperature and then 2.5 h at room temperature. The resin was removed by filtration and washed with several portions of fresh TFA (~10 mL total) and then dry toluene (~15 mL total). The combined filtrate and washings were evaporated under reduced pressure to give a yellow oil which solidified on trituration with dry diethyl ether. The product was purified by preparative RP HPLC using the following gradient (minutes, % B): 0, 5:10, 5; 20, 10:80, 40; 90, 100. (A=0.1% TFA, B=90% acetonitrile/10% water/0.1% TFA, flow rate=10 mL min$^{-1}$, detection 214 nm). One major component was eluted at 63 min which was freeze dried to give a cream, hygroscopic solid (0.009 g, 37%). Analytical HPLC, $R_t$=25 min. MS: m/z 495=[ATS{Me}/P-p-carb-Lys-OH+H$^+$]. Single mass analysis $C_{20}H_{31}N_8O_3S_2$ mass=495.1941, calc. mass=495.1961.

Example 4P

[Cu(ATS{Me}/P-p-carb Lys(Boc)-OH)]

ATS{Me}/P-p-carb-Lys(Boc)-OH (0.002 g, 0.003 mmol) and copper acetate (0.0007 g, 0.003 mmol) were dissolved in a minimum volume of DMF (0.4 mL) and the mixture was stirred overnight. The solvent was removed under reduced pressure to give the product as a red/brown oily solid (0.0019 g, 96%). UV-VIS: λ/nm (ϵ/M-1 cm-1): 261 (11568) 316 (13083), 365 (8605), 470 (4436). Analytical HPLC $R_t$=33 min. MS: m/z 656={[Cu(ATS{Me}/P-p-carb-Lys(Boc)-OH]+H$^+$}.

Example 4Q

[Cu(ATS{Me}/P-p-carb-Orn(Boc)-OH)]

As per the procedure used in Example 4P except with ATS{Me}/P-p-carb-Orn(Boc)-OH (0.002 g, 0.003 mmol) and copper acetate (0.0007 g, 0.003 mmol). Cu(ATS{Me}/P-p-carb-Orn(Boc)-OH) was isolated as a red/brown oily solid (0.0016, 83%). UV-VIS: λ/nm (ϵ/M-1 cm-1): 260 (8734), 314 (8367), 366 (5918), 469 (3215). Analytical HPLC $R_t$=32 min. MS: m/z 642={[Cu(ATS{Me}/P-p-carb)-Orn(Boc)-OH]+H$^+$}.

Example 4R

[Cu(ATS{Me}/P-p-carb-Lys-OH)]

As per the procedure used in Example 4P except with ATS{Me}/P-p-carb-Lys-OH (0.002 g, 0.004 mmol) and copper acetate (0.001 g, 0.005 mmol). Cu(ATS{Me}/P-p-carb-Lys-OH) was isolated as a red/brown oily solid (0.002 g, 90%). UV-VIS: λ/nm (ϵ/M-1 cm-1): 259 (8613), 316 (10125), 363 (7047), 472 (3555). Analytical HPLC $R_t$=20 min. MS: m/z 556={[Cu(ATS{Me}/P-p-carb)-Lys-OH]+H$^+$}.

Example 4S $H_2$ ATS{Me}/P-p-carb-ocreotide

As per the procedure described in Example 18E below, except with $H_2$ATS{Me}/P-p-carb (0.0915 g, 0.25 mmol, 5 equivalents) and HOBt (0.038 g, 0.25 mmol) dissolved in DMF (2 mL). The product was cleaved using an ice-cold solution of phenol (0.75 g) and triisopropylsilane (0.5 mL) in water (0.5 mL) and TFA (10 mL). The crude product was isolated as a cream powder.

Formation of disulfide bridge: The crude product was dissolved in DMSO (2 mL) and water (15 mL) was added. The mixture was stirred vigorously open to air overnight. The product was purified by preparative RP HPLC as above and two major peaks were eluted at 65 and 68.5 min. The first fraction was freezed dried to give the product as a yellow oily residue. Analytical HPLC $R_t$=40 min. MS: m/z 686=[($H_2$ATS{Me}/P-p-carb-ocreotide)+2H$^+$]$^{2+}$.

Example 4T

[Cu(ATS{Me}/P-p-carb-ocreotide)]

As per general procedure used for Example 4S above except with $H_2$ ATS{Me}/P-p-carb-ocreotide (2 drops) and copper acetate (0.002 g, 0.010 mmol). The product was isolated as a brown residue. Analytical HPLC $R_t$=35 min. MS: m/z 1428={[Cu(ATS{Me}/P-p-carb-ocreotide)]+H$^+$}.

Example Section 5

Zinc bis(thiosemicarbazone)s

Example 5A

Zinc bis(thiosemicarbazone)s

General Procedure (5)

Bis(thiosemicarbazone) (1 eq) was dissolved in MeOH, zinc acetate (1 eq) was added. The solution was heated at reflux for 2 hours then allowed to cool slowly. The precipitate was collected by gravity.

Example 5B

Zn[ATS(Me)/P-Carb]

As per general procedure (5) using ATS(Me)/P-carb (0.21 g, 0.6 mmol), MeOH (20 ml) and zinc acetate (0.14 g, 0.6 mmol). [Zn(ATS(Me)/P-carb)] was isolated as a bright yellow crystalline solid. (0.13 g, 52%). NMR: $\delta_H$ (DMSO) 9.64 (1H, s, NHPh), 7.88 (2H, d, J=8.35 Hz, $C_bH$), 7.81 (2H, d, J=8.45 Hz, $C_cH$), 7.15 (2H, s, NH$_2$), 2.31 (3H, s, CH$_3$) and 2.21 (3H, s, CH$_3$). $\delta_C$ (DMSO) 179.9 and 173.2 (C=S), 162.8 (C=O), 151.6 and 145.9 (C=N), 139.8 ($C_d$), 131.3 ($C_c$), 120.1 ($C_a$), 111.6 ($C_b$) and 14.8 and 14.3 ($CH_3$). MS: m/z=415.0002 (MH$^+$), $ZnC_{15}H_{13}N_3OS$ requires MH$^+$, 414.9989.

Example 5C

Zn[ATS(Et)/P-Carb]

As per general procedure (5) using ATS(Et)/P-carb (0.4 g, 1.1 mmol), MeOH (20 ml) and zinc acetate (0.28 g, 1.1 mmol). ATS(Et)/P-carb was isolated as an orange solid (0.49 g, 88%). NMR: $\delta_H$(d$_6$-DMSO) 9.72 (1H, s, NHPh), 8.22 (1H, t, NHMe), 7.9-7.5 (4H, m, Ph), 3.61 (2H, q, $CH_2CH_3$), 2.30 (3H, s, $CH_3$), 2.20 (3H, s, $CH_3$) and 1.11 (3H, t, $CH_2CH_3$) ES$^+$-MS: m/z=444.1416 (MH$^+$), $C_{15}H_{20}N_6O_2S_2$ requires MH$^+$, 444.1156.

Example 5D

Zn[ATS(H)/P-Carb]

As per general procedure (5) using ATS(H)/P-carb (0.29 g, 1.2 mmol), MeOH (20 ml) and zinc acetate (0.28 g, 1.2 mmol). Zn[ATS(H)/P-carb] was isolated as a yellow solid (0.31 g, 70%). NMR: $\delta_H$ (d$_6$-DMSO) 9.65 (1H, s, NHPh), 8.45 (1H, t, NH$_2$), 7.90-7.60 (4H, m, ArH), 2.25 (3H, s, $CH_3$) and 2.23 (3H, s, $CH_3$).

Example 5E

Zn[ATS(Ph)/P-Carb]

As per general procedure (5) using ATS(Ph)/P-carb (0.52 g, 1.2 mmol), MeOH (20 ml) and zinc acetate (0.28 g, 1.2 mmol). Zn[ATS(Ph)/P-carb] was isolated as a red solid (0.41 g, 68%). NMR: $\delta_H$(d$_6$-DMSO) 9.62 (1H, s, NHPh-carb), 9.33 (1H, t, NHPh), 7.90-7.40 (4 H, d, ArH), 2.30 (3H, s, $CH_3$) and 2.13 (3H, s, $CH_3$). ES$^+$-MS: m/z=492.7559 (MH$^+$), $C_{19}H_{20}N_6O_2S_2$ requires MH$^+$, 492.1056.

Example Section 6

ATS(R)/P-Carb-Amino-BTAP

Example 6A

ATS(R)/P-Carb-Amino-BTAP

General Procedure (6)

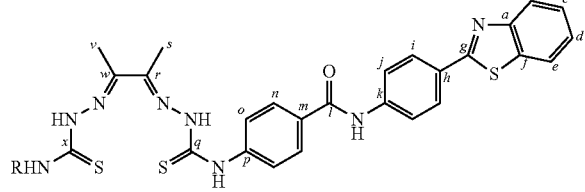

ATS(R)/P-carb (1 eq) and NHS (1 eq) were dissolved in dry DMF and chilled in an ice-bath for 10 minutes. EDC or DIC (1 eq) dissolved in DMF was added and the reaction mixture stirred for 3 h, it warmed slowly to room temperature over 0.5 h. A small portion of the mixture was removed and applied to analytical HPLC and ES$^+$-MS. (R')Amino-BTAP (1 eq) and DIPEA (1.3 eq) where added and the mixture was left to stir for 16 h. The resultant solution was reduced to half its original volume and H$_2$O was added dropwise until no more precipitate formed. The solid was re-dissolved in acetic acid/acetonitrile/water (1/5/4), applied to a preparative HPLC and eluted with the following gradient (minutes, % B): 0, 5; 10, 5; 20, 20; 80, 50; 90, 100. (A=0.1% TFA, B=90% acetonitrile/10% water/0.1% TFA, flow rate=10 mL min$^{-1}$, detection 214 nm).

Example 6B

ATS(H)/P-Carb-Amino-BTAP

As per general procedure (6), using ATS(H)/P-Carb (0.1 g, 0.3 mmol), NHS (0.032 g, 0.3 mmol), EDC (0.0768 g, 0.35 mmol), Amino-BTAP (0.06 g, 0.3 mmol), DIPEA (0.121 mL, 0.6 mmol) and DMF (2.5 mL) (0.002 g, 1.9%). R$_f$-44.5 mins. NMR: $\delta_H$ (d$_6$-DMSO) 10.99 (1H, s, NH Ar ring side), 10.22 (1H, s, NH), 10.11 (1H, s, NHPh-carb), 10.05 (1H, s, NHPh), 8.52 (2H, br s, NH$_2$), 8.20-7.9 (5H, m, $C_oH+C_nH+C_b$), 7.91 (1H, d, J=8.1, $C_eH$), 7.85 (2H, d, J=7.9, $C_i$ H), 7.46 (1H, t, J=7.8, $C_dH$), 7.38 (1H, t, J=7.8, CH), 6.63 (2H, d, J=8.0, $C_jH$), 6.46 (2H, br s, NH$_2$), 2.90 (3H, s, Me) and 2.13 (3H, s, Me). $\delta_C$ (d$_6$-DMSO) 178.9 and 177.6 (C=S), 170.5 and 170.41 (C=N), 168.1 (C=O), 153.9 ($C_f$), 151.7 ($C_g$), 161.3 ($C_k$), 145.2 ($C_p$), 133.7 ($C_a$), 130.4 ($C_n$), 128.7 ($C_i$), 126.2 ($C_d$), 124.3 ($C_c$), 124.1 (CO), 121.9 ($C_b$), 121.7 ($C_e$), 120.0 ($C_m$), 119.8 ($C_h$), 111.7 ($C_j$), 14.2 ($CH_3$) and 14.1 ($CH_3$).

Example 6C

ATS(Et)/P-Carb-Amino-BTAP

As per general procedure (6), using ATS(Et)/P-Carb (0.1 g, 0.3 mmol), NHS (0.030 g, 0.3 mmol), EDC (0.0768 g, 0.35 mmol), Amino-BTAP (0.06 g, 0.3 mmol), DIPEA (0.121 mL, 0.6 mmol) and DMF (2.5 mL) (0.002 g, 1.9%). R$_f$ 46.0 mins. NMR: $\delta_H$(d$_6$-DMSO) 10.88 (1H, s, NH Ar ring side), 10.32 (1H, s, NH), 10.17 (1H, s, NHPh-carb), 10.00 (1H, s, NHPh), 8.42 (2H, br s, NH$_2$), 8.20-7.7 (6H, m, $C_oH+C_nH+C_b+C_eH$), 7.82 (2H, d, J=7.7, $C_i$ H), 7.56 (1H, t, J=8.0, $C_dH$), 7.48 (1H, t, J=7.8, CH), 6.60 (2H, d, J=8.0, $C_jH$), 6.46(2H, br s, NH$_2$), 3.15 (2H, q, $CH_2CH_3$), 2.95 (3H, s, Me), 2.23 (3H, s, Me) and 1.22 (3H, t, $CH_2CH_3$) $\delta_C$ (d$_6$-DMSO) 178.8 and 177.9 (C=S), 170.0 and 169.0 (C=N), 168.2 (C=O), 153.2 ($C_f$), 152.7 ($C_g$), 161.3 ($C_k$), 145.5 ($C_p$), 133.3 ($C_a$), 130.1 ($C_n$), 128.6 ($C_i$), 126.1 ($C_d$), 124.2 ($C_c$), 124.0 ($C_o$), 122.0 ($C_b$), 121.5 ($C_e$), 120.0 ($C_m$), 118.8 ($C_h$), 113.7 ($C_j$), 14.6 ($CH_3$), 14.2 ($CH_3$), 39.17 ($CH_2CH_3$), 25.54 ($CH_2CH_3$), 14.6 ($CH_3$), 14.2 ($CH_3$).

Example 6D

Diamino-BTAP-ATS(Me)/P-Carb

As per general procedure (6), using ATS(Me)/P-Carb (0.14 g, 0.4 mmol), NHS (0.044 g, 0.4 mmol), DIC (0.055 g, 0.43 mmol), Diamino-BTAP (0.19 g, 0.8 mmol), DIPEA (0.27 mL, 1.2 mmol) and DMF (3.0 mL) (0.007 g, 3.3%). $R_f$ 29 mins. $\lambda_{max}$=480 nm. NMR: $\delta_H$ ($d_6$-DMSO) 10.95 (1H, s, NH), 10.28 (1H, s, NH), 10.08 (1H, s, NH), 10.05 (1H, s, NH), 8.42 (2H, br s, $NH_2$), 8.20-7.0 (5H, m, ArH), 6.60 (2H, d, J=8.1, ArH), 6.56 (2H, br s, $NH_2$), 2.85 (3H, s, Me), 2.24 (3H, d, Me) and 2.13 (3H, s, Me). $ES^+$-MS: m/z=590.1807 ($MH^+$), $C_{27}H_{27}N_9OS_3$ requires $MH^+$, 590.1501).

Example Section 7

ATS(ME)/A and its Derivatives and Zinc Complexes

Example 7A

ATS(Me)/A

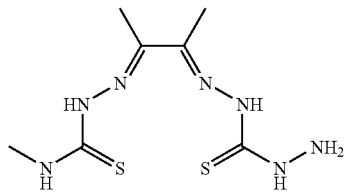

Thiosemicarbazide ((0.23 g, 2.21 mmol)) was dissolved in ethanol (15 ml) and heated to 80° C., 2,3-butadione-N4-methylthiosemicarbazone (0.36 g, 2.21 mmol) was added in portions over 2 hours whilst the solution was stirred at reflux. HCl (0.08 ml, 2.21 mmol) was added and the solution was stirred at reflux under a $N_2$ atmosphere for a further 4 h. The cream solid was collected by gravity filtration and washed with ethanol and di-ethyl ether. (0.33 g, 61%) %). NMR: $\delta_H$ ($d_6$-DMSO) 10.23, (1H, s, NH), 10.21 (1H, s, NH), 9.70 (1H, s, $NHNH_2$), 8.40 (1H, m, J=4.5 Hz, $NHCH_3$), 5.00 (2H, s, $NH_2$), 3.03 (3H, d, J=4.5 Hz, $NHCH_3$), 2.20 (3H, s, $CH_3$) and 2.17 (3H, s, $CH_3$). $ES^+$-MS: m/z=429.0719 ($MH^+$), $C_7H_{15}N_7S_2$ requires $MH^+$, 429.1089.

Example 7B

Zn[ATS(Me)/A]

As per general procedure (5) using ATS(Me)/A (0.48 g, 1.9 mmol), zinc acetate (0.43 g, 1.9 mmol) and MeOH (10 mL). (0.32 g, 79%). NMR: $\delta_H$($d_6$-DMSO) 10.23, (1H, s, NH), 10.02 (1H, br s, NH), 8.23 (1H, br s, NH), 7.20 (2H, br s, $NH_2$), 2.96 (3H, d, J=4.5 Hz, $NHCH_3$), 2.20 (3H, s, $CH_3$) and 1.91 (3H, s, $CH_3$). $ES^+$-MS: m/z=324.0009 ($MH^+$), $ZnC_7H_{15}N_7S_2$ requires $MH^+$, 324.9965.

Example 7C

Zn[ATS(Me)/A-T]

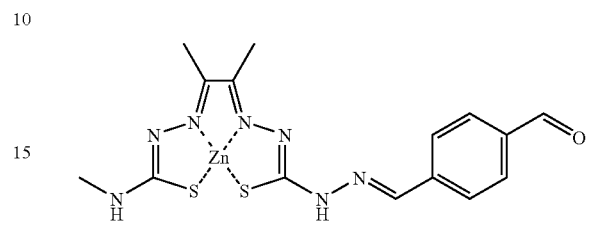

Zn[ATS(Me)/A] (0.82 g, 1.2 mmol), terephthalaldehyde (0.6 g, 6 mmol) and a catalytic amount of acetic acid where dissolved in ethanol (20 mL) and stirred at reflux temperature for 1 h. The solution cooled to room temperature and the solid was collected by filtration, washed with MeOH (10 mL) and diethyl ether (5×15 mL) (0.45 g, 87%). NMR: $\delta_H$ ($d_6$-DMSO) 11.51 (1H, br s, NH), 9.98 (1H, s, C(O)H), 8.15 (1H, s, C(N)H), 7.80 (2H, d, J=8.2, ArH), 7.42 (1H, br s, NH), 2.92 (3H, s, $NHCH_3$), 2.29 (3H, s, $CH_3$) and 2.23 (3H, s, $CH_3$). (Found: C, 40.39; H, 3.80; N, 19.92%. $ZnC_{15}H_{17}N_7OS_2$ requires C, 39.18%; H, 3.86%; N, 21.17%).

Example 7D

Zn[ATS(Me)/A-T-AminoBTAP]

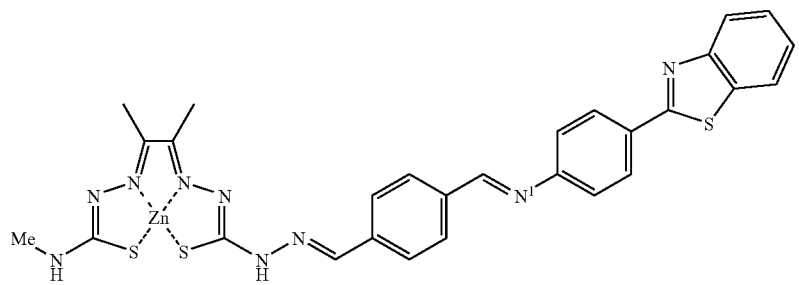

Zn[ATS(Me)/A-T] (0.24 g, 5.45 mmol) and Amino-BTAP (0.12 g, 5.45 mmol) were stirred at reflux for 7 hours. The precipitate was collected by gravity filtration washed in MeOH (2×10 mL) and diethyl ether (3×15 ml). (0.16 g, 47%) $R_f$=47 min. NMR: $\delta_H$($d_6$-DMSO) 11.57 (1H, br s, NH), 8.20 (1H, s, C(N)H), 8.04 (1H, s, C(N)H), 8.01 (1H, d, J=8.0, ArH), 8.0-7.60 (7H, m, ArH), 8.48 (1H, t, J=8.1, ArH), 8.40 (1H, t, ArH), 6.98 (1H, br s, $NHCH_3$), 6.67 (2H, d, J=8.0, ArH), 2.91 (3H, s, $NHCH_3$), 2.25 (3H, s, $CH_3$) and 2.22 (3H, s, $CH_3$).) Plus peaks consistent with the presence of Zn[ATS(Me)/A-T-A/ATS(Me)]Zn. MALDI-MS: m/z=648.69 ($MH^+$), $ZnC_{28}H_{25}N_9S_3$ requires $MH^+$, 648.07.

Example Section 8

GTS(R) and its Zinc Complex

Example 8A

GTS(R)

General Procedure (7)

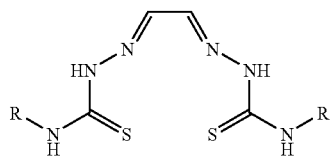

Alkylthiosemicarbazide (2 eq) was dissolved in ethanol, glyoxal (aq) 40% (1.0 eq) was added. The resulting solution was stirred for 3 hours. The solid precipitate was collected by gravity filtration washed with water, ethanol and then diethyl ether.

Example 8B

GTS(Me)

As per general procedure (7) using methylthiosemicarbazide (0.65 g, 6.2 mmol), ethanol (25 ml) and glyoxal (aq) (0.45 ml, 3.1 mmol). GTS(Me) was isolated as a white solid. (0.62 g, 64%). The full characterisation of the product by $^1$H and $^{13}$C NMR, ES$^+$-MS and elemental analysis was consistent with reported values. The full characterisation of the product by $^1$H and $^{13}$C NMR, and ES$^+$-MS was consistent with reported values. NMR: $\delta_H$ (DMSO) 11.75 (2H, s, NH), 8.48 (2H, d, J=4.54, 8.48), 7.70 (2H, s, CH) and 2.93 (6H, d, J=4.51, NHCH$_3$).

Example 8C

GTS(Et)

As per general procedure (7) using ethylthiosemicarbazide (0.5 g, 4.2 mmol), ethanol (15 ml) and glyoxal (aq) (0.25 ml, 2.1 mmol). GTSE was isolated as a cream solid (0.45 g, 82%) The full characterisation of the product by $^1$H and $^{13}$C NMR, and ES$^+$-MS was consistent with reported values. NMR: $\delta_H$ (DMSO) 11.68 (2H, s, NH), 8.511 (2H, t, NHCH$_2$CH$_3$), 7.69 (2H, s, CH), 3.50 (4H, q, J=6.64, CH$_2$CH$_3$) and 1.06 (6H, t, J=6.10, CH$_2$CH$_3$).

Example 8D

GTS(Ph)

As per general procedure (7) using phenylthiosemicarbazide (0.6 g, 3.6 mmol), ethanol (15 ml) and glyoxal (aq) (0.21 ml, 1.8 mmol). GTS(Ph) was isolated as a white solid (0.47 g, 73%) The full characterisation of the product by $^1$H and $^{13}$C NMR, and ES$^+$-MS was consistent with reported values. NMR: $\delta_H$ (DMSO) 12.14 (2H, s, NH), 10.18 (2H, s PhNH), 7.866 (2H, s, CH), 7.53 (4H, d, J=7.57, Ar—H), 7.33 (4H, t, J=7.57, Ar—H) and 7.17 (2H, t, J=7.34, Ar—H).

Example 8E

Zn[GTS(Me)]

As per general procedure (5) using GTS(Me) (0.40 g, 1.7 mmol), MeOH (20 ml) and zinc acetate (0.38 g, 1.7 mmol). Zn[GTS(Me)] was isolated as an orange solid. (0.20 g, 79%). The full characterisation of the product by $^1$H and $^{13}$C NMR, ES$^+$-MS and elemental analysis was consistent with reported values. NMR: $\delta_H$ (DMSO) 8.44 (2H, bs, NHMe), 7.54 (2H, s, CH=N) and 3.12 (6H, bs, CH$_3$).

Example 8F

Zn[GTS(Et)]

As per general procedure (5) using GTS(Et) (0.20 g, 0.8 mmol), MeOH (20 ml) and zinc acetate (0.17 g, 0.8 mmol). [Zn(GTS(Et)] was isolated as an orange solid. (0.20 g, 79%). The full characterisation of the product by $^1$H and $^{13}$C NMR, ES$^+$-MS and elemental analysis was consistent with reported values. NMR: $\delta_H$ (DMSO) 8.26 (2H, bs, NHEt), 7.56 (2H, s, CH=N), 3.51 (4H, bs, CH$_2$CH$_3$) and 1.12 (6H, bs, CH$_2$CH$_3$.

Example 8G

Zn[GTS(Ph)]

As per general procedure (5) using GTS(Ph) (0.16 g, 0.5 mmol), MeOH (20 ml) and zinc acetate (0.09 g, 0.5 mmol). Zn[GTS(Ph)] was isolated as a red solid. (0.22 g, 90%). The full characterisation of the product by $^1$H and $^{13}$C NMR, ES$^+$-MS and elemental analysis was consistent with reported values. NMR: $\delta_H$ (DMSO) 9.66 (2H, s, NHPh), 7.76 (2H, s, CH=N), 7.71 (4H, bd, ArH), 7.22 (4H, bt, ArH), and 6.93 (2H, t, ArH).

All of the zinc complexes studied (see above examples) showed a metal based fluorescence between 530 and 570 nm. Those with phenyl substituents show an additional less intense fluorescence band between 340 and 390 nm and their 530-570 nm fluorescence tends to have larger values of $\lambda_{max}$ than their alkyl substituted analogues. The conjugate Zn [ATS(Me)/A-T-Amino-BTAP] was observed to have two strong fluorescence bands, one at 420 nm associated with the BTAP and one at 560 nm associated with the metal complex.

Example Section 9

Mono-keto-(thiosemicarbazones)

Example 9A

Mono-keto-(4-methylthiosemicarbazones)

General Procedure (8)

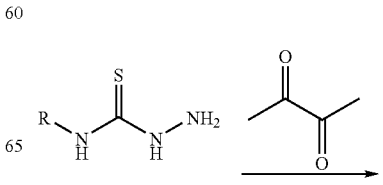

-continued

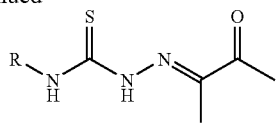

Butane-2,3-dione (1.07 mL, 12.00 mmol) and conc. HCl (0.5 mL) were added to 4-methylthiosemicarbazide (1.05 g, 10.00 mmol) in water (20 mL). The mixture was cooled in an ice bath and stirred for 30 min. A bulky white solid settled out of solution and was filtered, washed with cold water and left to dry in air for 24 h. The product was isolated as a white solid (1.05 g, 61%). $R_f$: 20 $^1$H NMR: δ 1.95 (3H, s, $CH_3$); 2.42 (3H, s, $CH_3$); 3.05 (3H, d, J 4.56, $NHCH_3$); 8.63 (1H, d, J 3.94, $NHCH_3$); 10.65 (1H, s, NH). $^{13}$C NMR: δ 10.00; 24.75; 31.39; 145.42; 178.88; 197.43. MS ES$^+$: m/z 173.97 (100%, $[C_6H_{11}N_3OS]H^+$).

Example 9B

Mono-keto-(4-phenylthiosemicarbazone)

As per general procedure (8) except with butane-2,3-dione (1.22 mL, 13.92 mmol), conc. HCl (0.5 mL) and 4-phenylthiosemicarbazide (1.57 g, 9.40 mmol). The product was isolated as a pale orange solid (1.79 g, 81%). $^1$H NMR: δ 2.03 (3H, s, $CH_3$); 2.48 (3H, s, $CH_3$); 7.25 (1H, t, J 7.37, 4-ArH); 7.40 (2H, t, J 7.76, 3-ArH); 7.55 (2H, d, J 7.49, 2-ArH); 10.20 (1H, s, NHPh); 10.98 (1H, s, NH). $^{13}$C NMR: δ 198.0; 178.2; 149.6; 146.7; 139.4; 129.1; 126.2; 25.5; 10.8. MS ES+: m/z 236.10 (80%, $[C_{11}H_{13}N_3OS]H^+$) and m/z 258.07 (100%, $[C_{11}H_{13}N_3OS]Na^+$).

Example Section 10

Thiosemicarbazides from Amines

Example 10A

4-Phenylthiosemicarbazide

General Procedure (9)

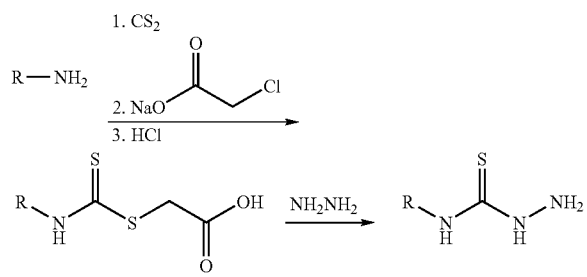

Aniline (1.82 mL, 20.00 mmol) was added to NaOH (0.80 g, 20.00 mmol) in water (40 mL). $CS_2$ (1.20 mL, 20.00 mmol) was added and the reaction mixture was stirred for 4 h, after which time the organic layer had disappeared. The orange solution was treated with sodium chloroacetate (2.33 g, 20.00 mmol) and left to stir for 16 h. The cloudy yellow solution was acidified with conc. HCl and filtered. The solid recovered was dissolved in water (20 mL) and an excess of $NH_2NH_2$ (5.60 mL, 0.18 mol) was added. The mixture was heated at 90° C. for 30 min. The solid formed was collected by filtration, washed with water and dried in vacuo. The product was isolated as a white crystalline solid (2.54 g, 76%). $^1$H NMR: δ 4.80 (2H, s, $NH_2$); 7.09 (1H, t, J 7.33, 4-ArH); 7.32 (2H, t, J 7.86, 3-ArH); 7.65 (2H, d, J 7.05, 2-ArH); 9.15 (1H, s, NHPh); 9.71 (1H, s, $NHNH_2$).

Example 100B 4-(p-Aminophenyl)thiosemicarbazide

As per general procedure (9) except with benzene-1,4-diamine (2.16 g, 20.00 mmol), $CS_2$ (1.20 mL, 20.00 mmol), NaOH (0.80 g, 20.00 mmol), sodium chloroacetate (2.33 g, 20.00 mmol) and $NH_2NH_2$ (5.60 mL, 0.18 mol). The product was isolated as a cream solid (1.37 g, 38%). $^1$H NMR: δ 4.65 (2H, s, $PhNH_2$); 4.95 (2H, s, $NHNH_2$); 6.49 (2H, d, J 8.65, 3-ArH); 7.08 (2H, d, J 8.30, 2-ArH); 8.80 (1H, s, NH); 9.25 (1H, s, $NHNH_2$).

Example 10C

Ethane-1,2-dithiosemicarbazide

As per general procedure (9) except with ethane-1,2-diamine (1.67 mL, 25.00 mmol), $CS_2$ (4.50 mL, 75.00 mmol), NaOH (2.00 g, 50.00 mmol), sodium chloroacetate (5.83 g, 50.00 mmol) and $NH_2NH_2$ (10.88 mL, 0.35 mol), the conc. HCl used to acidify the cloudy yellow solution was before it was filtered was 2M HCl, and the mixture was heated at 90° C. for 2 hrs. The solid formed as a precipitate and was washed well with water before drying. The product was isolated as a white powder (3.32 g, 64%). $R_f$: 43. $^1$H NMR: δ 3.60 (4H, s, $CH_2$); 4.45 (4H, s, $NH_2$); 8.02 (2H, s, $CH_2NH$); 8.69 (2H, s, $NHNH_2$). $^{13}$C NMR: δ 42.53; 180.87. MS ES+: m/z 209.10 (5%, $[C_4H_{12}N_6S_2]H^+$) and m/z 231.05 (50%, $[C_4H_{12}N_6S_2]Na^+$).

Example 10D

Propane-1,3-dithiosemicarbazide

As per general procedure (9) except with propane-1,3-diamine (1.85 mL, 25.00 mmol), $CS_2$ (4.50 mL, 75.00 mmol), NaOH (2.00 g, 50.00 mmol), sodium chloroacetate (5.83 g, 50.00 mmol) and $NH_2NH_2$ (10.88 mL, 0.35 mol). The product was isolated as a cream solid (2.46 g, 44%). $^1$H NMR: δ 1.66 (2H, m, J 5.83, $CH_2CH_2CH_2$); 3.46 (4H, m, J 5.85, $CH_2CH_2CH_2$); 4.43, (4H, s, $NH_2$); 8.09 (2H, s, $CH_2NH$) 8.58 (2H, s, $NHNH_2$).

Example 10E

Cyclohexane-trans-1,4-dithiosemicarbazide

As per general procedure (9) except with trans-1,4-diaminocyclohexane (1.14 g, 10.00 mmol) and $CS_2$ (1.20 mL, 20.00 mmol) in an ethanol solution of KOH (1.12 g, 20.00 mmol in 40 mL EtOH), sodium chloroacetate (2.33 g, 20 mmol) and $NH_2NH_2$ (5.60 mL, 0.18 mol). The product was isolated as a pale brown powder (1.04 g, 40%). $^1$H NMR: δ

1.36 (4H, m, J 8.95, CH$_{2ax}$); 1.86 (4H, m, J 5.68, CH$_{2eq}$); 4.04 (2H, s, CH$_{ax}$); 4.44 (4H, s, NH$_2$); 7.55 (2H, d, J 8.33, NH); 8.59 (2H, s, NHNH$_2$).

Example Section 11

Dissymmetric bis(thiosemicarbazones) and Ni, Cu and Zn Complexes Thereof

Example 11A

ATSM/PH$_2$

General Procedure (10)

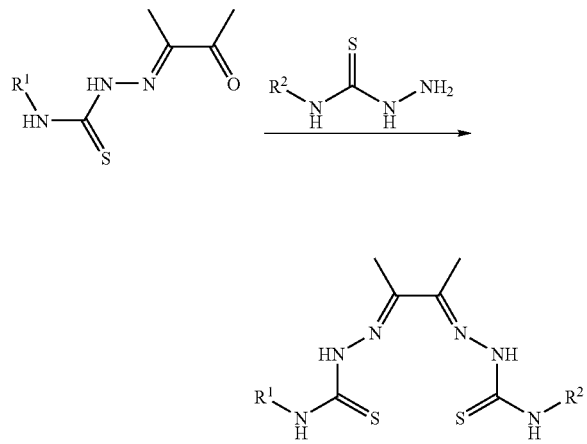

Mono-keto-(4-methylthiosemicarbazone) (0.97 g, 5.61 mmol) and acetic acid (0.5 mL) were added to a solution of 4-phenylthiosemicarbazide (0.94 g, 5.61 mmol) in methanol (30 mL). The mixture was heated under reflux for 3 h under an atmosphere of nitrogen and allowed to cool slowly to room temperature. The resulting white solid was washed with methanol and diethyl ether and dried in vacuo. The product was isolated as a white powder (1.35 g, 750%). $^1$H NMR: δ 2.25 (3H, s, CH$_3$); 2.29 (3H, s, CH$_3$); 3.03 (3H, d, J 4.49, NHCH$_3$); 7.21 (1H, t, J 7.33, 4-ArH); 7.37 (2H, t, J 7.78, 3-ArH); 7.56 (2H, d, J 7.71, 2-ArH); 8.43 (1H, d, J 4.51, NHCH$_3$); 9.96 (1H, s, NHPh); 10.33 (1H, s, NH); 10.60 (1H, s, NH).

Example 11B

ATSM/P(p-NH$_2$)H$_2$

As per general procedure (10) except with mono-keto-(4-methylthiosemicarbazone) (0.91 g, 5.27 mmol), acetic acid (0.25 mL) and 4-p-aminophenylthiosemicarbazide (0.96 g, 5.27 mmol). The product was isolated as a yellow solid (0.99 g, 56%). $^1$H NMR: δ 2.22 (3H, s, CH$_3$); 2.26 (3H, s, CH$_3$); 3.02 (3H, s, NHCH$_3$); 5.07 (2H, s, NH$_2$); 6.53 (2H, d, J 8.06, 3-ArH); 7.07 (2H, d, J 8.23, 2-ArH); 8.40 (1H, s, NHCH$_3$); 9.68 (1H, s, NHPh); 10.24 (1H, s, NH); 10.33 (1H, s, NH).

Example 11C

Zn[ATSM/P]

General Procedure (11)

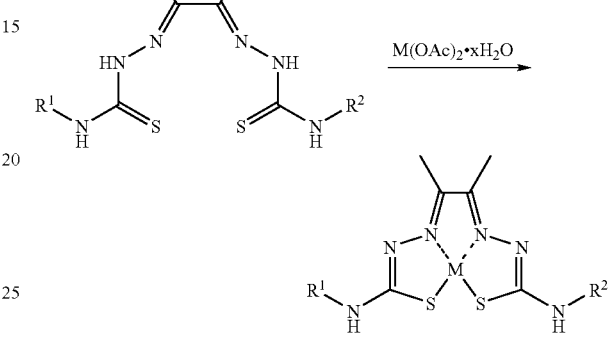

ATSM/PH$_2$ (0.25 g, 0.79 mmol) and Zn(OAc)$_2$.2H$_2$O (0.17 g, 0.79 mmol) were added to methanol (30 mL). The mixture was heated under reflux for 3 h under an atmosphere of nitrogen and allowed to cool slowly to room temperature. A yellow precipitate formed which was washed with methanol and diethyl ether and dried in vacuo. The product was isolated as a yellow powder (0.26 g, 87%). (Mass: 385.0236. Calc. mass for C$_{13}$H$_{17}$N$_6$S$_2$Zn: 385.0248.) R$_f$: 39. $^1$H NMR: δ 2.24 (3H, s, CH$_3$); 2.30 (3H, s, CH$_3$); 2.85 (3H, m, NHCH$_3$); 6.90 (1H, m, J 7.31, 4-ArH); 7.24 (2H, m, J 7.38, 3-ArH); 7.41 (1H, m, NHCH$_3$); 7.81 (2H, m, J 7.83, 2-ArH); 9.35 (1H, s, NHPh). $^{13}$C NMR: δ 13.48; 14.34; 119.35; 120.88; 127.93; 140.77; 148.58; 172.12. MS ES+: m/z 385.02 (100%, Zn[ATSM/P]H$^+$).

Example 11D

Cu[ATSM/P]

As per general procedure (11) except with ATSM/PH$_2$ (0.35 g, 1.09 mmol) and Cu(OAc)$_2$.H$_2$O (0.22 g, 1.10 mmol). The product was isolated as a brown powder (0.31 g, 75%). (Mass: 384.0261. Calc. mass for C$_{13}$H$_{17}$CuN$_6$S$_2$: 384.0252.) R$_f$: 45. MS ES+: m/z 384 (100%, Cu[ATSM/P]H$^+$).

Example 11E

Ni[ATSM/P]

As per general procedure (11) except with ATSM/PH$_2$ (0.36 g, 1.12 mmol) and Ni(OAc)$_2$.4H$_2$O (0.28 g, 1.12 mmol). The product was isolated as a brown powder (0.30 g, 71%). (Mass: 379.0305. Calc. mass for C$_{13}$H$_{17}$N$_6$NiS$_2$: 379.0310.) R$_f$: 49. $^1$H NMR: δ 1.99 (3H, s, CH$_3$); 2.05 (3H, s, CH$_3$); 2.82 (3H, s, NHCH$_3$); 6.98 (1H, s, 4-ArH); 7.28 (2H, s, 3-ArH); 7.60 (2H, s, 2-ArH); 7.89 (1H, s, NHCH$_3$); 9.90 (1H, s, NHPh). MS ES+: m/z 379.03 (100%, Ni[ATSM/P]H$^+$).

Example 11F

Zn[ATSM/P(p-NH$_2$)]

As per general procedure (11) except with ATSM/(p-NH$_2$) H$_2$ (0.41 g, 1.22 mmol) and Zn(OAc)$_2$.2H$_2$O (0.27 g, 1.22 mmol). The product was isolated as a yellow solid (0.33 g, 68%). $^1$H NMR: δ 2.22 (3H, s, CH$_3$); 2.24 (3H, s, CH$_3$); 2.83 (3H, m, NHCH$_3$); 4.76 (2H, s, NH$_2$); 6.46 (2H, d, J 8.61, 3-ArH); 7.29 (1H, m, NHCH$_3$); 7.42 (2H, d, J 8.50, 2-ArH); 8.99 (1H, s, NHPh). MS ES+: m/z 400.04 (100%, Zn[ATSM/P(p-NH$_2$)]H$^+$).

Example Section 12

Dithiosemicarbazides and Derivatives and Complexes Thereof

Example 12A

Benzene-1,4-dithiosemicarbazide

General Procedure (12)

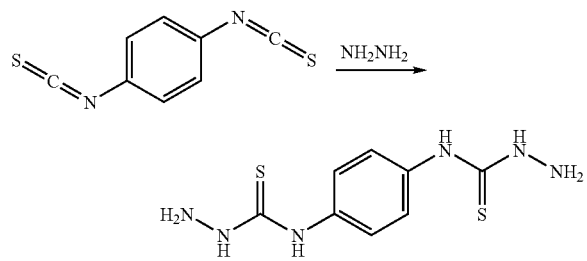

An aqueous solution of hydrazine (0.72 mL, 25.00 mmol in 0.5 mL water) was added to a solution of benzene-1,4-diisothiocyanate (0.24 g, 1.25 mmol) in ethanol (20 mL). The mixture was stirred for 30 min and then cooled in an ice bath. The resulting grey precipitate was collected by filtration, washed well with ethanol and water and dried in vacuo. The product was isolated as a pale grey powder (0.33 g, 75%). (Mass: 279.0468. Calc. for C$_8$H$_{12}$N$_6$NaS$_2$: 279.0463.) $^1$H NMR: δ 4.78 (4H, s, NH$_2$); 7.52 (4H, s, ArH); 9.10 (2H, s, PhNH); 9.66 (2H, s, NHNH$_2$). $^{13}$C NMR: δ 122.98; 135.01; 178.93. MS ES+: m/z 279.05 (100%, [C$_8$H$_{12}$N$_6$S$_2$]Na$^+$).

Example 12B

1-Methylbenzene-2,4-dithiosemicarbazide

As per general procedure (12) except with 1-methylbenzene-2,4-diisothiocyanate (0.52 g, 2.52 mmol) and hydrazine (1.57 mL, 50 mmol). The product was isolated as a white powder (1.38 g, 93%). R$_f$: 47. $^1$H NMR: δ 2.15 (3H, s, PhCH$_3$); 4.79 (4H, s, NH$_2$); 7.11 (1H, d, J 8.28, 5-ArH); 7.43 (1H, m, J 6.54, 5-ArH); 7.81 (1H, m, 3-ArH); 9.09 (2H, s, PhNH); 9.57 (1H, s, NH). $^{13}$C NMR: 6180.5; 179.6; 137.9; 137.2; 129.6; 129.5; 122.4; 121.2; 17.7.

Example 12C

ATSMH$_2$/1,4-Ph/ATSMH$_2$

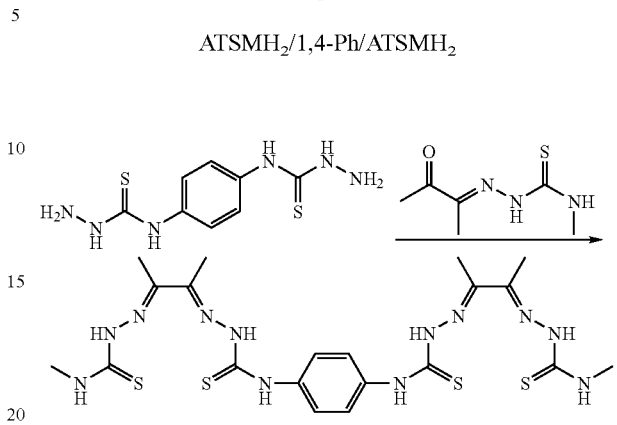

Mono-keto-(4-methylthiosemicarbazone) (0.66 g, 3.83 mmol) and acetic acid (0.5 mL) were added to a solution of benzene-1,4-dithiosemicarbazide (0.49 g, 1.91 mmol) in DMF (30 mL). The mixture was heated at 60° C. for 3 h under an atmosphere of nitrogen and allowed to cool slowly to room temperature. Water (20 mL) was added slowly and a cream precipitate formed. The solid was collected by filtration, washed with methanol and diethyl ether and dried in vacuo. The product was isolated as a cream solid (0.76 g, 70%). $^1$H NMR: δ 2.25 (6H, s, CH$_3$); 2.28 (6H, s, CH$_3$); 3.02 (6H, d, J 4.48, NHCH$_3$); 7.53 (4H, s, ArH); 8.45 (2H, q, J 4.60, NHCH$_3$); 9.99 (2H, s, NH); 10.30 (2H, s, NH); 10.59 (2H, s, NH).

Example 12D

Zn$_2$[ATSM/1,4-Ph/ATSM]

General Procedures (13) and (13a)

General procedure (13): A solution of Zn(OAc)$_2$.2H$_2$O (0.96 g, 4.38 mmol) was added to a solution of benzene-1,4-dithiosemicarbazide (0.56 g, 2.19 mmol) in ethanol (30 mL) and stirred for 5 min. Mono-keto-(4-methylthiosemicarbazone) (0.76 g, 4.38 mmol) was added and the mixture was heated under reflux for 16 h and allowed to cool slowly to room temperature. The yellow solid that formed was collected by filtration, washed with ethanol and diethyl ether and dried in vacuo. The product was isolated as a yellow powder (0.70 g, 46%). $^1$H NMR: δ 2.24 (6H, s, CH$_3$); 2.29 (6H, s, CH$_3$); 2.85 (6H, s, CH$_3$NH); 7.45 (2H, s, CH$_3$NH); 7.66 (4H, s, CH); 9.28 (2H, s, PhNH). MS ES+: 692.99 (10%, Zn$_2$-[ATSM/1,4-Ph/ATSM]H).

General procedure (13a): Zinc acetate (0.29 g, 1.32 mmol) and benzene-1,4-dithiosemicarbazide (0.15 g, 0.59 mmol) were added to a solution of mono-keto-(4-methylthiosemicarbazone) (0.20 g, 1.18 mmol) in methanol. The mixture was heated under reflux for 16 h and allowed to cool slowly to room temperature. The orange solid that formed was collected by filtration, washed with methanol and diethyl ether and dried in vacuo. The product was isolated as an orange powder (0.16 g, 39%). (Found: C, 36.45; H, 4.0; N, 21.5. Calc. for C$_{20}$H$_{26}$N$_{12}$S$_4$Zn$_2$: C, 34.6; H, 3.8; N, 24.2.). $^1$H NMR: δ 2.24 (6H, s, CH$_3$); 2.29 (6H, s, CH$_3$); 2.85 (6H, s, CH$_3$NH); 7.37 (2H, s, CH$_3$NH); 7.66 (4H, s, ArH); 9.27 (2H, s, PhNH). MS ES+: 692.07 (100%, [Zn$_2$

[ATSM/1,4-Ph/ATSM]]H$^+$), 348.00 (40, [Zn$_2$[ATSM/1,4-Ph/ATSM]]H$_2^{2+}$).

Example 12E (i) AND (ii)

Zn$_2$-[ATSM/2,4-Tol/ATSM]

(i) As per general procedure (13) except with Zn(OAc)$_2$.2H$_2$O (0.88 g, 4.00 mmol), 1-methylbenzene-2,4-dithiosemicarbazide (0.54 g, 2.00 mmol) and mono-keto-(4-methylthiosemicarbazone) (0.69 g, 4.00 mmol). The product was isolated as a yellow/orange powder (1.67 g, 74%). (Found: Zn, 17.1%. Calc. for C$_{21}$H$_{28}$N$_{12}$S$_4$Zn$_2$: Zn, 18.5%.) $^1$H NMR: δ 2.10 (3H, s, CH$_3$); 2.12 (3H, s, CH$_3$); 2.18 (3H, s, CH$_3$); 2.22 (3H, s, CH$_3$); 2.24 (3H, s, PhCH$_3$); 2.84 (H, s, NHCH$_3$); 7.02 (1H, d, J 8.52, 6-ArH); 7.31 (1H, s, CH$_3$NH); 7.37 (1H, s, CH$_3$NH); 7.49 (1H, m, J 8.35, 5-ArH); 7.93 (1H, d, J 1.84, 3-ArH); 8.60 (1H, s, PhNH); 9.29 (1H, s, PhNH). MS ES+: 643 (100%, [ZnLH$_2$]H$^+$); 709 (5%, [Zn$_2$L]H$^+$).

(ii) As per general procedure (13a) except with zinc acetate (0.37 g, 1.69 mmol), 1-methylbenzene-2,4-dithiosemicarbazide (0.23 g, 0.85 mmol) and mono-keto-(4-methylthiosemicarbazone) (0.30 g, 1.73 mmol). The product was isolated as a yellow powder (0.26 g, 48%). (Found: C, 35.3; H, 4.4; N, 23.6. Calc. for C$_{21}$H$_{28}$N$_{12}$S$_4$Zn$_2$: C, 35.65; H, 4.0; N, 23.75.) $^1$H NMR: δ 2.10 (3H, s, CH$_3$); 2.12 (3H, s, CH$_3$); 2.18 (3H, s, CH$_3$); 2.22 (3H, s, CH$_3$); 2.24 (3H, s, PhCH$_3$); 2.84 (H, s, NHCH$_3$); 7.02 (1H, d, J 8.48, ArH); 7.31 (1H, s, CH$_3$NH); 7.37 (1H, s, CH$_3$NH); 7.49 (1H, m, J 8.35, 2.05, ArH); 7.93 (1H, d, J 1.84, ArH); 8.60 (1H, s, PhNH); 9.29 (1H, s, PhNH). $^{13}$C NMR: δ 13.80; 14.16; 14.65; 17.60; 29.18; 116.58; 118.22; 125.68; 129.34; 138.44; 138.89; 146.84; 148.50; 172.35; 174.84. MS ES+: 709.01 (100%, [Zn$_2$[ATSM/2,4-Tol/ATSM]]H$^+$);1415.07(10,[Zn$_2$[ATSM/2,4-Tol/ATSM]]$_2$H$^+$).

Example 12F (i) AND (ii)

Mono-keto-(ethane-1,2-dithiosemicarbazone)

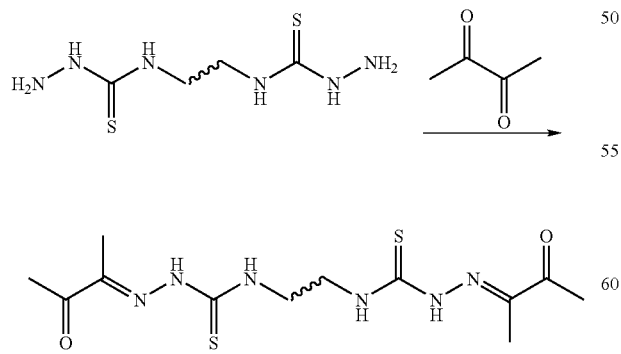

(i) As per general procedure for mono-keto-(4-methylthiosemicarbazone) in general procedure (8) above except with butane-2,3-dione (1.75 mL, 20.00 mmol), conc. HCl (5 drops) and ethane-1,2-dithiosemicarbazide (2.00 g, 9.62 mmol). The product was isolated as a cream powder (2.44 g, 74%). R$_f$: 29. $^1$H NMR: δ 1.94 (6H, s, CH$_3$); 2.39 (6H, s, CH$_3$); 3.89 (4H, m, CH$_2$); 8.73 (2H, s, CH$_2$NH); 10.76 (2H, s, HH). MS ES+: m/z 345.13 (50%, [C$_{12}$H$_{20}$N$_6$O$_2$S$_2$]H$^+$).

(ii) As per general procedure for mono-keto-(4-methylthiosemicarbazone) in general procedure (8) above except with butanedione (0.46 mL, 5.29 mmol), conc. HCl (0.5 mL) and ethane-1,2-dithiosemicarbazide (0.50 g, 2.40 mmol). The product was isolated as a cream powder (1.34 g, 56%). (Mass: 367.0973. Calc. for C$_{12}$H$_{20}$N$_6$NaO$_2$S$_2$: 367.0987.) $^1$H NMR: δ 1.94 (6H, s, CH$_3$); 2.39 (6H, s, CH$_3$); 3.89 (4H, m, CH$_2$); 8.73 (2H, s, CH$_2$NH); 10.76 (2H, s, NH). $^{13}$C NMR: δ 197.9; 179.3; n146.5; 44.0; 25.4; 10.7. MS ES+: m/z 367.10 (100%, [C$_{12}$H$_{20}$N$_6$O$_2$S$_2$]Na$^+$).

Example 12G

Mono-keto-(propane-1,3-dithiosemicarbazone)

As per general procedure (8) except with butane-2,3-dione (1.75 mL, 20.00 mmol), conc. HCl (5 drops) and propane-1,2-dithiosemicarbazide (2.00 g, 9.01 mmol). The product was isolated as a cream powder (2.01 g, 62%). $^1$H NMR: δ 1.90 (2H, m, J 6.03, CH$_2$CH$_2$CH$_2$); 1.97 (6H, s, CH$_3$); 2.43 (6H, s, CH$_3$); 3.68 (4H, m, J 6.22, CH$_2$CH$_2$CH$_2$); 8.83 (2H, t, J 6.00, CH$_2$NH); 10.70 (2H, s, NH).

Example 12H (i) AND (ii)

Mono-keto-(1-methylbenzene-2,4-dithiosemicarbazone)

(i) As per general procedure (8) except with butane-2,3-dione (1.00 mL, 11.43 mmol), conc. HCl (5 drops) and 1-methylbenzene-2,4-dithiosemicarbazide (1.47 g, 5.44 mmol). The product was isolated as a cream solid (1.50 g, 68%). R$_f$: 39. $^1$H NMR: δ 2.05 (6H, s, CH$_3$); 2.25 (3H, s, PhCH$_3$); 2.51 (6H, s, CH$_3$); 7.32 (1H, d, J 8.32, 6-ArH); 7.47 (1H, m, J 8.17, 2.05, 5-ArH); 7.67 (1H, d, J 1.87, 3-ArH); 10.15 (1H, s, PhNH); 10.24 (1H, s, PhNH); 10.99 (1H, s, NH); 11.00 (1H, s, NH). MS ES+: m/z 407.14 [C$_{17}$H$_{22}$N$_6$O$_2$S$_2$]H$^+$.

(i) As per general formula (8) except with butan-2,3-dione (0.23 mL, 1.19 mmol), conc. HCl (0.5 mL) and 1-methylbenzene-2,4-dithiosemicarbazide (0.32 g, 2.62 mmol). The product was isolated as a cream solid (0.44 g, 92%). (Mass: 407.1319. Calc. for C$_{17}$H$_{23}$N$_6$O$_2$S$_2$: 407.1324.) $^1$H NMR: δ 2.05 (6H, s, CH$_3$); 2.25 (3H, s, PhCH$_3$); 2.51 (6H, s, CH$_3$); 7.32 (1H, d, J 8.32, ArH); 7.47 (1H, m, J 8.17, 2.05, ArH); 7.67 (1H, d, J 1.87, ArH); 10.15 (1H, s, PhNH); 10.24 (1H, s, PhNH); 10.99 (1H, s, NH); 11.00 (1H, s, NH). $^{13}$C NMR: δ 198.13; 198.10; 178.6; 178.0; 149.8; 146.8; 137.9; 137.1; 133.1; 130.1; 125.5; 124.6; 25.5; 25.4; 17.8; 10.8. MS ES+: m/z 429.11 (100%, [C$_{17}$H$_{22}$N$_6$O$_2$S$_2$]Na$^+$).

Example 12I (i) AND (ii)

ATSPH$_2$/CH$_2$CH$_2$/ATSPH$_2$

General Procedure (14)

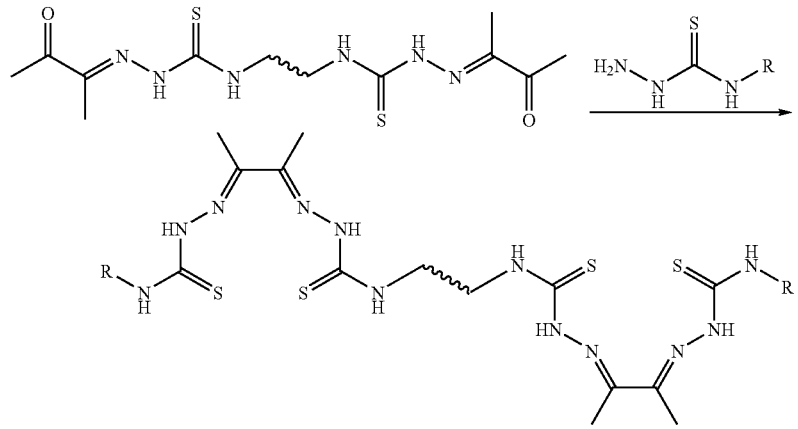

(i) 4-Phenylthiosemicarbazide (1.98 g, 11.84 mmol) and acetic acid (0.5 mL) were added to a solution of mono-keto-(ethane-1,2-dithiosemicarbazone) (2.04 g, 5.92 mmol) in methanol (30 mL). The mixture was heated under reflux for 16 h under an atmosphere of nitrogen and allowed to cool slowly to room temperature. The resulting white solid was washed with methanol and diethyl ether and dried in vacuo. The product was isolated as a pale yellow solid (2.39 g, 63%). R$_f$: 46; 52. $^1$H NMR: δ 2.26 (6H, s, CH$_3$); 2.29 (6H, s, CH$_3$); 3.88 (4H, m, CH$_2$); 7.21 (2H, d, J 7.34, 4-ArH); 7.37 (4H, t, J 7.78, 3-ArH); 7.55 (4H, t, J 7.65, 2-ArH); 8.59 (2H, m, NHCH$_2$); 9.98 (2H, s, NHPh); 10.44 (2H, s, NH); 10.63 (2H, s, NH).

(ii) 4-Phenylthiosemicarbazide (0.15 g, 0.92 mmol) and acetic acid (0.5 mL) were added to a solution of mono-keto-(ethane-1,2-dithiosemicarbazone) (0.15 g, 0.44 mmol) in methanol (30 mL). The mixture was heated under reflux for 16 h under an atmosphere of nitrogen and allowed to cool slowly to room temperature. The resulting white solid was washed with methanol and diethyl ether and dried in vacuo. The product was isolated as a pale yellow solid (0.22 g, 79%). $^1$H NMR: δ 2.26 (6H, s, CH$_3$); 2.29 (6H, s, CH$_3$); 3.88 (4H, m, CH$_2$); 7.21 (2H, d, J 7.34, ArH); 7.37 (4H, t, J 7.78, ArH); 7.55 (4H, t, J 7.65, ArH); 8.59 (2H, m, NHCH$_2$); 9.98 (2H, s, NHPh); 10.44 (2H, s, NH); 10.63 (2H, s, NH). ES MS+: m/z 665.19 (10%, [C$_{26}$H$_{34}$N$_{12}$S$_4$]Na$^+$).

Example 12J (i) AND (ii)

ATSMH$_2$/CH$_2$CH$_2$/ATSMH$_2$ (i) As per general procedure (14) except with 4-methylthiosemicarbazide (1.29 g, 12.31 mmol), acetic acid (0.5 mL) and mono-keto-(ethane-1,2-dithiosemicarbazone) (2.12 g, 6.15 mmol). The product was isolated as a cream solid (1.83 g, 57%). $^1$H NMR: δ 2.20 (6H, s, CH$_3$); 2.21 (6H, s, CH$_3$); 3.01 (6H, d, J 4.49, NHCH$_3$); 3.85 (4H, m, CH$_2$); 8.39 (2H, q, J 4.57, NHCH$_3$); 8.54 (2H, s, NHCH$_2$); 10.26 (2H, s, NH); 10.35 (2H, s, NH).

(i) (As per general procedure 13a) except with 4-methylthiosemicarbazide (0.09 g, 0.86 mmol), acetic acid (0.5 mL) and mono-keto-(ethane-1,2-dithiosemicarbazone) (0.16 g, 0.41 mmol). The product was isolated as a cream solid (0.19 g, 82%). $^1$H NMR: δ 2.20 (6H, s, CH$_3$); 2.21 (6H, s, CH$_3$); 3.01 (6H, d, J 4.49, NHCH$_3$); 3.85 (4H, m, CH$_2$); 8.39 (2H, q, J 4.57, NHCH$_3$); 8.54 (2H, s, NHCH$_2$); 10.26 (2H, s, NH); 10.35 (2H, s, NH). $^{13}$C NMR: δ 178.8; 178.6; 149.1; 148.3; 44.0; 31.6; 12.3; 12.2.

Example 12K (i) AND (ii)

ATSMH$_2$/2,4-Tol/ATSMH$_2$ (i) As per general procedure (14) except with 4-methylthiosemicarbazide (0.41 g, 3.89 mmol), acetic acid (0.5 mL) and mono-keto-(1-methylbenzene-2,4-dithiosemicarbazone) (0.79 g, 1.95 mmol). The product was isolated as a yellow powder (0.71 g, 63%). $^1$H NMR: δ 2.25 (3H, s, CH$_3$); 2.25 (3H, s, CH$_3$); 2.29 (6H, s, CH$_3$); 2.34 (3H, s, PhCH$_3$); 3.03 (6H, d, J 4.40, NHCH$_3$); 7.24 (1H, d, J 8.23, 6-ArH); 7.45 (1H, m, J 7.32, 5-ArH); 7.68 (1H, d, J 1.95, 3-ArH); 8.42 (2H, q, J 4.50, CH$_3$NH); 9.87 (1H, s, PhNH); 9.96 (1H, s, PhNH); 10.29 (1H, s, NH); 10.34 (1H, s, NH); 10.58 (2H, s, NH).

(ii) As per general procedure (13a) except with 4-methylthiosemicarbazide (0.47 g, 4.48 mmol), acetic acid (0.5 mL) and mono-keto-(1-methylbenzene-2,4-dithiosemicarbazone) (0.82 g 2.03 mmol). The product was isolated as a yellow powder (0.90 g, 77%). $^1$H NMR: δ 2.25 (3H, s, CH$_3$); 2.25 (3H, s, CH$_3$); 2.29 (6H, s, CH$_3$); 2.34 (3H, s, PhCH$_3$); 3.03 (6H, d, J 4.40, NHCH$_3$); 7.24 (1H, d, J 8.23, ArH); 7.45 (1H, m, J 7.32, ArH); 7.68 (1H, d, J 1.95, ArH); 8.42 (2H, q, J 4.50, CH$_3$NH); 9.87 (1H, s, PhNH); 9.96 (1H, s, PhNH); 10.29 (1H, s, NH); 10.34 (1H, s, NH); 10.58 (2H, s, NH). $^{13}$C NMR: δ 178.9; 178.6; 177.9; 177.0; 149.8; 149.5; 148.2; 146.9; 138.0; 137.1; 133.1; 132.4; 130.1; 125.5; 31.7; 25.4; 17.8; 12.5; 12.3; 12.1; 10.8. ES MS+: m/z 603.17 (10%, [C$_{21}$H$_{32}$N$_{12}$S$_4$]Na$^+$).

Example 12L

ATSPH$_2$/2,4-Tol/ATSPH$_2$

As per general procedure (14) except with 4-phenylthiosemicarbazide (0.30 g, 1.77 mmol), acetic acid (0.5 mL) and mono-keto-(1-methylbenzene-2,4-dithiosemicarbazone) (0.36 g, 0.89 mmol). The product was isolated as a pale yellow powder (0.38 g, 60%). $^1$H NMR: δ 2.23 (3H, s, PhCH$_3$); 2.33 (12H, s, CH$_3$); 7.22 (2H, t, J 7.56, 4-ArH); 7.28 (1H, d, J 4.61, 5-ArH); 7.38 (4H, t, J 7.77, 3-ArH); 7.47 (1H, m, J 8.12, 5-ArH); 7.57 (4H, d, J 8.10, 2-ArH); 7.68 (1H, d, J 7.65, 3-ArH); 9.92 (2H, s, NHPh); 10.01 (2H, s, NHPh); 10.65 (1H, s, NH); 10.66 (1H, s, NH); 10.67 (1H, s, NH); 10.69 (1H, s, NH).

Example 12M (i) AND (ii)

Zn$_2$[ATSP/CH$_2$CH$_2$/ATSP]

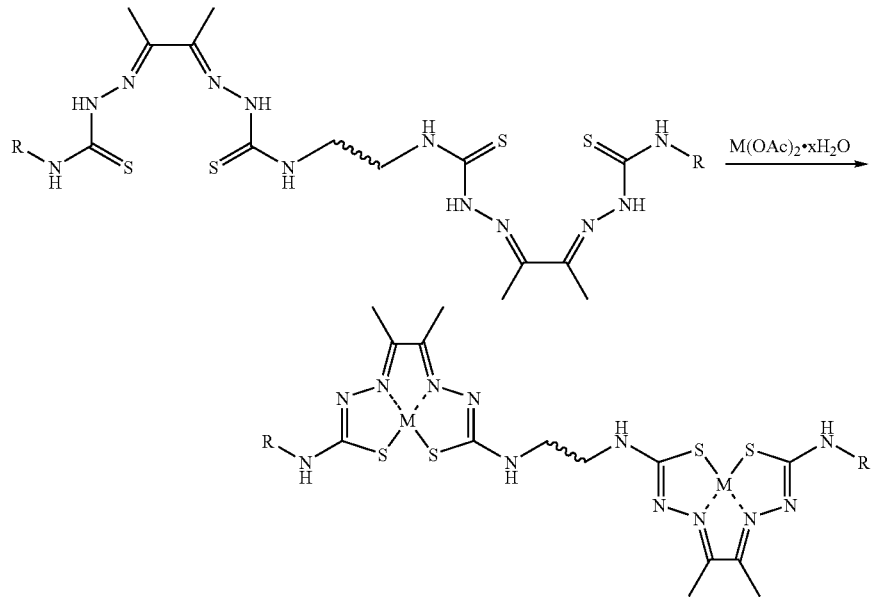

(i) As per general procedure (11) for Zn[ATSM/P] except with ATSPH$_2$—CH$_2$CH$_2$-ATSPH$_2$ (0.62 g, 0.96 mmol) and Zn(OAc)$_2$.2H$_2$O (0.42 g, 1.92 mmol). The product was isolated as a yellow powder (0.53 g, 78%). R$_f$: 44; 49. $^1$H NMR: δ 2.29 (6H, s, CH$_3$); 2.31 (6H, s, CH$_3$); 3.55 (4H, m, CH$_2$); 6.90 (2H, m, J 7.30, 4-ArH) 7.24 (H, m, J 7.87, 3-ArH) 7.57 (H, m, NHCH$_2$); 0.81 (4H, m, J 7.99, 2-ArH); 9.38 (2H, s, NHPh). MS ES+: m/z 705.11 (100%, [Zn[ATSP/CH$_2$CH$_2$/ATSP]H$_2$]H$^+$); 769.02 (50%, [Zn$_2$[ATSP/CH$_2$CH$_2$/ATSP]]H+).

(ii) As per general procedure (13a) except with zinc acetate (0.26 g, 1.18 mmol), ethane-1,2-dithiosemicarbazide (0.11 g, 0.53 mmol) and mono-keto-(4-phenylthiosemicarbazone) (0.26 g, 1.11 mmol). The product was isolated as a yellow powder (0.27 g, 66%). (Found: C, 38.5; H, 4.0; N, 20.75. Calc. for C$_{26}$H$_{30}$N$_2$S$_4$Zn$_2$: C, 40.6; H, 3.9; N, 21.8.) $^1$H NMR: δ 2.29 (6H, s, CH$_3$); 2.31 (6H, s, CH$_3$); 3.55 (4H, m, CH$_2$); 6.90 (2H, t, J 7.30, ArH); 7.24 (4H, t, J 7.87, ArH); 7.57 (2H, s, NHCH$_2$); 7.81 (4H, d, J 7.99, ArH); 9.38 (2H, s, NHPh). $^{13}$C NMR: δ 173.2; 149.4; 141.6; 128.8; 121.8; 120.3; 42.6; 15.2; 14.5. MS ES+: m/z 705.11 (100%, [Zn[ATSP/CH$_2$CH$_2$/ATSP]H$_2$]H$^+$); 769.02 (60%, [Zn$_2$[ATSP/CH$_2$—CH$_2$/ATSP]]H$^+$).

Example 12N

Cu$_2$[ATSP/CH$_2$CH$_2$/ATSP]

As per general procedure (11) except with ATSPH$_2$—CH$_2$CH$_2$-ATSPH$_2$ (0.10 g, 0.16 mmol) and Cu(OAc)$_2$.H$_2$O (0.06 g, 0.31 mmol). The product was isolated as a brown powder (0.05 g, 42%). (Found: Cu, 13.0%. Calc. for C$_{26}$H$_{30}$Cu$_2$N$_{12}$S$_4$: Cu, 16.6%.) R$_f$: 46; 52; 59. MS MALDI: m/z 703.11 (100%, [CuLH$_2$]$^+$); 764.03 (50%, [Cu$_2$L]$^+$).

Example 12O

Ni$_2$[ATSP/CH$_2$CH$_2$/ATSP]

As per general procedure (11) except with ATSPH$_2$—CH$_2$CH$_2$-ATSPH$_2$ (0.32 g, 0.50 mmol) and Ni(OAc)$_2$.4H$_2$O (0.25 g, 1.00 mmol). The product was isolated as a brown/green powder (0.25 g, 67%). R$_f$: 46; 52; 53; 60. MS ES+: m/z 755.03 (100%, [Ni$_2$L]H$^+$).

Example 12P

Zn$_2$[ATSM/2,4-Tol/ATSM]

As per general procedure (11) except with ATSMH$_2$-2,4-Tol-ATSMH$_2$ (0.24 g, 4.19 mmol) and Zn(OAc)$_2$.H$_2$O (0.18 g, 0.84 mmol). The product was isolated as a yellow powder (0.20 g, 68%). R$_f$: 41; 43. $^1$H NMR: δ 2.10 (3H, s, CH$_3$); 2.12 (3H, s, CH$_3$); 2.18 (3H, s, CH$_3$); 2.22 (3H, s, CH$_3$); 2.24 (3H, s, PhCH$_3$); 2.84 (6H, m, NHCH$_3$); 7.02 (1H, d, J 8.52, 6-ArH); 7.31 (1H, m, CH$_3$NH); 7.37 (1H, m, CH$_3$NH); 7.49 (1H, m, J 8.35, 5-ArH); 7.93 (1H, d, J 1.84, 3-ArH); 8.60 (1H, s, PhNH); 9.29, (1H, s, PhNH). MS ES+: 643.10 (100%, [ZnLH$_2$]H$^+$); 707.01 (5%, [Zn$_2$L]$^+$).

Example 12Q

Cu$_2$[ATSM/2,4-Tol/ATSM]

As per general procedure (11) except with ATSMH$_2$-2,4-Tol-ATSMH$_2$ (0.17 g, 0.30 mmol) and Cu(OAc)$_2$.H$_2$O (0.12 g, 0.59 mmol). The product was isolated as a brown powder (0.12 g, 56%). (Found: Cu, 13.9%. Calc. for C$_{21}$H$_{28}$Cu$_2$N$_{12}$S$_4$: Cu, 18.1%.) MS MALDI: m/z 1282.18 (100%, [CuLH$_2$]$_2^+$).

Example 12R

Ni$_2$[ATSM/2,4-Tol/ATSM]

As per general procedure (11) except with ATSMH$_2$-2,4-Tol-ATSMH$_2$ (0.14 g, 0.24 mmol) and Ni(OAc)$_2$.4H$_2$O (0.12 g, 0.48 mmol). The product was isolated as a brown/green powder (0.12 g, 72%). $^1$H NMR: δ 1.87 (3H, s, CH$_3$); 1.94 (3H, s, CH$_3$); 1.99 (3H, s, CH$_3$); 2.07 (3H, s, CH$_3$); 2.11 (3H, s, PhCH$_3$); 2.80 (6H, m, NHCH$_3$); 7.06 (1H, d, J 8.32, 6-ArH); 7.27 (1H, m, J 9.10, 5-ArH); 7.69 (1H, m, 3-ArH); 7.80 (1H, m, CH$_3$NH); 7.87 (1H, m, CH$_3$NH); 9.37 (1H, s, PhNH); 9.87 (1H, s, PhNH). MS ES+: m/z 693.02 (80%, [Ni$_2$L]H$^+$).

Example 12S

Zn$_2$[ATSP/CH$_2$CH$_2$/ATSP]

General Procedure (15)

(2H, t, J 7.30, 4-ArH); 7.24 (4H, t, J 7.87, 3-ArH); 7.57 (2H, s, NHCH$_2$); 7.81 (4H, d, J 7.99, 2-ArH); 9.38 (2H, s, NHPh). MS ES+: m/z 705.11 (100%, [ZnLH$_2$]H$^+$); 769.02 (60%, [Zn$_2$L]H$^+$).

Example 12T

Zn [ATSM/2,4-Tol/ATSM]

As per general procedure (15) except with Zn(OAc)$_2$.2H$_2$O (0.22 g, 1.00 mmol), 1-methylbenzene-2,4-dithiosemicarbazone (0.10 g, 0.50 mmol) and 4-methylthiosemicarbazide (0.11 g, 1.00 mmol). The product was isolated as a yellow/orange powder (0.23 g, 64%). R$_f$: 41; 43. (Found: Zn, 17.1%. Calc. for C$_{21}$H$_{28}$N$_{12}$S$_4$Zn$_2$: Zn, 18.5%.) $^1$H NMR: δ 2.10 (3H, s, CH$_3$); 2.12 (3H, s, CH$_3$); 2.18 (3H, s, CH$_3$); (2.22, 3H, s, CH$_3$); 2.24 (3H, s, PhCH$_3$); 2.84 (6H, s, NHCH$_3$); 7.02 (1H, d, J 8.52, 6-ArH); 7.31 (1H, s, CH$_3$NH); 7.37 (1H, m, CH$_3$NH); 7.49 (1H, s, J 8.35, 5-ArH); 7.93 (1H, d, J 1.84, 3-ArH); 8.60 (1H, s, PhNH); 9.29 (1H, s, PhNH). MS ES+: m/z 643.10 (100%, [ZnLH$_2$]H$^+$).

Example 12U

Zn$_2$[ATSP/1,4-Ph/ATSP]

As per general procedure (13a) (see Example 12D) except with zinc acetate (0.40 g, 1.82 mmol), benzene-1,4-dithiosemicarbazide (0.21 g, 0.82 mmol) and mono-keto-(4-phenylthiosemicarbazone) (0.39 g, 1.67 mmol). The product was isolated as an orange powder (0.46 g, 69%). (Found: C, 42.3; H, 3.6; N, 19.4. Calc. for C$_{30}$H$_{30}$N$_{12}$S$_4$Zn$_2$: C, 44.1; H, 3.7; N, 20.6.) $^1$H NMR: δ 2.34 (6H, s, CH$_3$); 2.34 (6H, s, CH$_3$); 6.93 (2H, t, J 7.32, ArH); 7.26 (4H, t, J 7.88, ArH); 7.69 (4H, s,

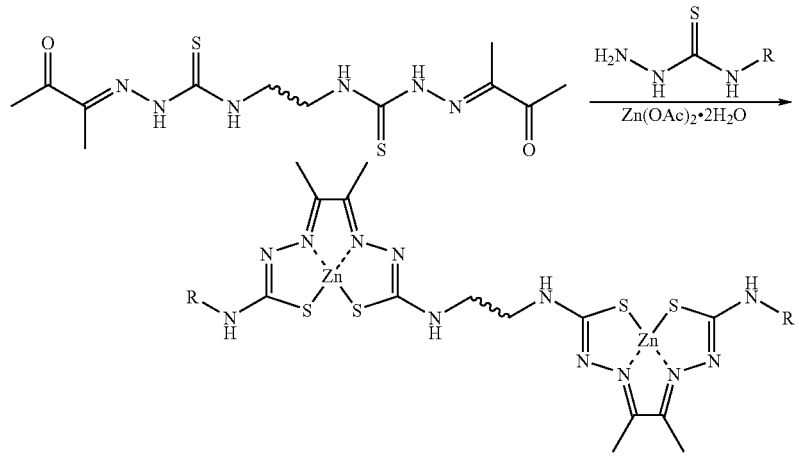

A solution of Zn(OAc)$_2$.2H$_2$O (0.44 g, 2.00 mmol) was added to a solution of ethane-1,2-dithiosemicarbazone (0.34 g, 1.00 mmol) in methanol (30 mL) and stirred for 5 min. 4-phenylthiosemicarbazide (0.33 g, 2.00 mmol) was added and the mixture was heated under reflux for 16 h and allowed to cool slowly to room temperature. The yellow solid that formed was collected by filtration, washed with methanol and diethyl ether and dried in vacuo. The product was isolated as a yellow powder (0.52 g, 68%). (Found: Zn, 20.1%. Calc. for C$_{26}$H$_{30}$N$_{12}$S$_4$Zn$_2$: Zn, 17.0%.) R$_f$: 44; 49; 56. $^1$H NMR: δ 2.29, 6H, s, CH$_3$; 2.31 (6H, s, CH$_3$); 3.55 (4H, m, CH$_2$); 6.90

ArH); 7.82 (4H, d, J 7.90, ArH); 9.45 (2H, s, PhNH); 9.48 (2H, s, PhNH). $^{13}$C NMR: δ 173.6; 173.5; 149.0; 148.1; 141.5; 135.9; 128.8; 122.0; 120.7; 120.4; 15.2; 15.1. MS MALDI: 819.51 (100%, [Zn$_2$[ATSP/1,4-Ph/ATSP]]H$^+$).

Example 12V

Zn$_2$[ATSP/2,4-Tol/ATSP]

As per general procedure (13a) except with zinc acetate (0.25 g, 1.14 mmol), 1-methylbenzene-2,4-dithiosemicarbazide (0.15 g, 0.56 mmol) and mono-keto-(4-phenylthiosemicarbazone) (0.26 g, 1.11 mmol). The product was isolated as a yellow/orange powder (0.31 g, 68%). (Found: C, 43.8; H, 3.85; N, 19.6. Calc. for $C_{31}H_{32}N_{12}S_4Zn_2$: C, 44.8; H, 3.9; N, 20.2.) $^1$H NMR: δ 9.45 (1H, s, NH); 9.44 (1H, s, NH); 9.39 (1H, s, NH); 8.82 (1H, s, NH); 7.92 (1H, d, J 2.3, ArH); 7.79 (4H, d, J 8.2, PhH); 7.51 (1H, dd, J 8.2 and 2.1, ArH); 7.23 (4H, t, J 8.2, PhH); 7.04 (1H, d, J 8.5, ArH); 6.90 (2H, t, J 8.2, PhH); 2.31 (3H, s, ArCH$_3$); 2.27 (6H, s, CH$_3$); 2.13 (6H, s, CH$_3$). $^{13}$C NMR: δ 176.3; 173.7; 173.6; 173.4; 149.2; 149.0; 148.5; 146.7; 141.6; 141.5; 139.2; 138.8; 129.9; 128.8; 126.8; 122.0; 121.9; 120.4; 120.3; 119.2; 117.5; 18.1; 15.2; 15.1; 14.6. MS MALDI: 833.11 (100%, [Zn$_2$[ATSP/2,4-Tol/ATSP]]H$^+$).

Example 12W

Zn$_2$[ATSM/CH$_2$CH$_2$/ATSM]

As per general procedure (13a) except with zinc acetate (0.30 g, 1.37 mmol), ethane-1,2-dithiosemicarbazide (0.13 g, 0.63 mmol) and mono-keto-(4-methylthiosemicarbazone) (0.22 g, 1.27 mmol). The product was isolated as a yellow powder (0.27 g, 68%). (Found: C, 29.2; H, 4.2; N, 25.4. Calc. for $C_{16}H_{26}N_{12}S_4Zn_2$: C, 29.8; H, 4.1; N, 26.0.) (Mass: 642.9925. Calc. for $C_{16}H_{27}N_{12}S_4Zn_2$: 642.9947.) $^1$H NMR: δ 2.20 (6H, s, CH$_3$); 2.23 (6H, s, CH$_3$); 2.82 (6H, d, J 4.11, CH$_3$); 3.51 (4H, m, CH$_2$); 7.24 (2H, s, NH); 7.38 (2H, s, NH). MS ES+: 642.99 (100%, [Zn$_2$[ATSM/CH$_2$CH$_2$/ATSM]]H$^+$). $^{13}$C NMR: δ 179.0; 146.0; 145.5; 48.6; 29.2; ~12.

Example Section 13

Bis(thiosemicarbazone) Formation from Monothiosemicarbazones and Diacetyl Dihydrazone Example 13A

ATSM/PH$_2$

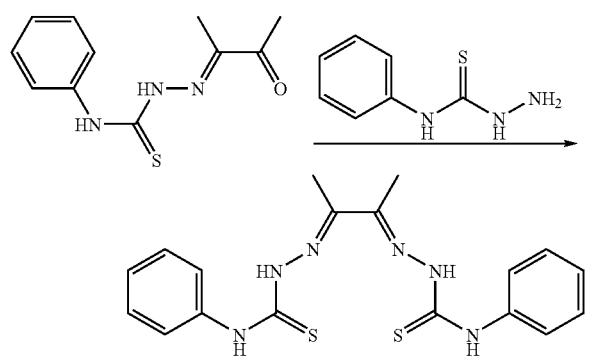

As per general procedure (10) for ATSM/PH$_2$ except with mono-keto-(4-phenylthiosemicarbazone) (0.24 g, 1.00 mmol), acetic acid (0.25 mL) and 4-phenylthiosemicarbazide (0.17 g, 1.00 mmol). The product was isolated as a cream solid (0.22 g, 57%). $^1$H NMR: δ 2.33 (6H, s, CH$_3$); 7.22 (2H, t, J 7.34, 4-ArH); 7.38 (4H, t, J 7.76, 3-ArH); 7.57 (4H, d, J 7.63, 2-ArH); 10.00 (2H, s, NHPh); 10.67 (2H, s, NH).

Example 13B

ATSM/PH$_2$

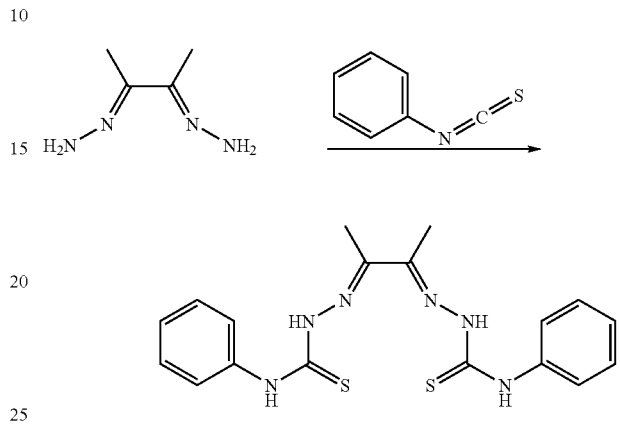

A solution of phenylisothiocyanate (0.34 mL, 2.81 mmol) in ethanol (5 mL) was added to a boiling solution of diacetyl dihydrazone (0.16 g, 1.40 mmol) in ethanol (25 mL). The mixture was heated under reflux for 1 h and allowed to cool slowly to room temperature. The resulting yellow solid was collected by filtration, washed with ethanol and diethyl ether and dried in vacuo. The product was isolated as a pale yellow powder (0.46 g, 86%). $^1$H NMR: δ 2.33 (6H, s, CH$_3$); 7.22 (2H, t, J 7.34, 4-ArH); 7.38 (4H, t, J 7.76, 3-ArH); 7.57 (4H, d, J 7.63, 2-ArH); 10.00 (2H, s, NHPh); 10.67 (2H, s, NH).

Example 13C

Mono-hydrazone-(4-phenylthiosemicarbazone

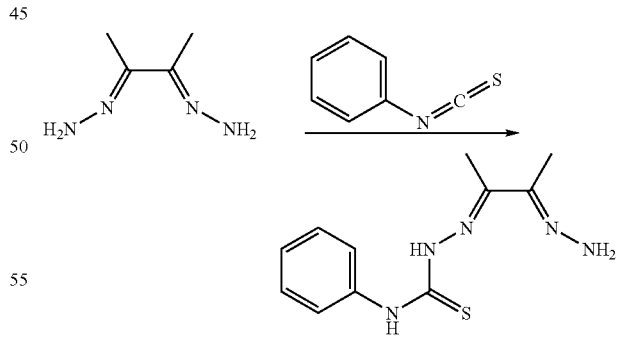

A solution of phenylisothiocyanate (0.15 mL, 1.23 mmol) in ethanol (5 mL) was added to a boiling solution of diacetyl dihydrazone (0.14 g, 1.23 mmol) in ethanol (25 mL). The mixture was heated under reflux for 30 min and then allowed to cool slowly to room temperature. The resulting yellow solid was collected by filtration, washed with ethanol and diethyl ether and dried in vacuo. The product was isolated as a yellow powder (0.23 g, 75%). $^1$H NMR: δ 2.08 (3H, s, CH$_3$);

2.28 (3H, s, CH$_3$); 7.22 (1H, t, J 7.33, 4-ArH); 7.38 (2H, t, J 7.72, 3-ArH); 7.55 (2H, d, J 7.57, 2-ArH); 10.01 (1H, s, NHPh); 10.80 (1H, s, NH).

Example Section 14

ATSM/AH$_2$ and ATSP/AH$_2$

Example 14A

ATSM/AH$_2$

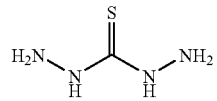
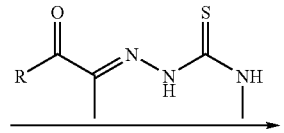
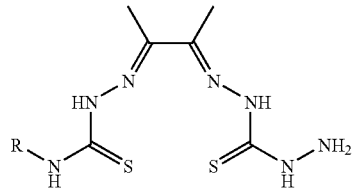

Thiocarbhydrazide (3.02 g, 28.49 mol) and conc. HCl (0.5 mL) were added to ethanol (50 mL) and heated to 60° C. Mono-keto-(4-methylthiosemicarbazone) (4.93 g, 28.49 mmol) was added as a solution in ethanol (15 mL) in portions over 2 h. The mixture was heated under reflux under an atmosphere of nitrogen for 4 h. A pale yellow precipitate was collected by filtration, washed with ethanol and diethyl ether and dried in vacuo. The product was isolated as a pale yellow solid (5.74 g, 77%). (Found: C, 32.8; H, 6.0; N, 36.5. Calc. for C$_7$H$_{15}$N$_7$S$_2$: C, 32.2; H, 5.8; N, 37.5.) and (Found: C, 32.0; H, 6.2; N, 36.3; S, 24.7. Calc. for C$_7$H$_{15}$N$_7$S$_2$: C, 32.2; H, 5.8; N, 37.5; S, 24.5.). R$_f$: 33; 43; 49. $^1$H NMR: δ 2.18 (3H, s, CH$_3$); 2.19 (3H, s, CH$_3$); 3.01 (3H, d, J 4.49, NHCH$_3$); 4.96 (2H, s, NH$_2$); 8.37 (1H, q, J 4.49, NHCH$_3$); 9.70 (1H, s, NHNH$_2$); 10.21 (1H, s, NH); 10.23 (1H, s, NH). $^{13}$C NMR: δ 11.27; 11.31; 30.87; 147.76; 148.14; 175.55; 178.07. MS ES+: m/z 262.09 (80%, [C$_7$H$_{15}$N$_7$S$_2$]H$^+$) and m/z 284.08 (100%, [C$_7$H$_{15}$N$_7$S$_2$]Na$^+$).

Example 14B

ATSP/AH$_2$

Mono-keto-(4-phenyl-thiosemicarbazone) (1.79 g, 7.61 mmol) and conc. HCl (5 drops) were added to ethanol (30 mL) and heated to 60° C. Thiocarbhydrazide (0.73 g, 6.84 mmol) was added in portions over 2 h. The mixture was heated under reflux under an atmosphere of nitrogen for 4 h. A yellow precipitate was collected by filtration, washed with ethanol and diethyl ether and dried in vacuo. The product was isolated as a yellow/orange solid (2.03 g, 83%). $^1$H NMR: δ 2.25 (3H, s, CH$_3$); 2.28 (3H, s, CH$_3$); 7.20 (1H, t, J 6.77, 4-ArH); 7.37 (2H, t, J 7.83, 3-ArH); 7.57 (2H, d, J 7.52, 2-ArH); 10.04 (1H, s, NHPh); 10.67 (1H, s, NHNH$_2$).

EXAMPLES SECTION 15

Metal complexes of ATSR/AH$_2$

Example 15A

Zn[ATSM/A]

General Procedure (16)

ATSM/AH$_2$ (0.26 g, 1.00 mmol) and zinc acetate (Zn(OAc)$_2$.2H$_2$O) (0.24 g, 1.10 mmol) were added to methanol (30 mL). The mixture was heated under reflux for 3 h under an atmosphere of nitrogen and allowed to cool slowly to room temperature. A yellow powder formed which was washed with methanol and diethyl ether and dried in vacuo. The product was isolated as a dark yellow solid (0.19 g, 59%). (Found: C, 26.5; H, 4.2; N, 29.5. Calc. for C$_7$H$_{13}$N$_7$S$_2$Zn: C, 25.9; H, 4.0; N, 30.2.) (Mass: 324.0053. Calc. mass for C$_7$H$_{14}$N$_7$S$_2$Zn: 324.0044.) R$_f$: 29; 43. $^1$H NMR: δ 2.21 (3H, s, CH$_3$); 2.23 (3H, s, CH$_3$); 2.82 (3H, d, J 4.13, NHCH$_3$); 4.50 (2H, s, NH$_2$); 7.25 (1H, s, NHCH$_3$); 8.25 (1H, s, NHNH$_2$). $^{13}$C NMR: δ 13.84; 13.90; 29.17; 48.55; 145.68; 177.10. MS ES+: m/z 324.01 (100%, Zn[ATSM/A]H$^+$).

Example 15B

Cu[ATSM/A]

As per general procedure (16) except with ATSM/AH$_2$ (0.27 g, 1.02 mmol) and Cu(OAc)$_2$.H$_2$O (0.22 g, 1.12 mmol). The product was isolated as a black solid (0.26 g, 78%). (Found: C, 25.7 H, 3.7; N, 30.4. Calc. for C$_7$H$_{13}$N$_7$S$_2$Cu: C, 26.0; H, 4.0; N, 30.4.) R$_f$: 18; 25; 32. MS ES+: m/z 323.01 (100%, Cu[ATSM/A]H$^+$).

Example 15C

Ni[ATSM/A]

As per general procedure (16) except with ATSM/AH$_2$ (0.35 g, 1.33 mmol) and Ni(OAc)$_2$.4H$_2$O (0.36 g, 1.46 mmol). The product was isolated as a black solid (0.39 g, 92%). $^1$H NMR: δ 1.95 (6H, s, CH$_3$); 2.78 (3H, d, J 4.05, NHCH$_3$); 4.86 (2H, s, NH$_2$); 7.69 (1H, s, NHCH$_3$); 8.88 (1H, s, NHNH$_2$). MS ES+: m/z 318.01 (100%, Ni[ATSM/A]H$^+$).

Example 15D

Zn[ATSP/A]

As per general procedure (16) except with ATSP/AH$_2$ (0.35 g, 1.08 mmol) and Zn(OAc)$_2$.2H$_2$O (0.24 g, 1.09 mmol). The product was isolated as an orange solid (0.25 g, 61%). $^1$H NMR: δ 2.29 (3H, s, CH$_3$); 2.32 (3H, s, CH$_3$); 4.96 (2H, s, NH$_2$); 6.91 (1H, t, J 7.29, 4-ArH); 7.24 (2H, t, J 7.83, 3-ArH); 7.80 (2H, d, J 7.86, 2-ArH); 8.73 (1H, s, NHNH$_2$); 9.41 (1H, s, NHPh).

Example 15E

Zn[ATSM/A-butane-2,3-dione]

General Procedure (17)

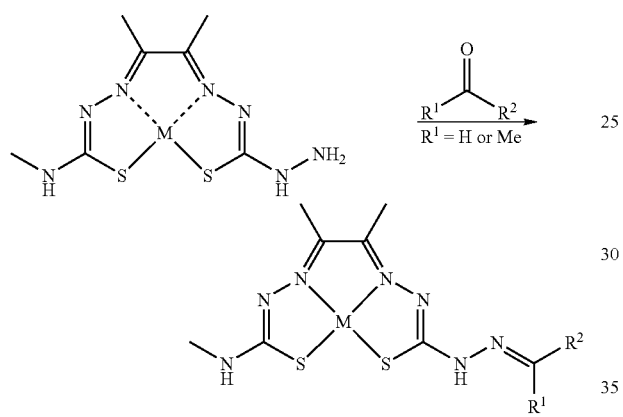

Zn[ATSM/A] (0.20 g, 0.62 mmol) and butane-2,3-dione (0.11 mL, 1.23 mmol) were added to methanol (20 mL). The mixture was heated under reflux for 3 h under an atmosphere of nitrogen and allowed to cool slowly to room temperature. A bright orange powder formed which was washed with methanol and diethyl ether and dried in vacuo. The product was isolated as a bright orange solid (0.16 g, 65%). R$_f$: 30. (Mass: 392.0311. Calc. mass for C$_{11}$H$_{18}$N$_7$OS$_2$Zn: 392.0306) (Found: C, 33.8; H, 4.5; N, 23.7; S, 15.9; Zn, 16.7. Calc. for C$_{11}$H$_{17}$N$_7$OS$_2$Zn: C, 33.6; H, 4.4; N, 25.0; S, 16.3; Zn, 16.7.). $^1$H NMR: δ 1.94 (3H, s, CH$_3$); 2.24 (3H, s, CH$_3$); 2.31 (3H, s, CH$_3$); 2.34 (3H, s, CH$_3$); 2.86 (3H, s, NHCH$_3$); 7.49 (1H, s, NHCH$_3$); 10.62 (1H, s, NHNR). $^{13}$C NMR: δ 9.46; 13.81; 14.33; 23.95; 29.20; 144.30; 151.45; 177.46; 197.24. MS ES+: m/z 392.03 (100%, Zn[ATSM/A-butane-2,3-dione]H$^+$).

Example 15F

Zn[ATSM/A-terephthaldehyde]

As per general procedure (17) except with Zn[ATSM/A] (0.34 g, 1.06 mmol) and terephthalaldehyde (0.28 g, 2.12 mmol). The product was isolated as an orange/red solid (0.39 g, 82%). (Found: C, 40.0; H, 4.5; N, 21.6. Calc. for C$_{15}$H$_{17}$N$_7$OS$_2$Zn: C, 40.9; H, 3.9; N, 22.3.) R$_f$: 34. (Mass: 440.0288. Calc. mass for C$_{15}$H$_{17}$N$_7$OS$_2$Zn: 440.0306) $^1$H NMR: δ 2.23 (3H, s, CH$_3$); 2.29 (3H, s, CH$_3$); 2.85 (3H, s, NHCH$_3$) 7.41 (1H, s, NHCH$_3$); 7.82 (2H, d, J 8.19, 3-ArH); 7.93 (2H, d, J 8.13, 2-ArH); 8.17 (1H, s, C(N)H); 10.00 (1H, s, C(O)H); 11.58 (1H, s, NHNR). $^{13}$C NMR: δ 13.52; 13.93; 126.32; 129.68; 135.44; 139.33; 140.68; 148.86; 192.20. MS ES+: m/z 440.10 (100%, Zn[ATSM/A-terephthalaldehyde]H$^+$.

Example 15G

Zn[ATSM/A-isophthalaldehyde]

As per general procedure (17) except with Zn[ATSM/A] (0.16 g, 0.48 mmol) and isophthalaldehyde (0.13 g, 0.97 mmol). The product was isolated as an orange/red solid (0.08 g, 38%). (Mass: 440.0308. Calc. mass for C$_{15}$H$_{17}$N$_7$OS$_2$Zn: 440.0306) $^1$H NMR: δ 2.23 (3H, s, CH$_3$); 2.29 (3H, s, CH$_3$); 2.85 (3H, s, NHCH$_3$); 7.38 (1H, s, NHCH$_3$); 7.64 (1H, t, J 7.64, 5-ArH); 7.87 (1H, d, J 7.64, 6-ArH); 7.94 (1H, d, J 7.71, 4-ArH); 8.13 (1H, s, 2-ArH); 10.06 (1H, s, C(O)H); 11.45 (1H, s, NHNR). $^{13}$C NMR: δ 13.81; 14.18; 126.83; 129.48; 129.59; 131.80; 136.20; 136.55; 139.95; 148.65; 193.11. MS ES+: m/z 440.03 (100%, Zn[ATSM/A-isophthalaldehyde]H$^+$).

Example 15H

Zn[ATSM/A-glyoxal]

As per general procedure (17) except with Zn[ATSM/A] (0.17 g, 0.52 mmol) and glyoxal (0.07 mL, 0.52 mmol). The product was isolated as a dark red solid (0.08 g, 40%). $^1$H NMR: δ 2.22 (3H, s, CH$_3$); 2.25 (3H, s, CH$_3$); 2.85 (3H, s, NHCH$_3$); 7.39 (1H, s, NHCH$_3$); 7.55 (1H, d, J 7.97, C(N)H); 9.48 (1H, d, J 7.92, C(O)H); 11.45 (1H, s, NHNR). MS ES+: m/z 364.00 (75%, Zn[ATSM/A-glyoxal]H$^+$).

Example 15I

Zn[ATSM/A-phenylglyoxal]

As per general procedure (17) except with Zn[ATSM/A] (0.24 g, 0.73 mmol) and phenylglyoxal (0.20 g, 1.47 mmol). The product was isolated as a dark red solid (0.24 g, 75%). (Found: C, 41.0; H, 4.3; N, 22.1. Calc. for C$_{15}$H$_{17}$N$_7$OS$_2$Zn: C, 40.9; H, 3.9; N, 22.3) R$_f$: 39. (Mass: 440.0312. Calc. mass for C$_{15}$H$_{17}$N$_7$OS$_2$Zn: 440.0306) $^1$H NMR: δ 2.24 (3H, s, CH$_3$); 2.31 (3H, s, CH$_3$); 2.86 (3H, s, NHCH$_3$); 7.50 (2H, t, J 7.50, 3-ArH); 7.61 (2H, t, J 7.27, 4-ArH); 7.87 (1H, s, C(N)H); 8.28 (2H, d, J 7.32, 2-ArH); 12.06 (1H, s, NHNR). $^{13}$C NMR: δ 13.62; 14.12; 127.94; 130.11; 132.37; 135.60; 136.03; 138.04; 188.50. MS ES+: m/z 440.04 (100%, Zn[ATSM/A-phenylglyoxal]H$^+$).

Example 15J

Zn[ATSM/A-pyruvic acid]

As per general procedure (17) except with Zn[ATSM/A] (0.16 g, 0.48 mmol) and pyruvic acid (0.07 mL, 0.96 mmol). The product was isolated as a yellow powder (0.12 g, 65%). R$_f$: 22, 33. $^1$H NMR: δ 2.18 (3H, s, CH$_3$); 2.22 (3H, s, CH$_3$); 2.26 (3H, s, CH$_3$); 2.83 (3H, d, J 3.11, NHCH$_3$); 7.35 (1H, bs, NHCH$_3$); 8.90 (1H, s, OH); 10.11 (1H, s, NHNR). $^{13}$C NMR: δ 11.68; 14.38; 29.69; 31.61; 146.64; 149.45; 166.67; 177.93; 178.70. MS ES+: m/z 394.07 (80%, Zn[ATSM/A-pyruvic acid]H$^+$).

Example 15K

Zn[ATSM/A-benzaldehyde]

As per general procedure (17) except with Zn[ATSM/A] (0.21 g, 0.63 mmol) and benzaldehyde (0.13 mL, 1.27 mmol). The product was isolated as a yellow solid (0.27 g, 54%). $R_f$: 37. (Mass: 412.0368. Calc. mass for $C_{14}H_{18}N_7S_2Zn$: 412.0357) (Found: C, 40.7; H, 4.6; N, 23.5; S, 15.9. Calc. for $C_{14}H_{17}N_7S_2Zn$: C, 40.7; H, 4.15; N, 23.8; S, 15.5). $^1H$ NMR: δ 2.23 (3H, s, $CH_3$); 2.27 (3H, s, $CH_3$); 2.85 (3H, d, J 2.74, $NHCH_3$); 7.34 (1H, t, J 7.11, 4-ArH); 7.35 (1H, s, $NHCH_3$); 7.41 (2H, t, J 7.19, 3-ArH); 7.62 (2H, d, J 7.00, 2-ArH); 8.11 (1H, s, C(N)H); 11.30 (1H, s, NHNR). $^{13}C$ NMR: 614.29; 14.62; 126.76; 129.15; 129.34; 135.64; 141.87; 148.66. MS ES+: m/z 412.04 (100%, Zn[ATSM/A-benzaldehyde]H+).

Example 15L

Zn[ATSM/A-salicylaldehyde]

As per general procedure (17) except with Zn[ATSM/A] (0.16 g, 0.49 mmol) and salicylaldehyde (0.10 mL, 0.98 mmol). The product was isolated as an orange powder (0.10 g, 46%). (Mass: 428.0301. Calc. mass for $C_{14}H_{18}N_7OS_2Zn$: 428.0306) (Mass: 428.0301. Calc. mass for $C_{14}H_{18}N_7OS_2Zn$: 428.0306) (Found: C, 38.6; H, 4.7; N, 21.9; S, 14.9. Calc. for $C_{14}H_{17}N_7S_2Zn$: C, 39.2; H, 4.0; N, 22.9; S, 15.0.). $^1H$ NMR: δ 2.24 (3H, s, $CH_3$); 2.28 (3H, s, $CH_3$); 2.86 (3H, m, $NHCH_3$); 6.86 (1H, m, 3-ArH); 6.89 (1H, m, 5-ArH); 7.23 (1H, t, J 7.13, 4-ArH); 7.32 (1H, d, J 7.63, 6-ArH); 7.43 (1H, s, $NHCH_3$); 8.22 (1H, s, C(N)H); 11.57 (1H, s, NHNR); 11.78 (1H, s, OH). $^{13}C$ NMR: 613.79; 14.03; 116.34; 118.75; 119.07; 129.75; 130.07; 142.90; 149.28; 157.13. MS ES+: m/z 428.03 (100% Zn[ATSM/A-salicylaldehyde]H+).

Example 15M

Zn[ATSM/A-2-hydroxynaphthaldehyde]

As per general procedure (17) except with Zn[ATSM/A] (0.18 g, 0.55 mmol) and 2-hydroxynapthaldehyde (0.19 g, 1.10 mmol). The product was isolated as a dark yellow powder (0.15 g, 58%). (Mass: 478.0448. Calc. mass for $C_{18}H_{20}N_7OS_2Zn$: 478.0462.) (Found: C, 43.3; H, 4.9; N, 18.9; S, 12.8. Calc. for $C_8H_{21}N_7O_2S_2Zn$ [M+$H_2O$]: C, 43.5; H, 4.3; N, 19.7; S, 12.9). $^1H$ NMR: δ 2.23 (3H, s, $CH_3$); 2.30 (3H, s, $CH_3$); 2.85 (3H, s, $NHCH_3$); 7.19 (1H, d, J 8.94, ArH); 7.37 (1H, t, J 7.44, ArH); 7.42 (1H, s, $NHCH_3$); 7.56 (1H, t, J 7.50, ArH); 7.83 (1H, d, J 5.87, ArH); 7.86 (1H, d, J 4.68, ArH); 8.02 (1H, d, J 8.45, ArH); 9.15 (1H, s, C(N)H); 11.55 (1H, s, NHNR); 13.00 (1H, s, OH). $^{13}C$ NMR: δ 13.53; 13.78; 48.29; 109.03; 119.13; 120.17; 123.38; 127.45; 127.78; 128.97; 131.35; 140.34; 157.10. MS ES+: m/z 478.04 (100%, Zn[ATSM/A-2-hydroxynaphthaldehyde]H+).

Example 15N

Zn[ATSM/A-2-furaldehyde]

As per general procedure (17) except with Zn[ATSM/A] (0.36 g, 1.10 mmol) and 2-furaldehyde (0.18 mL, 2.20 mmol). The product was isolated as a yellow/orange powder (0.27 g, 62%). (Mass: 402.0145. Calc. mass for $C_{12}H_{16}N_7OS_2Zn$: 402.0149.) (Found: C, 35.8; H, 4.4; N, 23.8; S, 15.8; Zn, 16.2. Calc. for $C_{12}H_{15}N_7OS_2Zn$: C, 35.8; H, 3.8; N, 24.3; S, 15.9; Zn, 16.3.). $^1H$ NMR: δ 2.22 (3H, s, $CH_3$); 2.26 (3H, s, $CH_3$); 2.84 (3H, m, $NHCH_3$); 6.58 (1H, m, 4-ArH); 6.73 (1H, d, J 3.20, 5-ArH); 7.37 (1H, m, $NHCH_3$); 7.78 (1H, m, 3-ArH); 8.02 (1H, s, C(N)H); 11.21 (1H, s, NHNR). $^{13}C$ NMR: δ 13.82; 14.19; 29.20; 48.57; 111.42; 112.01; 131.97; 144.13; 148.21; 150.06. MS ES+: m/z 402.01 (100%, Zn[ATSM/A-2-furaldehyde]H+).

Example 15O

Zn[ATSM/A-4-(dipropylamino)benzaldehyde]

As per general procedure (17) except with Zn[ATSM/A] (0.44 g, 1.36 mmol) and 4-(dipropylamino)benzaldehyde (0.30 g, 1.46 mmol). The product was isolated as a bright red powder (0.26 g, 39%). (Mass: 511.1416. Calc. mass for $C_{20}H_{31}N_8S_2Zn$: 511.1405) $^1H$ NMR: δ 0.89 (6H, t, J 7.29, $CH_2CH_2CH_3$); 1.54 (4H, m, J 7.21, $CH_2CH_2CH_3$); 2.22 (3H, s, $CH_3$); 2.26 (3H, s, $CH_3$); 2.85 (3H, d, J 3.05, $NHCH_3$); 6.65 (2H, d, J 8.75, 3-ArH); 7.29 (1H, s, $NHCH_3$); 7.40 (2H, d, J 8.65, 2-ArH); 7.96 (1H, s, C(N)H); 10.97 (1H, s, NHNR). $^{13}C$ NMR: δ 11.14; 13.83; 14.03; 19.97; 51.78; 111.10; 121.53; 127.93; 142.7; 148.40. MS ES+: m/z 511.14 (100%, Zn[ATSM/A-4-(dipropylamino)benzaldehyde]H+).

Example 15P (i) AND (ii)

Zn[ATSM/A-propionaldehyde]

(i) As per general procedure (17) except with Zn[ATSM/A] (0.20 g, 0.63 mmol) and propionaldehyde (0.05 mL, 0.69 mmol). The product was isolated as a yellow/orange oil (0.18 g, 80%). $^1H$ NMR: δ 1.01 (3H, t, J 7.51, $CH_2CH_3$); 2.21 (3H, s, $CH_3$); 2.21 (3H, s, $CH_3$); 2.83 (3H, s, $NHCH_3$); 3.38 (2H, m, $CH_2CH_3$); 7.29 (1H, bs, $NHCH_3$); 7.41 (1H, t, J 5.34, C(N)H); 11.78 (1H, s, NHNR).

(ii) As per general procedure (17) except with Zn[ATSM/A] (0.18 g, 0.55 mmol) and propionaldehyde (0.05 mL, 0.65 mmol). The solvent was removed from the reaction mixture with a rotary evaporator. The crude product was redissolved in methanol and precipitated with water. The product was washed with diethyl ether and dried in vacuo. The product was isolated as a yellow solid (0.10 g, 50%). (Mass: 364.0350. Calc. mass for $C_{10}H_{18}N_7S_2Zn$: 364.0357.) $^1H$ NMR: δ 1.01 (3H, t, J 7.51, $CH_2CH_3$); 2.21 (3H, s, $CH_3$); 2.21 (3H, s, $CH_3$); 2.83 (2H, m, $CH_2CH_3$); 3.01 (3H, s, $NHCH_3$); 7.29 (1H, s, $NHCH_3$); 7.41 (1H, t, J 5.34, C(N)H); 11.78 (1H, s, NHNR). MS ES+: m/z 364.04 (100%, Zn[ATSM/A-propionaldehyde]H+).

Example 15Q

Zn[ATSM/A-4-fluorobenzaldehyde]

As per general procedure (17) except with Zn[ATSM/A] (0.13 g, 0.41 mmol) and 4-fluorobenzaldehyde (0.09 mL, 0.81 mmol). The product was isolated as a yellow powder (0.09 g, 53%). (Mass: 430.0266. Calc. mass for $C_{14}H_{17}FN_7S_2Zn$: 430.0262). $^1H$ NMR: δ 2.23 (3H, s, $CH_3$); 2.27 (3H, s, $CH_3$); 2.85 (3H, m, $NHCH_3$); 7.25 (2H, t, J 8.85, ArH); 7.36 (1H, s, $NHCH_3$); 7.66 (2H, m, ArH); 8.10 (1H, s, C(N)H). $^{19}F$ NMR: δ 112.28. MS ES+: m/z 430.07 (100%, Zn[ATSM/A-4-fluorobenzaldehyde]H+).

Example 15R

Zn[ATSM/A-2-pyridinecarboxaldehyde]

As per general procedure (17) except with Zn[ATSM/A] (0.14 g, 0.22 mmol) and 2-pyridinecarboxaldehyde (0.04 mL, 0.43 mmol). The solvent was removed from the reaction mixture with a rotary evaporator. The crude product was redissolved in methanol and precipitated with water. The product was washed with diethyl ether and dried in vacuo.

The product was isolated as a yellow solid (0.16 g, 91%). (Mass: 413.0323. Calc. mass for $C_{13}H_{17}N_8S_2Zn$: 413.0309.) $^1$H NMR: 6 MS ES+: m/z 413.03 (100%, Zn[ATSM/A-2-pyridinecarboxaldehyde]H$^+$); 829.05 (12, $Zn_2$[ATSM/A-2-pyridinecarboxaldehyde]$_2$H$^+$).

Example Section 16

Binuclear Complexes

Example 16A $Zn_2$[ATSM/A-terephthaldehyde-ATSM/A]

General Procedure (18)

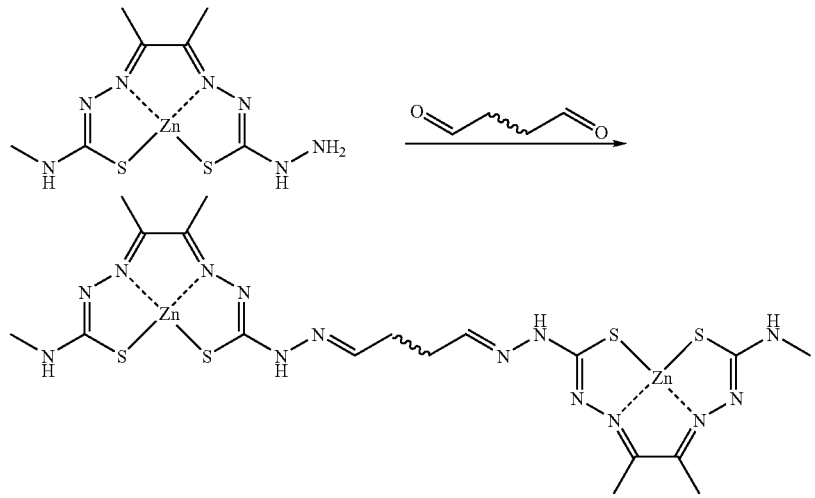

Zn[ATSM/A] (0.18 g, 0.56 mmol) and terephthalaldehyde (0.04 g, 0.28 mmol) were added to methanol (30 mL). The mixture was heated under reflux for 16 h under an atmosphere of nitrogen and allowed to cool slowly to room temperature. An orange powder formed which was washed with methanol and diethyl ether and dried in vacuo. The product was isolated as a yellow/orange solid (0.16 g, 76%). (Found: C, 33.7; H, 4.7; N, 24.4 and C, 34.7; H, 4.8; N, 24.9. Calc. for $C_{22}H_{28}N_{14}S_4Zn_2$: C, 35.4; H, 3.7; N, 24.4.) $R_f$: 33. (Mass: 745.0136. Calc. mass for $C_{22}H_{29}N_{14}S_4Zn$: 745.0165). $^1$H NMR: δ 2.23 (6H, s, CH$_3$); 2.28 (6H, s, CH$_3$); 2.85 (6H, d, J 1.79, NHCH$_3$); 7.37 (2H, bs, NHCH$_3$); 7.64 (4H, s, ArH); 8.11 (2H, s, C(N)H); 11.37 (2H, s, NHNR). MS ES+: m/z 747.01 (60%, $Zn_2$[ATSM/A-terephthalaldehyde-ATSM/A]H$^+$) and (100%, $Zn_2$[ATSM/A-terephthalaldehyde-ATSM/A]H$^+$).

Example 16B $Zn_2$[ATSM/A-glyoxal-ATSM/A]

As per general procedure (18) except with Zn[ATSM/A] (0.19 g, 0.58 mmol) and glyoxal (0.04 mL, 0.29 mmol). The product was isolated as a red/brown solid (0.15 g, 79%). (Found: C, 27.9; H, 4.6; N, 26.5. Calc. for $Zn_2C_{16}H_{24}N_{14}S_4$: C, 28.6; H, 3.6; N, 29.2.) $^1$H NMR: δ 2.22 (6H, s, CH$_3$); 2.25 (6H, s, CH$_3$); 2.85 (6H, s, NHCH$_3$); 7.39 (3H, s, NHCH$_3$); 7.83 (2H, s, C(N)H); 11.45 (2H, s, NHNR). MS ES+: m/z 671.01 (50%, $Zn_2$[ATSM/A-glyoxal-ATSM/A]H$^+$) and 672.97 (90%, $Zn_2$[ATSM/A-glyoxal-ATSM/A]H$^+$).

Crystals suitable for single crystal X-ray crystallography were isolated from the DMSO (the representation below). The complex is located on a crystallographic centre of inversion. The link between the two bis(thiosemicarbazone) units is planar but the best planes of the N and S atoms coordinated to the Zn atom is slightly inclined by 12.5° with respect to this. As in most bis(thiosemicarbazone) complexes the metal is coordinated by an additional ligand in the axial site. The Zn is displaced towards the coordinated DMSO by 0.40 Å from the plane of the coordinated N and S atoms. Both NH groups form hydrogen bonds to oxygen atoms of uncoordinated solvent.

ORTEP representation

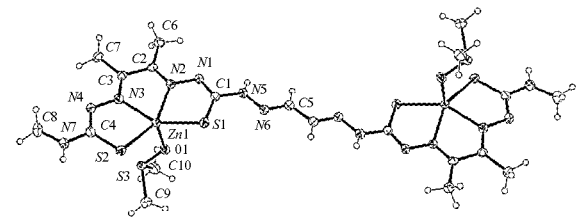

Example 16C $Zn_2$[ATSM/A-isophthalaldehyde-ATSM/A]

As per general procedure (18) except with Zn[ATSM/A] (0.17 g, 0.52 mmol) and isophthalaldehyde (0.03 g, 0.26 mmol). The product was isolated as a bright orange solid (0.13 g, 68%). (Found: C, 34.9; H, 4.0; N, 24.9. Calc. for $C_{22}H_{28}N_{14}S_4Zn_2$: C, 35.3; H, 3.8; N, 26.2.). $^1$H NMR: δ 2.24 (6H, s, CH$_3$); 2.28 (6H, s, CH$_3$); 2.85 (6H, s, NHCH$_3$); 7.36 (2H, m, NHCH$_3$); 7.44 (1H, m, 5-ArH); 7.54 (2H, m, 4-ArH); 8.00 (1H, s, 2-ArH); 8.13 (2H, s, C(N)H); 11.37 (2H, s, NHNR). $^{13}$C NMR: δ 13.86; 14.26; 127.14; 129.08; 135.57; 140.82; 140.86; 148.41. MS ES+: m/z 747.01 (50%, $Zn_2$[ATSM/A-isophthalaldehyde-ATSM/A]H$^+$) and 749.01 (100%, $Zn_2$[ATSM/A-isophthalaldehyde-ATSM/A]H$^+$).

Example 16D

Zn₂[ATSM/A-terephthaloyl-ATSM/A] in ethanol (30 mL) was added slowly whilst stirring. The mixture was stirred for 1 h, a brown precipitate formed immediately on addition of all of the Cu(OAc)₂.H₂O. The product was isolated as a yellow/brown solid (0.51 g, 92%). $R_f$: 23. MS ES+: m/z 322.01 (100%, Cu[ATSM]H⁺).

Example 17B

Cu[ATSM/A]

Zn[ATSM/A] (0.23 g, 0.71 mmol) was dissolved in DMSO (1 mL). A solution of Cu(OAc)₂.H₂O (0.14 g, 0.71 mmol) in

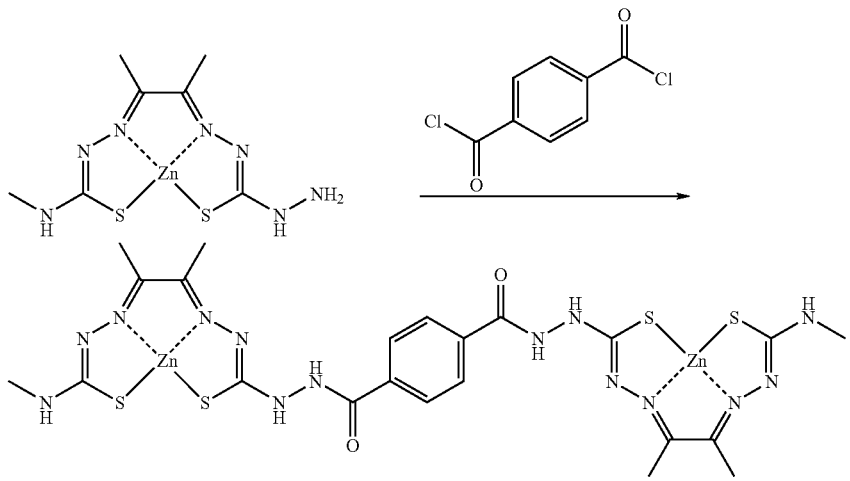

Zn[ATSM/A] (0.21 g, 0.65 mmol) and terephthaloyl dichloride (0.07 g, 0.30 mmol) were added to dichloromethane (20 mL). The mixture was stirred at room temperature for 16 h under an atmosphere of nitrogen. An orange powder formed which was washed with diethyl ether and dried in vacuo. The product was isolated as a orange solid (0.16 g, 64%). ¹H NMR: δ 2.19 (6H, s, CH₃); 2.22 (6H, s, CH₃); 3.02 (6H, s, NHCH₃); 7.53 (2H, s, NHCH₃); 8.03 (4H, s, ArH); 10.27 (2H, s, NH).

Example Section 17

Transmetallation

Example 17A

Cu[ATSM]

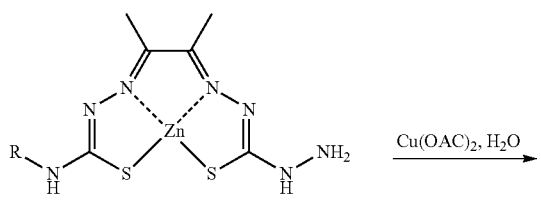

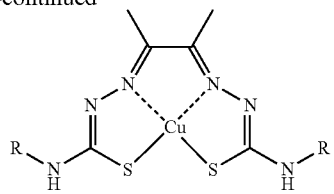

Zn[ATSM] (0.56 g, 1.73 mmol) was dissolved in ethanol (80 mL) and a solution of Cu(OAc)₂.H₂O (0.34 g, 1.73 mmol) methanol (30 mL) was added, and the mixture was stirred for 1 h. The methanol was removed with a rotary evaporator and the remaining solvent was removed under vacuum. A brown precipitate formed on addition of methanol (30 mL), which was filtered and washed with methanol and diethyl ether. The product was isolated as a black solid (0.19 g, 85%). MS ES+: m/z 323.01 (80%, Cu[ATSM/A]H⁺).

Example Section 18

ATS[P-p-carb]₂ and its Derivatives and Complexes

Example 18A

H₂ATS[P-p-carb]₂

4(4-carboxyphenyl)-3-thiosemicarbazide (0.5 g, 2.37 mmol) was dissolved in a minimum volume of DMF (15 mL). Acetic acid (0.6 mL) was added and the solution was heated gently for a few minutes. 2,3-butanedione (0.11 mL, 1.18 mmol) was added and the reaction mixture was heated gently (40° C.) whilst purged with nitrogen for 4 h. Water was added dropwise to the resultant solution and a cream precipitate formed which was collected by filtration, washed with diethyl ether and dried in vacuo to give H₂ATS:[P-p-carb]₂ as a cream powder (0.52 g, 93%) (Found: C, 49.6H, 4.9 N, 17.2. Calc. for C₂₀H₂₀N₆O₄S₂.0.5H₂O C, 49.9; H, 4.4; N, 17.4%). ¹H NMR (DMSO-d⁶): δ 2.32, 6H, s, CH₃; 7.80, 4H, d, J=9.00 Hz, $CH_b$; 7.95, 4H, d, J=8.70 Hz, $CH_c$; 10.18, 2H, s, NHPh; 10.90, 2H, s, NNH; 12.90, H, OH. ¹³C NMR: δ 13.0, CH₃; 125.1, $C_b$; 128.0, $C_a$; 130.2, $C_c$; 143.9, $C_d$; 150.1, C=N, 167.9; C=O; 177.4, C=S. MS: m/z 473=[H₂ATS:[P-p-carb]₂+H⁺]. Crystals suitable for single crystal X-ray crystallography were grown from a DMF/diethyl ether solution.

Example 18B

[Cu(ATS[P-p-carb]$_2$)]

General Procedure (19)

H$_2$ATS:[P-p-carb]$_2$ (0.10 g, 0.21 mmol) and copper acetate (0.052 g, 0.26 mmol) were added to methanol (15 mL). The mixture was heated at reflux for 2 h under an atmosphere of nitrogen and allowed to cool slowly to room temperature. A brown powder formed and was collected by filtration, washed with diethyl ether and dried in vacuo to give [Cu(ATS:[P-p-carb]$_2$)] as a brown powder (0.10 g, 93%). UV-VIS: λ/nm (ε/M-1 cm-1): 273 (26694), 315 (25021), 379 (20178), 486 (10006). MS: m/z 534={[Cu(ATS:[P-p-carb]$_2$)]+H$^+$}.

Example 18C

[Ni(ATS[P-p-carb]$_2$)]

As per general procedure (19) except with H$_2$ATS:[P-p-carb]$_2$ (0.020 g, 0.042 mmol) and nickel acetate (0.012 g, 0.047 mmol) in methanol (2 mL). [Ni(ATS:[P-p-carb]$_2$)] was isolated as a light brown powder (0.019 g, 85%). $^1$H NMR (DMSO-d$^6$): δ 2.08, 6H, s, CH$_3$; 7.68, 4H, broad s, CH$_b$; 7.81, 4H, broad s, CH$_c$; 10.12, H, s, NH; 11.90, broad hump, OH. $^{13}$C NMR: δ 15.6, CH$_3$; 119.9, C$_b$; 125.5, C$_a$; 130.5, C$_c$; 144.2, C$_d$; 161.0, C=N, 167.3, assume C=O (based on H$_2$ATS:[P-p-carb]$_2$); 174.5, assume C=S. MS: m/z 529=[Ni (ATS:[P-p-carb]$_2$)+H$^+$].

Example 18C1

[Ni(ATS[P-p-carb]$_2$) methyl ester]

As per the procedure of Example 4G except with [Ni(ATS:[P-p-carb]$_2$)].

Example 18D

[Zn(ATS[P-p-carb]$_2$)]

As per general procedure (19) except with H$_2$ATS:[P-p-carb]$_2$ (0.10 g, 0.21 mmol) and zinc acetate (0.057 g, 0.26 mmol) in methanol (15 mL). [Zn(ATS:[P-p-carb]$_2$)] was isolated as a bright orange powder (0.11 g, 97%) (Found C, 44.8; H, 3.9; N, 14.4. Calc. for C$_{20}$H$_{18}$N$_6$S$_2$O$_4$Zn.CH$_3$OH C, 44.4; H, 3.9; N, 14.8%). $^1$H NMR (DMSO-d$^6$): δ 2.40, 6H, s, CH$_3$; 7.81, 8H, m, Ar; 9.77, H, s, NH; 12.48, broad hump, OH. $^{13}$C NMR: δ 15.8, CH$_3$; 120.1, C(H); 126.0, broad hump, assume C$_a$ (based on H$_2$ATS:[P-p-carb]$_2$); 130.6, C(H); 145.0, CC; 150.6, C=N, 170.1, assume C=O; 174.0, assume C=S. MS: m/z 527=[Zn(ATS:[P-p-carb]$_2$)—H$^+$].

Example 18D1

[Zn(ATS[P-p-carb]$_2$methyl ester)]

As per the procedure of Example 4G except with [Zn(ATS:[P-p-carb]$_2$].

Example 18E

H$_2$ATS[P-p-carb]$_2$-ocreotide

The protected peptide corresponding to the sequence of Ocreotide (H-D-Phe-Cys-Phe-D-Trp-Lys-Thr-Cys-Thr-ol) was assembled on an ABI 433A synthesiser using Fmoc-Thr (Bu$^t$)-ol 2-Chlorotrityl resin (0.1 mmol) and ten equivalents of acyl component per cycle. A final Fmoc removal cycle was incorporated and the resin gave a strongly positive Kaiser ninhydrin test.

A portion of the resin (approx 0.05 mmol) was transferred to a manual nitrogen bubbler apparatus and a solution of H$_2$ATS:[P-p-carb]$_2$ (0.037 g, 0.078 mmol) and HOBt (0.038 g, 0.25 mmol) in DMF (1.5 mL) was added. The resin was agitated by nitrogen bubbling and DIC (50 uL, 0.32 mmol) added. After 3 h, a resin sample gave a negative Kaiser test indicating that the reaction had gone to completion. The resin was drained and washed with DMF (5×10 mL), DCM (3×10 mL) and DMF (3×10 mL). After a final wash with diethyl ether (1×10 mL), the resin was transferred to a flask and dried under reduced pressure. To this was added an ice-cold solution of phenol (0.75 g) in water (0.5 mL) and TFA (10 mL). After 0.5 h at ice-temperature the reaction mixture was agitated gently for 2.5 h at room temperature. The resin was removed by filtration and washed with several portions of fresh TFA (~10 mL total) and then dry toluene (~15 mL total). The combined filtrate and washings were evaporated under reduced pressure to give a yellow oil which solidified on trituration with dry diethyl ether to give a yellow solid.

Formation of disulfide bridge: A portion of the crude product was dissolved in water (10 ml, approx. 1 mg ml$^{-1}$) and the pH adjusted to ~8.5 with aqueous ammonia. This was then stirred vigorously open to air for two days. The solution was acidified with glacial acetic acid and then freeze dried to remove the ammonium acetate. The product was purified by preparative RP HPLC using the following gradient (minutes, % B): 0, 5; 10, 5; 20, 30; 80, 60; 90, 100. (A=0.1% TFA, B=90% acetonitrile/10% water/0.1% TFA, flow rate=10 mL min$^{-1}$, detection 214 nm). One major peak was eluted at 92 min with a shoulder at 94 min. The first fraction was freeze dried to give the product as a yellow residue. Analytical HPLC R$_t$=53 min. MS: m/z 1723 and 1480.

Example 18F

[Cu(ATS[P-p-carb]$_2$-ocreotide)]

A very small volume of H$_2$ATS:[P-p-carb]$_2$-ocreotide (2 drops), produced as described in Example 18E, was diluted with DMF (0.5 mL) and copper acetate (0.002 g, 0.010 mmol) and some acetonitrile (5 drops) were added. The mixture was stirred overnight and the solvent was removed under reduced pressure. The resultant green residue was washed with ethanol (~3 mL) to give the product as a brown residue. Analytical HPLC R$_t$=52 min.

Example Section 19

PGTS(Et) and Complexes Thereof

Example 19A

PGTS(Et)

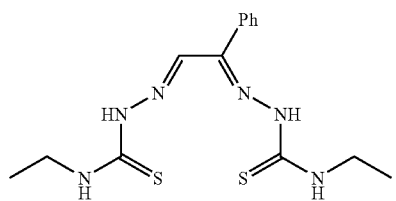

Phenylglyoxal (0.2 g, 1.3 mmol) and ethylthiosemicarbazide (0.3 g, 2.6 mmol) were dissolved in methanol (10 ml), acetic acid (0.14 ml, 2.6 mmol) was added and the solution was heated to reflux and stirred for 4 hours. The resulting solution was allowed to stand overnight. The solution underwent gravity filtration to give an yellow crystalline solid was isolated (0.24 g, 76%). The full characterisation of the product by $^1$H and $^{13}$C NMR, and ES$^+$-MS was consistent with reported values. NMR: $\delta_H$ (d$_6$-DMSO) 11.82 (2H, br s, NH), 8.36 (1 H, s, C(N)H), 8.00 (2H, d, S=8.5, ArH), 7.70-7.23 (5H, m, ArH+NH), 3.90 (4H, q, CH$_2$CH$_3$) and 0.85 (6H, t, CH$_2$CH$_3$).

Example 19B

Zn [PGTS(Et)]

As per general procedure (5) described in Example 5A above, but using PGTS(Et) (0.20 g, 0.8 mmol), MeOH (20 ml) and zinc acetate (0.17 g, 0.8 mmol). Zn[PGTS(Et)] was isolated as an orange crystalline solid (0.12 g, 50%). NMR: $\delta_H$ (DMSO) 8.36 (2H, d J=7.31, ArH), 7.85 (1H, s, CH=N), 7.58 (1H, t J=7.32, ArH), 7.47 (2H, t J=7.32, ArH), 3.42 (4H, q q J=6.4, CH$_2$CH$_3$) and 1.04 (6H, t J=6.4, CH$_2$CH$_3$). Suitable crystals for X-ray analysis were obtained, and the analysis showed that the phenyl ring of the imine backbone lies in the plane of the ligand despite the allylic strain between the hydrogen atom attached to the carbon atom a to the carbon atom to which the phenyl group is attached, and the nearby hydrogen atom attached in the ortho position in the phenyl group. Also, an apical methanol group is present as a fifth coordinating group.

Example 20

X-Ray Crystallography

Crystals were mounted on a glass fibre using perfluoropolyether oil and cooled rapidly to 150 K in a stream of cold N$_2$ using an Oxford Cryosystems CRYOSTREAM unit. Diffraction data were measured using an Enraf-Nonius KappaCCD diffractometer (graphite-monochromated MoKα radiation, λ=0.71073 Å). Intensity data were processed using the DENZO-SMN package. The structures were solved using the direct-methods program SIR92, which located all non-hydrogen atoms. Subsequent full-matrix least-squares refinement was carried out using the CRYSTALS program suite.

H$_2$ATS:[P-p-carb]$_2$

The structure was solved in the space group P 1 using the direct-methods program SIR92, which located all non-hydrogen atoms. Coordinates and anisotropic thermal parameters of all ordered non-hydrogen atoms were refined. A molecule of ether was modelled as disordered over two positions related by a crystallographic inversion. The coordinates and isotropic thermal parameters of its non-hydrogen atoms were refined subject to restraint of the C—O bond lengths to 1.44 (2) Å, the C—C bond lengths to 1.48(2) Å and C—O—C and O—C—C angles to 112(2)°. The OH and NH hydrogen atoms were located in a difference Fourier map and their coordinates and isotropic thermal parameters subsequently refined. Other hydrogen atoms were positioned geometrically after each cycle of refinement. A 3-term Chebychev polynomial weighting scheme was applied. Refinement converged satisfactorily to give R=0.0603, wR=0.0777.

[Ni(ATS{Me}/P-p-carb)]

Examination of the systematic absences of the intensity data showed the space group to be either C c or C$_2$/c. The structure was solved in the space group C$_2$/c using the direct-methods program SIR92, which located all non-hydrogen atoms of the Ni complex. Coordinates and anisotropic thermal parameters of all non-hydrogen atoms were refined. A difference Fourier map showed a number of peaks of additional electron density, which were identified as two distinct molecules of dimethylformamide. One of these was located on a site with no crystallographic symmetry, but the second occupied a site located on a crystallographic twofold axis. Geometric restraints were applied to this molecule: the O—C distance was restrined to 1.25(2) Å, the C(carbonyl)-N distance to 1.35(2) Å and the N—C(methyl) distances to 1.45(2) Å. Similarity restraints were applied to the thermal parameters of directly-bonded pairs of atoms. The NH and OH hydrogen atoms were located in a difference Fourier map and their coordinates and isotropic thermal parameters subsequently refined. Other hydrogen atoms were positioned geometrically after each cycle of refinement. A 3-term Chebychev polynomial weighting scheme was applied. Refinement converged satisfactorily to give R=0.0320, wR=0.0358. An attempt was made to solve and refine the structure in the space group C c, in which the twofold axis associated with the disorder is absent. The structure could readily be solved by direct methods but the disorder was still clearly apparent and the refinement failed to converge. It was therefore assumed that the initial choice of space group was correct.

Example Section 21

Fluorescence

UV/Vis and fluorescence spectra were measured with a Perkin Elmer Lamda 19 spectrometer and a Hitachi F-4500 fluorescence spectrophotometer respectively.

Fluorescence microscope images were obtained using a Nikon TE-2000E microscope with an Andor iXon iCCD camera. Irradiation was carried out with filtered radiation from a mercury lamp at ca. 480 nm.

The co-ordination of BTSCs to zinc produces an extended delocalised system. Zn[ATSM] was the first of these complexes observed to be fluorescent (Emission: $\lambda_{max}$=557 nm) and with UV/Vis absorptions at 308 and 429 nm, in line with the predictions of DFT calculations. A third absorption predicted by DFT at below 300 nm was not observed due to limitations of the spectrometer.

Example 21A

Zn [ATS(R)/P-carb] (see Example Sections 4 and 5 Above)

In addition to the fluorescence band around 550 nm the Zn[ATS(R)/P-carb] complexes show a second band with at $\lambda_{ma}$ 340 nm. This may be associated with the fluorescence of the terminal benzoic acid group. Zn [ATS(Ph)/P-Carb] was observed to have the most intense emission at the wavelength due to the additional phenyl as shown in FIG. 1.

Fluorescence emission of Zn[ATS(R)/P-Cart] for excitation with DMSO at 300 nm.

Example 21B(i)

Figure 2:
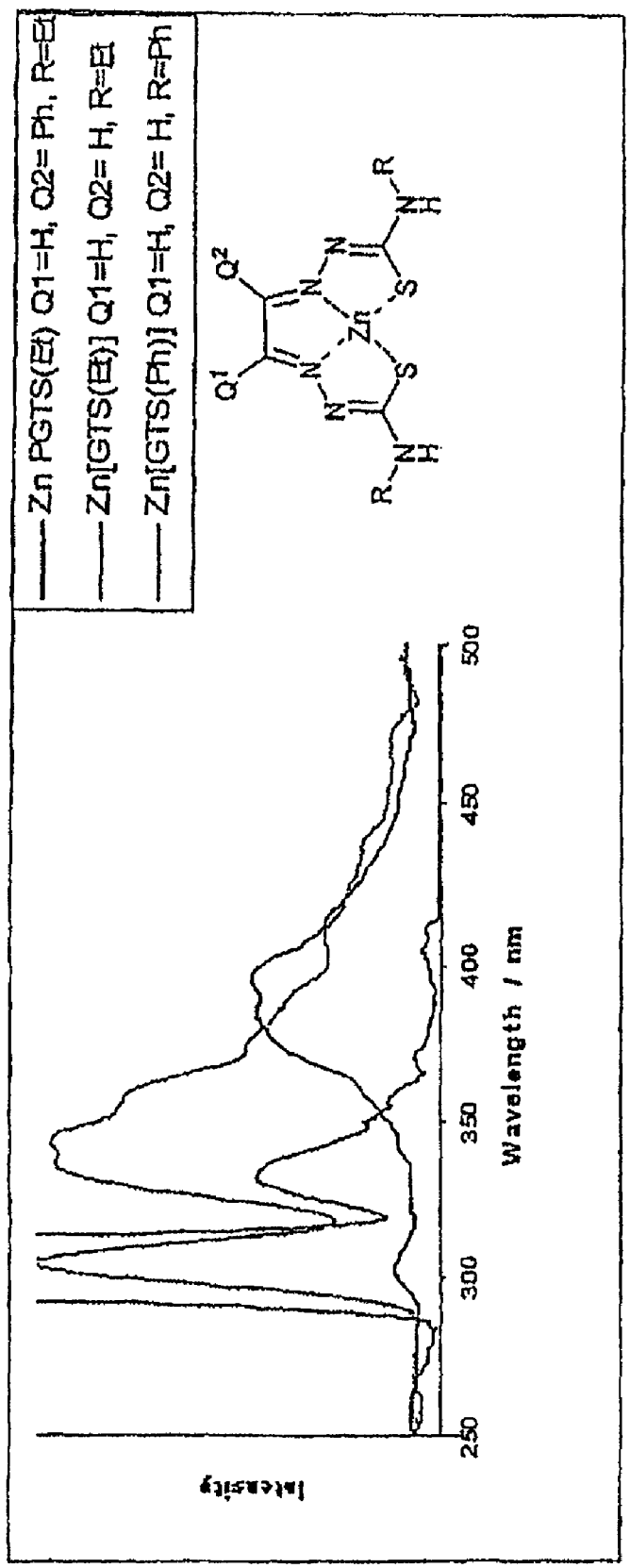
FIG. 2 shows the fluorescence emission and the compound of Example 21B(i)

Fluorescence of Zn bis(thiosemicarbazones) (Zn[BTSCs]) Containing Ph group versus Zn [BTSCs1 without Ph Group To further investigate the effect of addition of a phenyl group onto zinc [BTSC], complexes differing only by the presence of a phenyl group were compared; see FIG. 2.

Fluorescence of Zn PGTS(Et), Zn GTS(Et) and Zn GTS (Ph)

The Zn[GT(Et)] peak at 335 nm, is a Raman scattering peak. The Zn[PGTS(Et)] peak at 342 nm and the Zn[GTS (Ph)] peak at 397 nm are due to fluorescence associated with the phenyl ring. These peaks are readily differentiated; true fluorescence emission peaks ($\lambda_{max}$,) remain static over a range of excitation wavelengths whereas Raman peaks ($\lambda_{max}$) vary, as described by Wayne, R. P., in *Principles and Applications of Photochemistry*, 1986.

Example 21B(ii)

Comparison of Fluorescence Emission and UV/Vis Absorption of Zn[BTSCs]

The following table gives the position of $\lambda_{max}$ for the fluorescence emission spectra and the second and third UV/vis Absorptions for a range of Zn[BTSCs]

|  | Fluorescence Emission | | UV/Vis Absorption | |
| --- | --- | --- | --- | --- |
|  | $\lambda_{max(1)}$ | $\lambda_{max(2)}$ | $\lambda_{max(2)}$ | $\lambda_{max(3)}$ |
| Zn[ATS(H)/P-Carb] (Ex. 5D) | 343 | 554 | 355 | 453 |
| Zn[ATS(Me)/P-Carb] (Ex. 5B) | 339 | 555 | 318 | 443 |
| Zn[ATS(Et)/P-Carb] (Ex. 5C) | 339 | 552 | 319 | 445 |
| Zn[ATS(Ph)/P-Carb] (Ex. 5E) | 341 | 564 | 341 | 444 |
| Zn PGTS(Et) (Ex. 19B) | 391 | 567 | 331 | 466 |
| Zn[GTS(Et)] (Ex. 8F) | — | 550 | 323 | 445 |
| Zn[GTS(Me)] (Ex. 8E) | — | 550 | 334 | 446 |
| Zn[GTS(Ph)] (Ex. 8G) | 340 | 575 | 342 | 469 |

The complexes containing a phenyl ring were observed to have two fluorescence emission bands. Fluorescence peak (1) between 340 and 400 nm, associated with the phenyl component and a second, fluorescence peak (2), present in all complexes between 530 and 570 nm, associated with the BTSC backbone. The intensity of fluorescence peak (1) was always less than that of fluorescence peak (2). Fluorescence peak (2) for the all the phenyl complexes appear at longer wavelengths as these have longer delocalised $\pi$ systems than their alkyl substituted counterparts.

Example 21B(iii)

Fluorescence of Zn[ATS(Me)/A-T-Amino-BTAP](Ex. 7D)

The fluorescence emission spectrum of Zn[ATS(Me)/A-T-Amino-BTAP] can be examined as two regions 400-500 nm, predominantly benzothiazole fluorescence and 490-790 nm, predominantly the zinc (BTSC) fluorescence.

Figure 3:
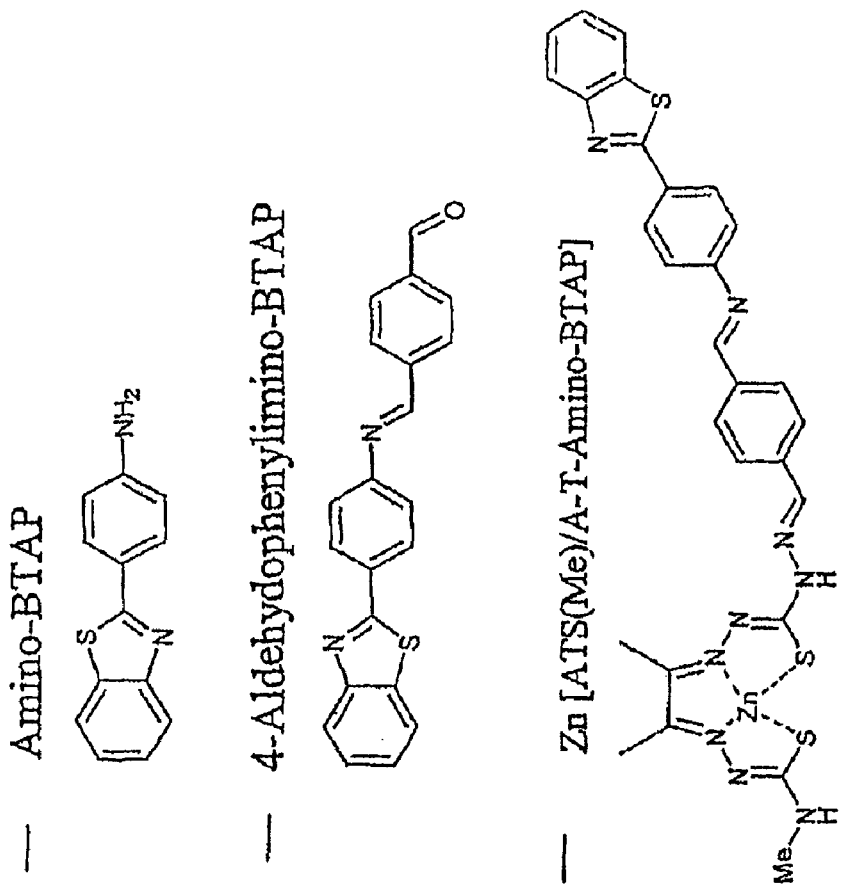
FIG. 3 shows the fluorescence emission and the compound of Example 21B(iii)(a)
Figure 3:
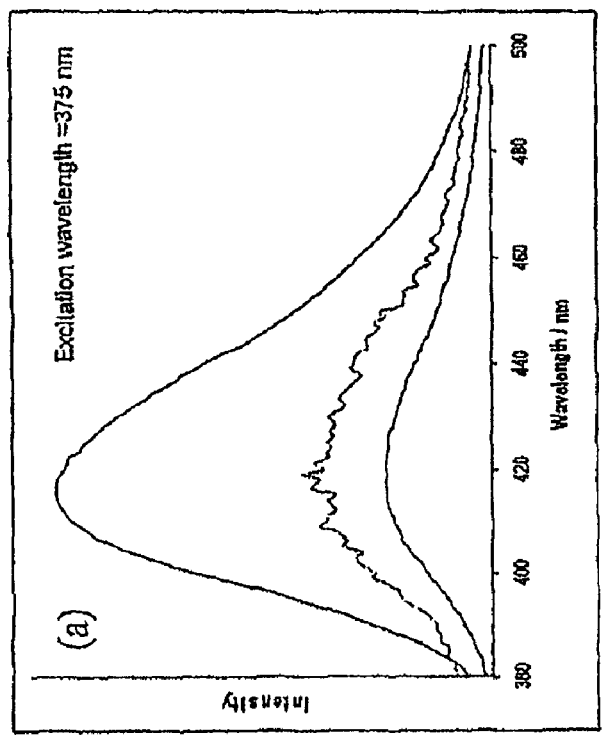
Figure 4:
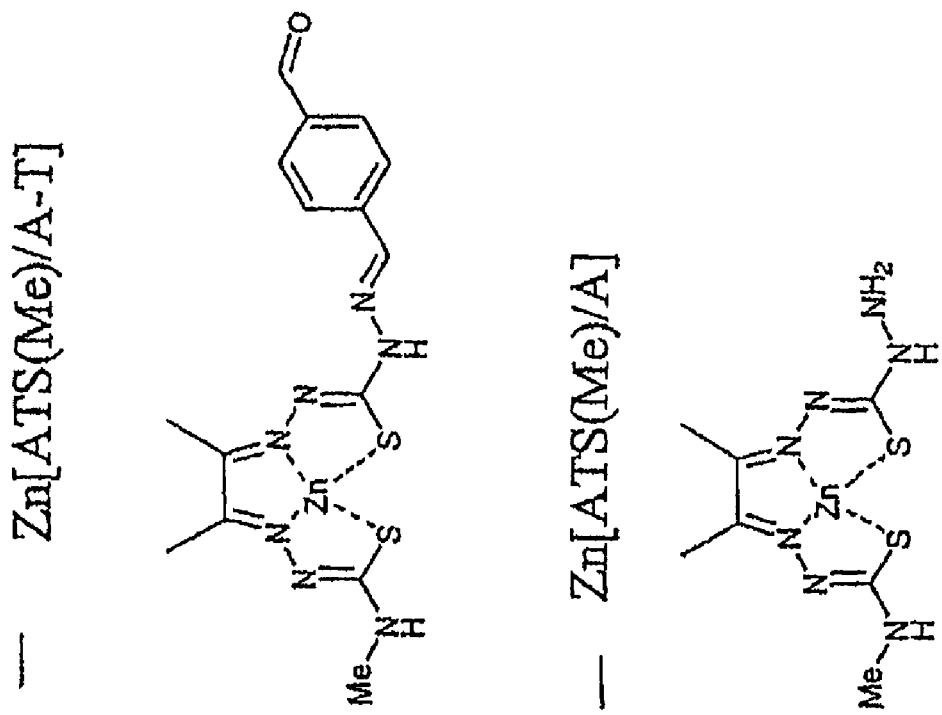
FIG. 4 shows the fluorescence emission and the compound of Example 21B(iii)(b)
Figure 4:
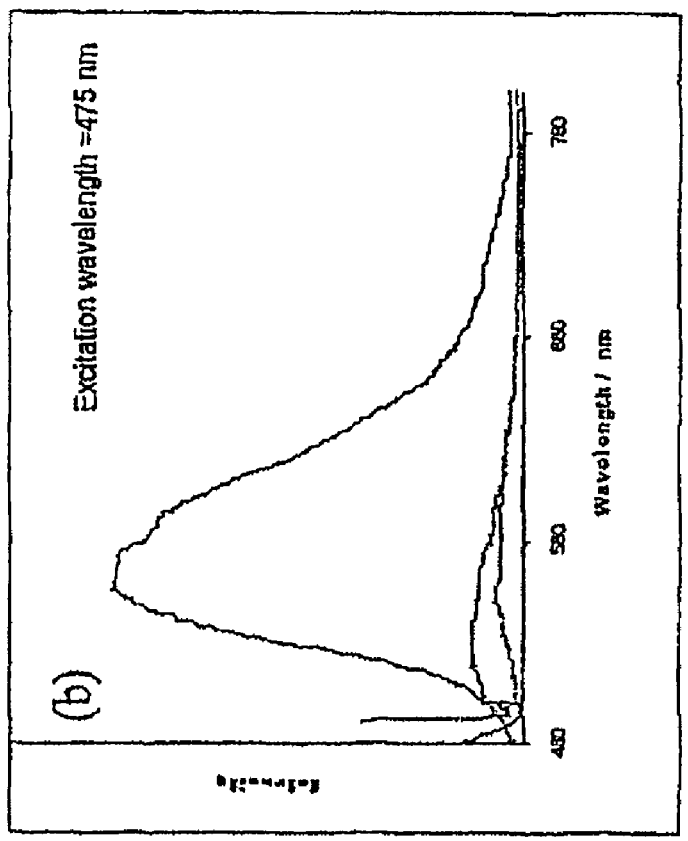

FIGS. 3 and 4 show the fluorescence emission spectra (a) for Amino-BTAP, 4-Aldehydrophenylimino-BTAP and Zn[ATS(Me)/A-T-Amino-BTAP], (375 nm, D MSO, 0.01 mM); and (b) for Zn[ATS(Me)/A-T-Amino-BTAP], Zn[ATS (Me)/A] and Zn[ATS(Me)/A-T], (475 nm. DMSO, 0.01 mM). For the avoidance of doubt, in (b) the curve of highest intensity is for Zn[ATS(e)/A-T-Amino-BTAP], the curve of second highest intensity is for Zn[ATS(Me)/A] and the curve of lowest intensity is for Zn[ATS(Me)/A-T].

In the region of benzothiazole fluorescence the intensity is observed to reduce threefold upon formation of 4-Aldehydrophenylimino-BTAP, however, the intensities of this and Zn ATS(Me)/A-T-Amino-BTAP are comparable. In the zinc complex region the precursor zinc complexes, Zn[ATS(Me)/A] and Zn[ATS(Me)/A-T] are approximately tenfold lower than that observed for the linked molecule Zn[ATS(Me)/A-T-Amino-BTAP]. Upon absorption of 375 nm radiation by the benzothiazole portion of the conjugate it was suggested (Ha, T., *Single Molecule*, 2001, 2, 283-4) that Fluorescence Resonance Energy Transfer, FRET, however, upon excitation at 375 nm, little enhancement of the 561 nm, zinc complex peak, is observed; FRET is blocked by the phenyl linker group.

Example 21C

Further Fluorescence and UV/Vis Data

The optical properties of a range of mono- and binuclear complexes derived from Zn[ATSM/A] (see the table below) were measured by electronic absorption (UV/vis) and fluorescence spectroscopy.

1 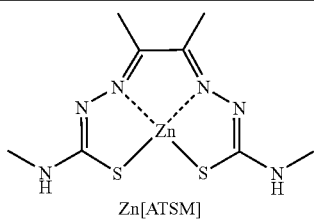
Zn[ATSM]
2 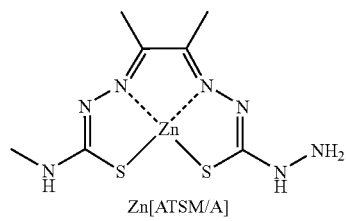
Zn[ATSM/A]
3 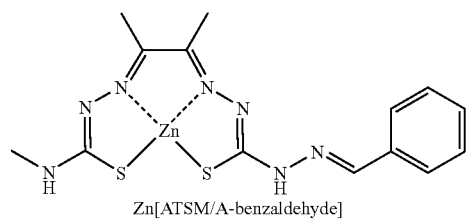
Zn[ATSM/A-benzaldehyde]
4 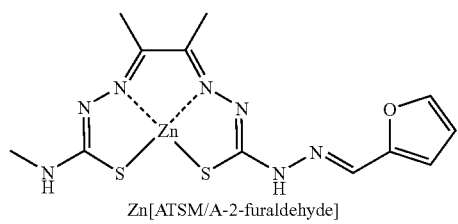
Zn[ATSM/A-2-furaldehyde]
5 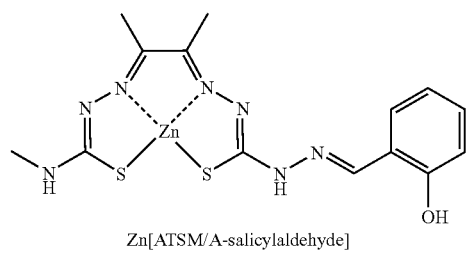
Zn[ATSM/A-salicylaldehyde]
6 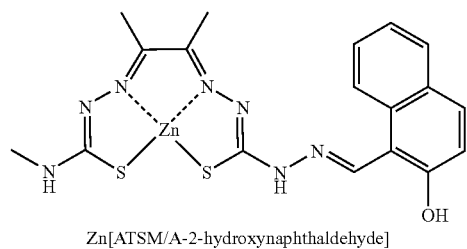
Zn[ATSM/A-2-hydroxynaphthaldehyde]
7 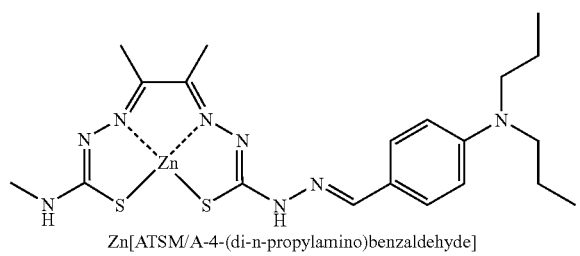
Zn[ATSM/A-4-(di-n-propylamino)benzaldehyde]

-continued
8
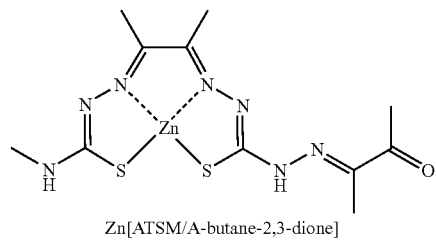
Zn[ATSM/A-butane-2,3-dione]
9
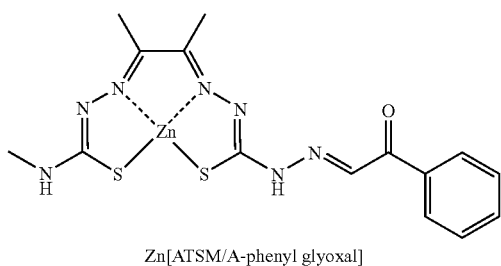
Zn[ATSM/A-phenyl glyoxal]
10
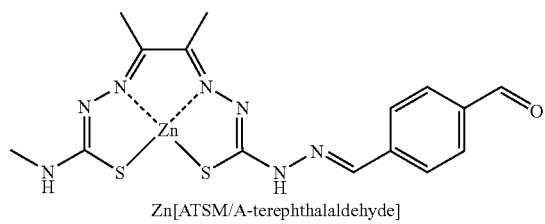
Zn[ATSM/A-terephthalaldehyde]
11
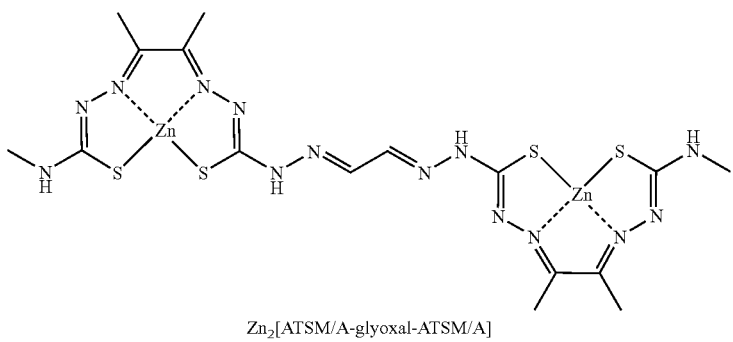
$Zn_2$[ATSM/A-glyoxal-ATSM/A]
12
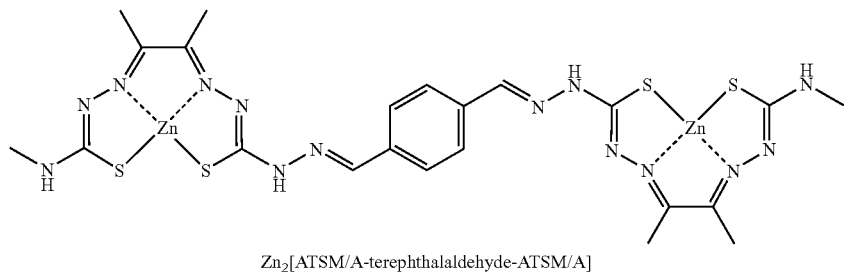
$Zn_2$[ATSM/A-terephthalaldehyde-ATSM/A]
13
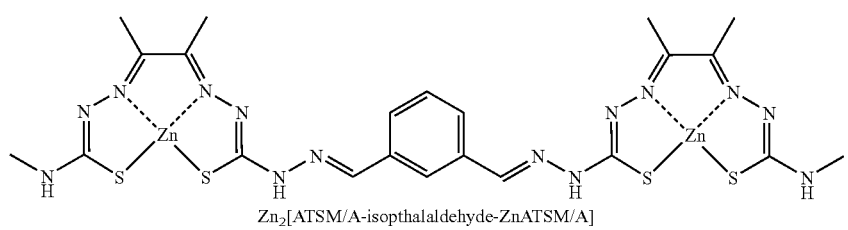
$Zn_2$[ATSM/A-isopthalaldehyde-ZnATSM/A]

UV/vis spectroscopy: electronic absorption spectra were recorded in DMSO at 0.1, 0.01 and 0.001 mmol concentrations. Values of $\lambda_{max}$ for wavelengths greater than 300 nm are given in Table 4.2. Values of $\lambda_{max}$ were obtained from spectra of solutions at 0.001 mmol concentration, as this is sufficiently dilute to enable intermolecular interactions to be neglected. Molar absorption coefficients, $\epsilon$, for the higher wavelength absorption peak were calculated using the Beer-Lambert law (see Atkins, P. W. *Physical Chemistry*; Oxford University Press, 1998).

UV/vis data for complexes 1-13 is given in the following table:

| | $\lambda_{max}$ (nm) | | | $\epsilon$ (mol$^{-1}$ dm$^3$ cm$^{-1}$) |
|---|---|---|---|---|
| 1 | 308 | | 429 | 29444 |
| 2 | 315 | | 429 | 29690 |
| 3 | 333 | | 451 | 40016 |
| 4 | 340 | | 455 | 36939 |
| 5 | 346 | | 455 | 51172 |
| 6 | 334 | 379 | 460 | 62183 |
| 7 | 321 | 370 | 465 | 75127 |
| 8 | 323 | | 455 | 35594 |
| 9 | 341 | | 474 | 46157 |
| 10 | | 364 | 468 | 49912 |
| 11 | 330 | | 489 | 126450 |
| 12 | 329 | 376 | 477 | 95192 |
| 13 | 339 | | 457 | 79475 |

The structure of Zn[ATSM] 1 has been optimised using B3LYP/6-31 G in the Gaussian suite of ab initio calculation programs (Jensen, K. A.; Rancke-MAdson, E. Z. *Anorg. Allg. Chem.* 1934, 219, 243). The molecular orbitals have been calculated, and using both semiempirical ZINDO calculation and time-dependent DFT, the UV/vis spectrum has been predicted from a calculation of the first eight excited states. These are compared with the following experimental UV/vis spectrum of 1.

Figure 5:
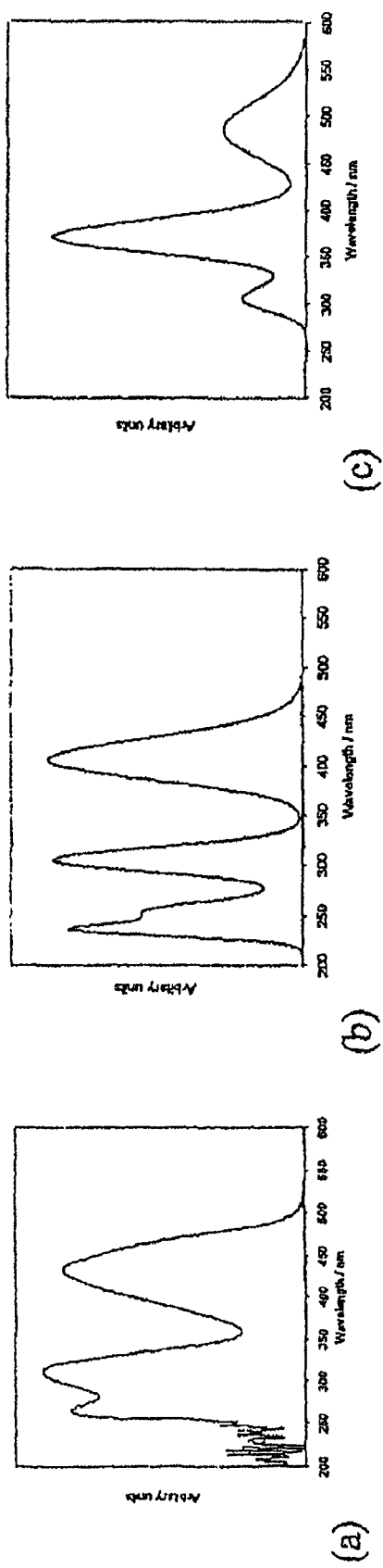
FIG. 5 shows calculated and experimental UV/vis spectra of ZnATSM: (a) experimental spectrum in DMSO, (b) calculated spectrum using the semiempirical ZINDO method, and (c) calculated spectrum using the ab initio TD-DFT method, (b) calculated spectrum using the ZINDO method and (c) calculated using the TD-DPT method.

Calculated and experimental UV/vis spectra of ZnATSM 1 as shown in FIG. 5(a) Experimental spectrum in DMSO, (b) calculated spectrum using the semiempirical ZINDO method, (c) calculated spectrum using the ab initio TD-DFT method as shown in FIGS. 5(a), 5(b) and 5(c).

The spectra are sufficiently similar to suggest that enough of the excited states have been sampled to include the major transitions that contribute to the observed spectrum. Therefore the MO analysis of the ground state structure may give some insight into the nature of the transitions involved. It has been shown that as expected the lowest energy transition is from the HOMO to the LUMO. The spatial distributions of the electron density of the orbitals show that this corresponds to a $\pi \rightarrow \pi$ transition. This effectively shifts electron density in the $\pi$ system from the imine bonds and the sulphur lone pairs to the C—C backbone. The UV/vis spectrum of Zn[ATSM/A] suggests this complex is structurally very similar to Zn[ATSM]. The lowest energy transition observed experimentally occurs at an identical wavelength in both 1 and 2, which is consistent with the observation that for Zn[ATSM] there is no contribution from the orbitals of the N(4) substituents to either the HOMO or LUMO.

All of the complexes formed by condensation of an aldehyde with the pendant amino group of Zn[ATSM/A] 3-13, show an increase in the wavelength of the lowest energy transition, which appears to correlate with an increase in molar absorption coefficient. The wavelength shift suggests that conjugation via the imine results in a decrease in the HOMO to LUMO energy gap. The gross selection rule for an electronic transition states that there must be a change in dipole moment on transition.[52] The intensity of absorption is proportional to the square of the magnitude of the transition dipole moment, and so a strong absorption is indicative of the electron density moving a large distance upon excitation, consistent with sulphur lone pairs moving to the C—C backbone.

The variation in molar absorption coefficient for the mononuclear complexes derived from 2 can loosely be related to their structural differences. In general absorption is stronger for those complexes in which the imine is formed from a benzaldehyde derivative than for the complexes which are not directly conjugated to a phenyl ring, for example, the complex 4 has a larger molar absorption coefficient than complex 8, formed by the addition of butane-2,3-dione to 2. Additional conjugation introduced by the naphthyl system accounts for the greater absorption of 6 (62183 mol$^{-1}$ dm$^3$ cm$^{-1}$) than 5 (51172 mol$^{-1}$ dm$^3$ cm$^{-1}$). The nature of substituents on the phenyl ring also seems to play a role. An electron donating substituents in the para position dramatically increases absorption, shown for example, by the relative intensity of absorption of complex 7 (75127 mol$^{-1}$ dm$^3$ cm$^{-1}$) compared to complex 10 (49912 mol$^{-1}$ dm$^3$ cm$^{-1}$), which has an electron withdrawing group in the para position.

Fluorescence spectroscopy: the fluorescence of complexes 1-13 was measured at 0.1, 0.01 and 0.001 mmol concentrations by exciting at a range of wavelengths from 300 nm to 500 n. At 0.1 mmol and 0.01 mmol concentrations all of the complexes show emissions between 534 nm and 604 nm. The maximum intensity for these bands is generally observed by exciting between 450 nm and 500 nm, suggesting correlation between the lower energy absorption in the UV/vis spectrum and the fluorescence emission. Values of $\lambda_{max}$ and the intensity of the fluorescence emission relative to that of complex 3 when excited at 475 nm for complexes 1-13 are give in the following table.

| | $\lambda_{max}$/nm | Relative intensity |
|---|---|---|
| 1 | 534 | 0.09(0.35)[a] |
| 2 | 548 | 0.10(0.32)[a] |
| 3 | 553 | 1.00 |
| 4 | 551 | 1.05 |
| 5 | 548 | 0.95 |
| 6 | 558 | 2.61 |
| 7 | 578 | 2.85 |
| 8 | 561 | 0.33 |
| 9 | 605 | 0.19 |
| 10 | 584 | 0.23 |
| 11 | 558 | 2.46 |
| 12 | 575 | 3.31 |
| 13 | 567 | 2.65 |

All values relate to 0.01 mmol solutions in DMSO.
(a) The values in parentheses refer to 0.1 mmol solutions.

Zn[ATSM] and Zn[ATSM/A] show comparatively weak fluorescence at 0.01 mmol concentrations in DMSO. It is possible that the potential fluorescence of 2 is quenched by the lone pair on the nitrogen of the pendant amine group. Conjugation of benzaldehyde to Zn[ATSM/A] gives a tenfold increase in the intensity of the fluorescence relative to Zn[ATSM] for excitation at 475 nm. The fluorescence emission of the binuclear zinc complexes 11, 12 and 13 show an almost thirty-fold increase in fluorescence intensity relative to Zn[ATSM] and Zn[ATSM/A]. This is particularly relevant to potential applications of these complexes in fluorescence imaging, as it suggests that a much lower concentration of a

The invention claimed is:

1. A metal complex of formula (III):

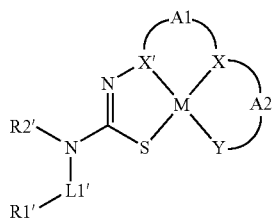

(III)

wherein:
M is a Cu;
A1 is:

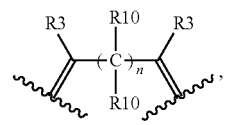 (a')

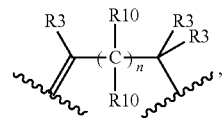 (b')

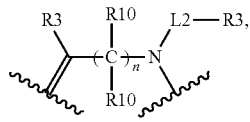 (c')

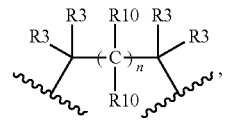 (d')

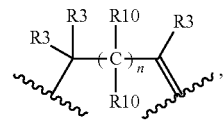 (e')

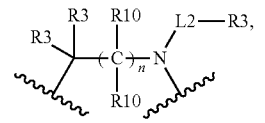 (f')

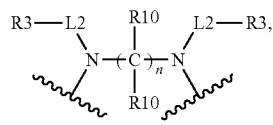 (g')

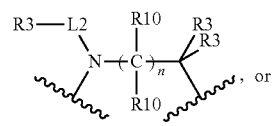 (h')

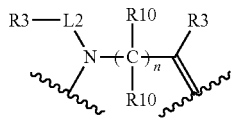 (i')

n is 0 or an integer of 1 to 5;
A2, X and Y are as defined in (i), (ii) and (iii) which follow:
(i) A2 is

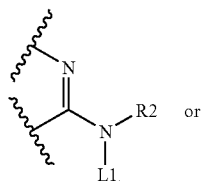 (d)

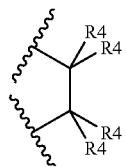 (e)

X is N or P and A1 is attached to X via a double bond, or X is O, S, N(R5) or P(R5) and A1 is attached to X via a single bond; and Y is N, O, P, S, N(R5), O(R5), P(R5) or S(R5); or (ii) X is N or P and A1 is attached to X via a double bond, or X is O, S, N(R5) or P(R5) and A1 is attached to X via a single bond; and Y and A2 together represent a moiety of formula (B):

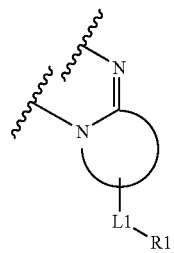 (B)

wherein the ring that is substituted by L1-R1 is a 5- to 11-membered heterocyclic group; or (iii) X, A2 and Y together represent

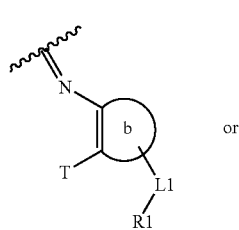 (f)

-continued

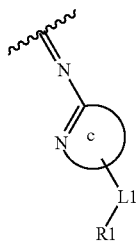

(g)

wherein T is OH, O—, COOH or C(O)O— and rings b and c are aromatic C$_{6-10}$ carbocyclic or 5 to 11 membered aromatic heterocyclic groups;

X' is N and A1 is attached to X' via a double bond, or X' is N(R5), O, S or P(R5) and A1 is attached to X' via a single bond;

L1 and L1', which are the same or different, are each independently selected from a covalent bond and a linker group selected from —C(O)—, -alk—C(O)—, —C(O)O—, -alk—C(O)O—, —OC(O)—, -alk—OC(O)—, —O—, -alk—O—, —N(R7)—, -alk—N(R7)—, —N(R7)C(O), -alk—N(R7)C(O)—, —C(O)N(R7), -alk—C(O)N(R7), —C(S)—, -alk—C(S)—, —S—, -alk—S—, —C(S)N(R7)—, -alk—C(S)N(R7)—, —N(R7)C(S)—, -alk—N(R7)C(S)—, —S(O)$_2$N(R7)—, -alk—S(O)$_2$N(R7)—, —N(R7)S(O)$_2$—, -alk—N(R7)S(O)$_2$—, —S(O)—, -alk—S(O)—, —N(R7)C(O)O—, -alk—N(R7)C(O)O—, —OC(O)N(R7)—, -alk—OC(O)N(R7)—, —N(R7)C(O)N(R7)—, -alk—N(R7)C(O)N(R7)—, —N(R7)C(S)N(R7)—, -alk—N(R7)C(S)N(R7)—, —N═C(R7)—, -alk—N═C(R7)—, —C(R7)═N— and -alk—C(R7)═N—;

R1 and R1', which are the same or different, are each independently selected from hydrogen, Z, L3—Z, L3-alk—Z, —V—L3—Z, —V—L3-alk—Z, alk—V—L3—Z, -alk—V—L3-alk—Z and a substituted or unsubstituted group selected from an alkyl, amino, carbocyclic, cycloalkyl, heterocyclic, -alk-carbocyclic, -alk-cycloalkyl and -alk-heterocyclic group, which group may be further substituted by L3—Z or L3-alk—Z, wherein L3 is as defined above for L1 and L1', —V— is a linking group of the following formula:

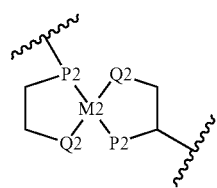

wherein P2 and Q2 are independently selected from N, O, P and S and M2 is a metal atom, and Z is a moiety selected from a biologically active molecule, a fluorophore, a cytotoxin, an amino acid, a peptide, an oligopeptide, a polypeptide, a sugar, a group containing a label, a leaving group which is replaceable by a group containing a label, and a complex of Cu, Zn or Ni with a bis(thiosemicarbazone) or a thiosemicarbazone;

-alk- is an alkylene, alkenylene or alkynylene group based on an alkyl, alkenyl or alkynyl group;

R2 and R2', which are the same or different, are each independently selected from H, C$_1$-C$_6$ alkyl and C$_1$-C$_6$ alkoxy;

each R3 is independently selected from H, C$_1$-C$_6$ alkyl, heterocyclic group and phenyl;

each R4 is independently selected from H, C$_1$-C$_6$ alkyl, heterocyclic group and phenyl;

each R5 is independently selected from H, C$_1$-C$_6$ alkyl and a group comprising an electron donor group, which donor group is separated by two carbon atoms from the O, N, S or P atom to which R5 is attached;

R7 is H, alkyl or cycloalkyl;

each R10 is independently selected from H, C$_1$-C$_6$ alkyl, heterocyclic group and phenyl;

and L2 is —C(O)— or a covalent bond;

with the proviso that when X and X' are both N, Y is S, A1 is (a') and A2 is (d) then either the moiety represented by L1-R1 or the moiety represented by L1'-R1' is other than H, unsubstituted alkyl or unsubstituted alkoxy.

2. A metal complex according to claim 1 with the proviso that when X and X' both N, Y is S, A1 is (a') and A2 is (d) then either R1 or is Z, L3—Z, L3-alk—Z, —V—L3—Z, —V—L3-alk—Z, -alk—V—L3—Z, -alk—V—L3-alk—Z or a group selected from an alkyl, amino, carbocyclic, cycloalkyl, heterocyclic, -alk-carbocyclic—, alk-cycloalkyl and -alk-heterocyclic group, which group is further substituted by L3—Z or L3-alk—Z.

3. A metal complex according to claim 1 wherein either:
A2, X and Y are as defined in (ii) or (iii);
A2, X and Y are as defined in (i) wherein A2 is (e); or
either R1 or R1' is Z, L3—Z, L3-alk—Z, —V—L3—Z, —V—L3-alk—Z, -alk—V—L3—Z, -alk—V—L3-alk—Z or a group selected from an alkyl, amino, carbocyclic, cycloalkyl, heterocyclic, -alk-carbocyclic, -alk-cycloalkyl and -alk-heterocyclic group, which group is further substituted by L3—Z or L3-alk—Z.

4. A metal complex according to claim 1 wherein A1 is (a'), (b'), (d') or (e') and n is 2.

5. A metal complex according to claim 1 wherein A1 is (d').

6. A metal complex according to claim 1 wherein n=0.

7. A complex according to claim 1, wherein:
M is Cu;
L1' is a covalent bond;
R1' is H or a group selected from alkyl, alkoxy and phenyl; and
A2 is of the formula (d) as defined in claim 1, or A2 and Y together represent a group of the formula (B) as defined in claim 1 and wherein, in formulae (d) and (B), L1 is as defined in claim 1 and R1 is Z, L3—Z, L3-alk—Z or a group substituted by L3—Z or L3-alk—Z, wherein said group, L3 and Z are as defined in claim 1.

8. A complex according to claim 1 wherein:
M is Cu;
X is N;
A1 is a group of formula (a') as defined in claim 1;
A2 and Y together represent a group of formula (C):

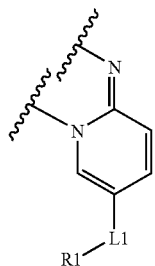

in which L1 and R1 are as defined in claim 1;
L1' is a covalent bond;
R1' is H or a group selected from alkyl, alkoxy and phenyl; and
R2' is as defined in claim 1.

9. A metal complex according to claim 1 which is of formula (IIa):

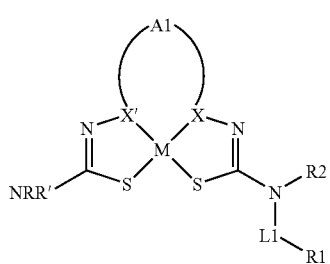

(IIIa)

wherein:
M is Cu;
A1 is:

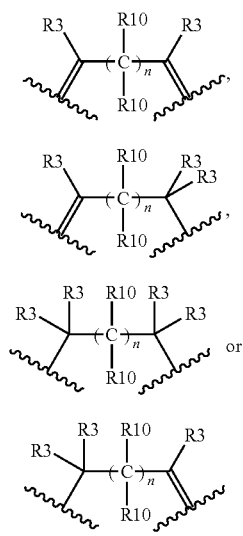

(a')

(b')

(d')

or (e')

X is N and A1 is attached to X via a double bond, or X is N(R11) and A1 is attached to X via a single bond;

X' is N and A1 is attached to X' via a double bond, or X' is N(R11) and A1 is attached to X' via a single bond;

n is 0 or an integer of 1 to 5;

each R11 is independently selected from H and $C_1$-$C_6$ alkyl;

each R10 is independently selected from H, $C_1$-$C_6$ alkyl and phenyl;

R and R', which are the same or different, are each H or a group selected from $C_1$-$C_6$ alkyl, $C_1$-$C_6$ alkoxy and phenyl;

R2 is H or a group selected from $C_1$-$C_6$ alkyl and $C_1$-$C_6$ alkoxy;

each R3, which are the same or different, is H or a group selected from $C_1$-$C_6$ alkyl and phenyl;

L1 is a covalent bond or a linker group selected from —C(O)—, -alk—C(O)—, —C(O)O—, -alk—C(O)O—, —OC(O)—, -alk—OC(O)—, —O—, -alk—O—, —N(R7)—, -alk—N(R7)—, —N(R7)C(O), -alk—N(R7)C(O)—, —C(O)N(R7), -alk—C(O)N(R7), —C(S)—, -alk—C(S)—, —S—, -alk—S—, —C(S)N(R7)—, -alk—C(S)N(R7)—, —N(R7)C(S)—, -alk—N(R7)C(S)—, —S(O)$_2$N(R7)—, -alk—S(O)$_2$N(R7)—, —N(R7)S(O)$_2$—, -alk—N(R7)S(O)$_2$—, —S(O)—, -alk—S(O)—, —N(R7)C(O)O—, -alk—N(R7)C(O)O—, —OC(O)N(R7)—, -alk—OC(O)N(R7)—, —N(R7)C(O)N(R7)—, -alk—N(R7)C(O)N(R7)—, —N(R7)C(S)N(R7)—, -alk—N(R7)C(S)N(R7)—, —N=C(R7)—, -alk—N=C(R7)—, —C(R7)=N— and -alk—C(R7)=N—; R7 is H, alkyl or cycloalkyl; and R1 is Z, L3—Z, -alk—L3—Z or a group selected from an alkyl, carbocyclic, cycloalkyl, heterocyclic, -alk-carbocyclic, -alk-cycloalkyl and -alk-heterocyclic group, which group is further substituted by L3—Z or L3-alk—Z, wherein L3 is as defined above for L1 and Z is a moiety selected from a biologically active molecule, a fluorophore, a cytotoxin, an amino acid, a peptide, an oligopeptide, a polypeptide, a group containing a label, a leaving group which is replaceable by a group containing a label, and a Cu or Zn complex of a bis(thiosemicarbazone) or of a thiosemicarbazone.

10. A metal complex according to claim 1 which is of formula (IIIb):

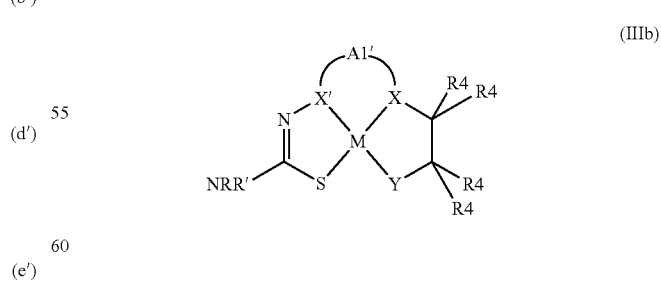

(IIIb)

wherein
M is Cu;
R and R', which are the same or different, are each H or a group selected from $C_1$-$C_6$ alkyl, $C_1$-$C_6$ alkoxy and phenyl;

A1' is a group of formula (a'), (b'), (c'), (d'), (e'), (f'), (g'), (h') or (i'):

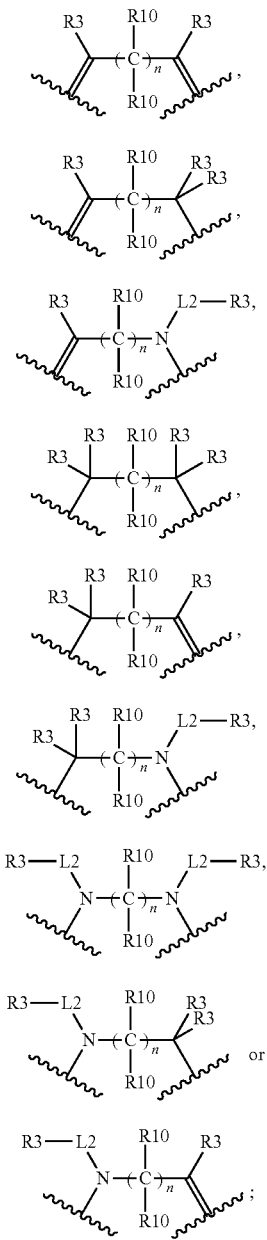

wherein each R3, which are the same or different, is H or a group selected from $C_1$-$C_6$ alkyl and phenyl;
  each L2 is independently selected from —C(O)— and a covalent bond;
  each R10 is independently selected from H, $C_1$-$C_6$ alkyl and phenyl; and n is 0 or an integer of 1 to 5;
  each R4, which are the same or different, is independently selected from H, $C_1$-$C_6$ alkyl and phenyl;
  X is N or P and A1' is attached to X via a double bond, or X is selected from O, S, N(R5) and P(R5) and A1' is attached to X via a single bond;
  Y is selected from O, S, N(R5), P(R5), O(R5) and S(R5);
  each R5 is independently selected from H, $C_1$-$C_6$ alkyl and a group comprising an electron donor group, which donor group is separated by two carbon atoms from the O, N, S or P atom to which R5 is attached.

11. A complex according to claim 1 wherein the Cu is $^{60}$Cu, $^{61}$Cu, $^{62}$Cu, 64Cu or $^{67}$Cu.

12. A complex according to claim 1 which is hypoxic selective.

13. A complex according to claim 1 wherein Z is a Cu complex of a bis(thiosemicarbazone) or of a thiosemicarbazone, thereby creating a dimer wherein two bis(thiosemicarbazone) or thiosemicarbazone Cu complexes are linked by -L1-R1-L1—, L1-alk—R1-L1—, -L1-R1-alk—L1- or -L1-alk—R1-alk—L1- wherein L1 and R1 are as defined in claim 1.

14. A pharmaceutical composition comprising a complex as defined in claim 1 and a pharmaceutically acceptable carrier.

15. A composition according to claim 14 wherein the complex is hypoxic selective.

16. A diagnostic agent or medical imaging agent which comprises a complex as defined in claim 1 which is hypoxic selective.

17. A composition according to claim 15 wherein hypoxic selectivity arises from the redox behaviour of the metal at the centre of the complex.

18. An agent according to claim 16 wherein the complex comprises a fluorophore and wherein the agent is suitable for optical and positron emission tomography (PET) imaging and/or for non-radioactive optical imaging.

19. An agent according to claim 16 wherein the complex comprises a radionuclide and the agent is suitable for the imaging of hypoxic tumours.

20. A diagnostic agent or a medical imaging agent which comprises a complex as defined in claim 1 which is not hypoxic selective and in which Z is a biologically active molecule which serves to target the complex to the desired site in vivo.

21. An agent according to claim 20 in which the biologically active molecule is a monoclonal antibody, a peptide, an oligopeptide or a polypeptide.

22. A method of imaging a cell or in vitro biopsy sample, which method comprises:
  (a) contacting the cell or in vitro biopsy sample with a complex as defined in claim 1; and
  (b) imaging the cell or in vitro biopsy sample.

23. A method of imaging a patient in need thereof, which method comprises:
  (a) administering to the patient a complex as defined in claim 1; and
  (b) imaging the patient.

* * * * *